(12) United States Patent
Iwawaki et al.

(10) Patent No.: US 12,317,746 B2
(45) Date of Patent: May 27, 2025

(54) ORGANIC COMPOUND, ORGANIC LIGHT-EMITTING ELEMENT, DISPLAY APPARATUS, PHOTOELECTRIC CONVERSION APPARATUS, ELECTRONIC APPARATUS, LIGHTING DEVICE, AND MOVING OBJECT

(71) Applicant: CANON KABUSHIKI KAISHA, Tokyo (JP)

(72) Inventors: Hironobu Iwawaki, Kanagawa (JP); Jun Kamatani, Tokyo (JP); Hirokazu Miyashita, Kanagawa (JP); Naoki Yamada, Tokyo (JP); Yosuke Nishide, Kanagawa (JP); Satoru Shiobara, Kanagawa (JP); Hiroki Ohrui, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 795 days.

(21) Appl. No.: 17/535,228

(22) Filed: Nov. 24, 2021

(65) Prior Publication Data

US 2022/0173332 A1    Jun. 2, 2022

(30) Foreign Application Priority Data

Nov. 30, 2020 (JP) .................. 2020-198285

(51) Int. Cl.
*H10K 85/60* (2023.01)
*C07D 471/14* (2006.01)
(Continued)

(52) U.S. Cl.
CPC ....... *H10K 85/6572* (2023.02); *C07D 471/14* (2013.01); *C07D 487/14* (2013.01);
(Continued)

(58) Field of Classification Search
CPC . H10K 85/6572; C07D 471/14; C07D 487/14
See application file for complete search history.

(56) References Cited

U.S. PATENT DOCUMENTS

2019/0333968 A1* 10/2019 Yamada ............... H10K 85/633
2019/0334115 A1* 10/2019 Matsuda ........... H10K 50/8426

FOREIGN PATENT DOCUMENTS

CN      110003222 A     7/2019
KR      20170124412 A   11/2017

OTHER PUBLICATIONS

Machine Translation of KR20170124412 (Year: 2017).*

* cited by examiner

*Primary Examiner* — Jenna N Chandhok
(74) *Attorney, Agent, or Firm* — Canon U.S.A., Inc. IP Division

(57) ABSTRACT

An organic compound represented by formula [1]:

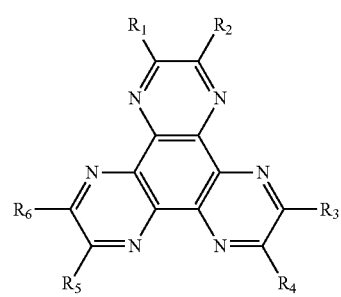

[1]

where in formula [1], $R_1$ to $R_6$ are each independently selected from the group consisting of a hydrogen atom, a
(Continued)

hydrocarbon group, and other substituents having a substituted or unsubstituted alkyl group, a substituted or unsubstituted aryl group, or a substituted or unsubstituted heterocyclic group, at least one of $R_1$ to $R_6$ is one of the other substituents, at least any one of $R_1$ and $R_2$ is a hydrogen atom or a hydrocarbon group, at least any one of $R_3$ and $R_4$ is a hydrogen atom or a hydrocarbon group, and at least any one of $R_5$ and $R_6$ is a hydrogen atom.

21 Claims, 6 Drawing Sheets

(51) Int. Cl.
    *C07D 487/14*     (2006.01)
    *H10K 50/11*     (2023.01)
    *H10K 101/10*     (2023.01)

(52) U.S. Cl.
    CPC ........... *H10K 85/636* (2023.02); *H10K 50/11* (2023.02); *H10K 2101/10* (2023.02)

| No. | COMPOUND | HOMO DISTRIBUTION | LUMO DISTRIBUTION | S₁-T₁ DIFFERENCE (eV) | S₁ (nm) |
|---|---|---|---|---|---|
| B-1 |  |  |  | 0.17 | 488 |
| B-2 |  |  |  | 0.17 | 498 |
| a-1 |  |  |  | 0.36 | 424 |
| a-2 |  |  |  | 0.36 | 425 |
| a-3 |  |  |  | 0.36 | 455 |
| a-4 |  |  |  | 0.52 | 452 |

ORGANIC COMPOUND, ORGANIC LIGHT-EMITTING ELEMENT, DISPLAY APPARATUS, PHOTOELECTRIC CONVERSION APPARATUS, ELECTRONIC APPARATUS, LIGHTING DEVICE, AND MOVING OBJECT

BACKGROUND OF THE INVENTION

Field of the Invention

The present disclosure relates to an organic compound, an organic light-emitting element, a display apparatus, a photoelectric conversion apparatus, an electronic apparatus, a lighting device, and a moving object.

Description of the Related Art

Organic light-emitting elements (hereinafter, also referred to as "organic electroluminescent elements" or "organic EL elements") are electronic devices each including a pair of electrodes and an organic compound layer disposed between these electrodes. The injection of electrons and holes from these pairs of electrodes generates excitons in the light-emitting organic compound in the organic compound layer, and when the excitons return to the ground state, the organic light-emitting element emits light.

Recent progress in organic light-emitting elements has been remarkable, and their features include low driving voltage, various emission wavelengths, fast response time, and enabling light-emitting apparatuses to be thinner and lighter.

Regarding improvements in the efficiency of organic light-emitting elements, devices containing materials having the ability to improve the efficiency, such as phosphorescent materials and delayed fluorescent materials, have been reported. Korean Patent Application Publication No. 2017-0124412 describes a compound A-1 below. Chinese Patent Application Publication No. 110003222 describes compound A-2 below.

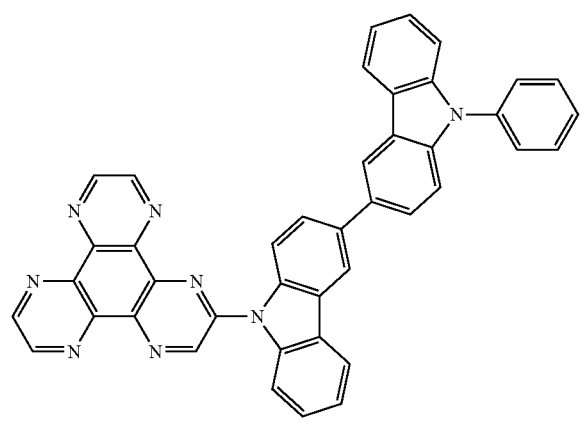

A-1

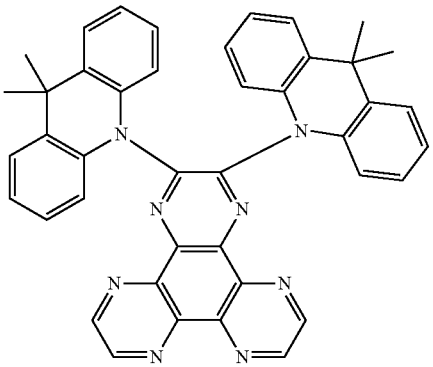

A-2

When the compound A-1 described in Korean Patent Application Publication No. 2017-0124412 and the compound A-2 described in Chinese Patent Application Publication No. 110003222 are used for light-emitting layers of organic light-emitting elements, there is still a disadvantage with luminous efficiency.

The present disclosure has been made in light of the above disadvantage. The present disclosure provides an organic compound having superior luminous efficiency.

SUMMARY OF THE INVENTION

The present disclosure provides an organic compound represented by formula [1]:

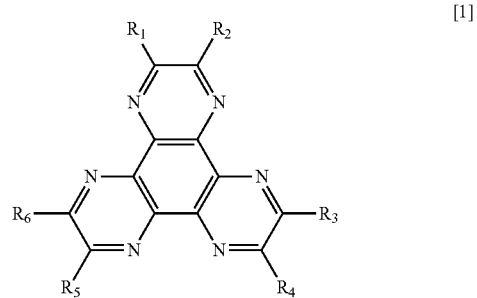

[1]

where in formula [1], $R_1$ to $R_6$ are each independently selected from the group consisting of a hydrogen atom, a hydrocarbon group, and substituents represented by formulae [2] to [18], at least one of $R_1$ to $R_6$ is a substituent represented by any of formulae [2] to [18], at least any one of $R_1$ and $R_2$ is a hydrogen atom or a hydrocarbon group, at least any one of $R_3$ and $R_4$ is a hydrogen atom or a hydrocarbon group, and at least any one of $R_5$ and $R_6$ is a hydrogen atom,

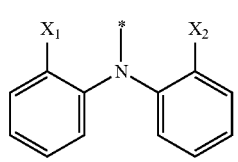

[2]

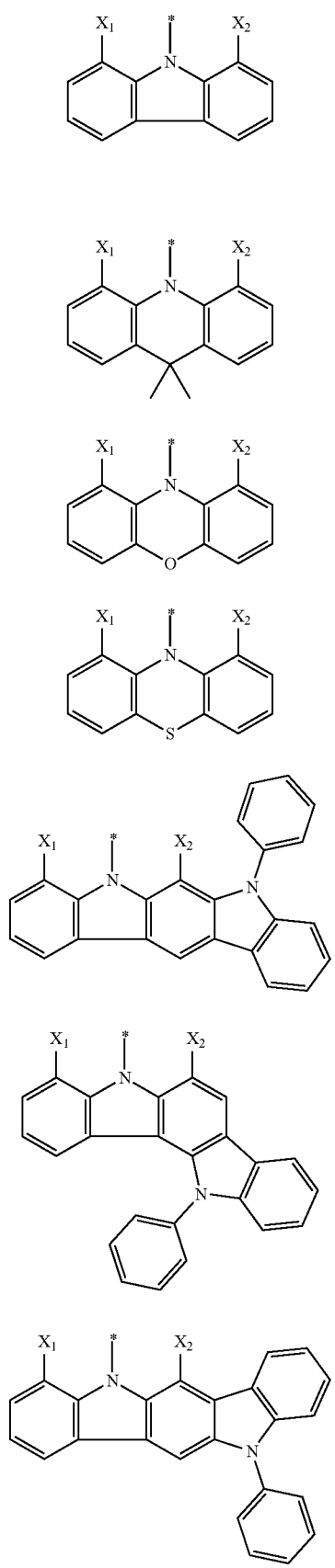
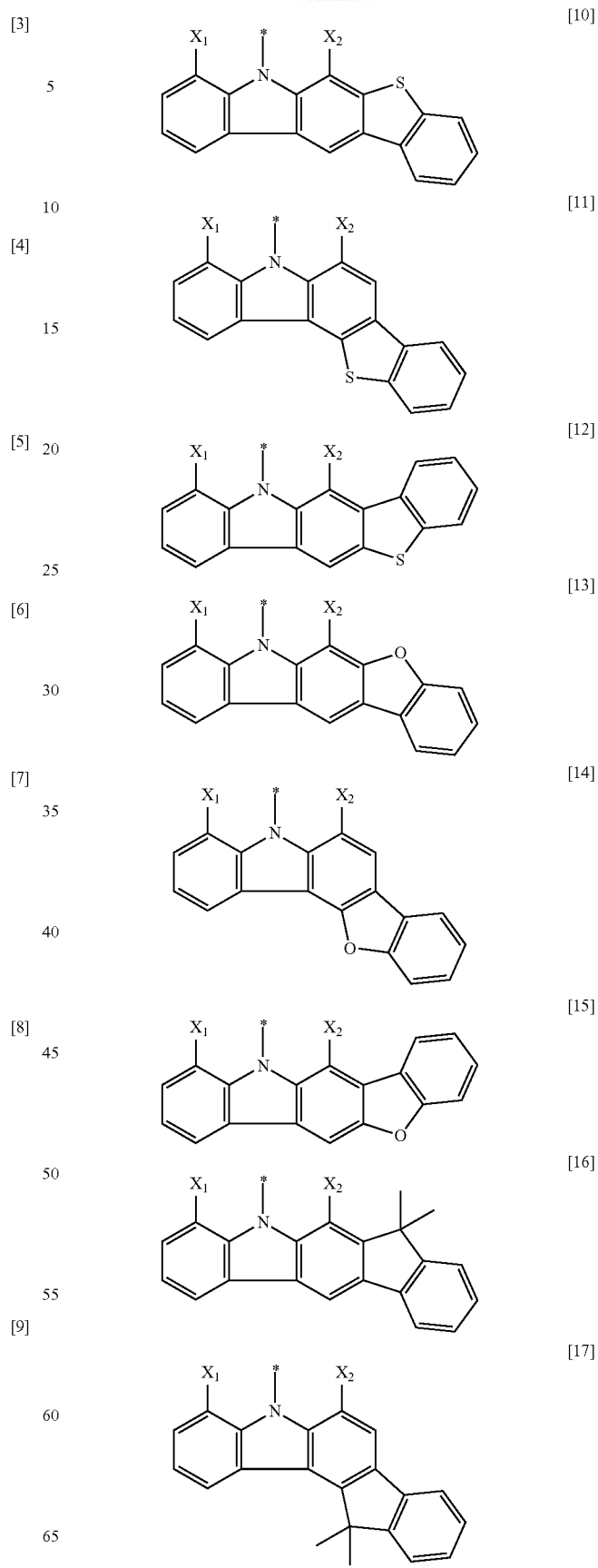

-continued

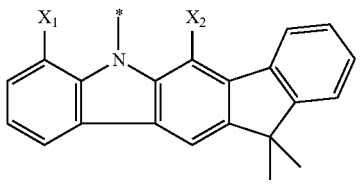
[18]

where in formulae [2] to [18], $X_1$ and $X_2$ are each independently selected from a substituted or unsubstituted alkyl group, a substituted or unsubstituted aryl group, and a substituted or unsubstituted heterocyclic group.

Further features of the present disclosure will become apparent from the following description of exemplary embodiments with reference to the attached drawings.

DESCRIPTION OF THE EMBODIMENTS

Organic Compound

Figure 1:
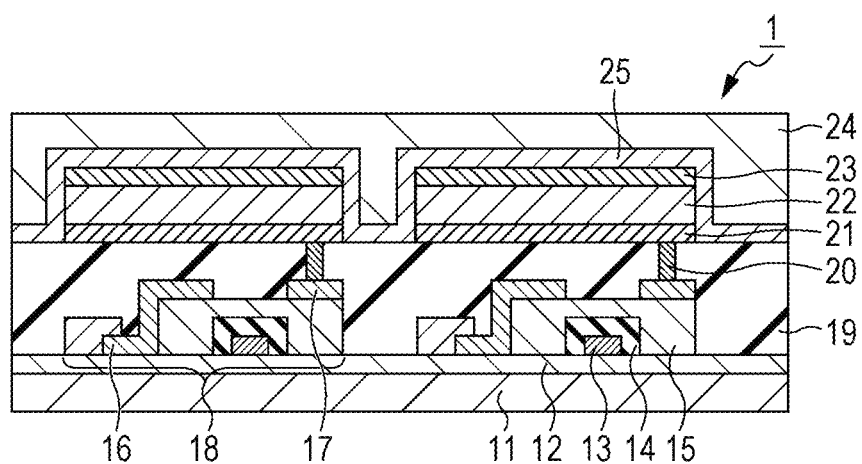
FIG. 1 is a schematic cross-sectional view of an example of a display apparatus including organic light-emitting elements according to an embodiment of the present disclosure.

An organic compound according to an embodiment will be described. The organic compound according to this embodiment is represented by formula [1]:

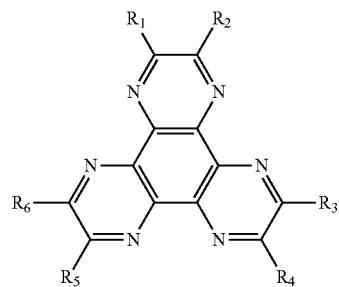
[1]

where in formula [1], $R_1$ to $R_6$ are each independently selected from the group consisting of a hydrogen atom, a hydrocarbon group, and substituents represented by formulae [2] to [18], at least one of $R_1$ to $R_6$ is a substituent represented by any of formulae [2] to [18], at least any one of $R_1$ and $R_2$ is a hydrogen atom or a hydrocarbon group, at least any one of $R_3$ and $R_4$ is a hydrogen atom or a hydrocarbon group, and at least any one of $R_5$ and $R_6$ is a hydrogen atom.

In other words, in formula [1], any one of $R_1$ and $R_2$ is a hydrogen atom or a hydrocarbon group.

In formula [1], when any of $R_1$ to $R_6$ is a hydrocarbon group, the hydrocarbon group can be a substituted or unsubstituted alkyl group having 1 to 6 carbon atoms, or a substituted or unsubstituted aryl group having 6 to 10 carbon atoms. That is, in formula [1], $R_1$ to $R_6$ can each be independently selected from the group consisting of a hydrogen atom, a substituted or unsubstituted alkyl group having 1 to 6 carbon atoms, a substituted or unsubstituted aryl group having 6 to 10 carbon atoms, and substituents represented by formulae [2] to [18] below.

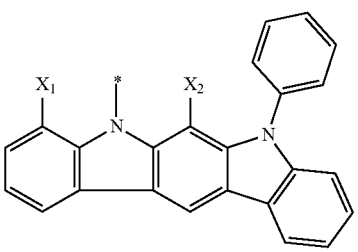

-continued

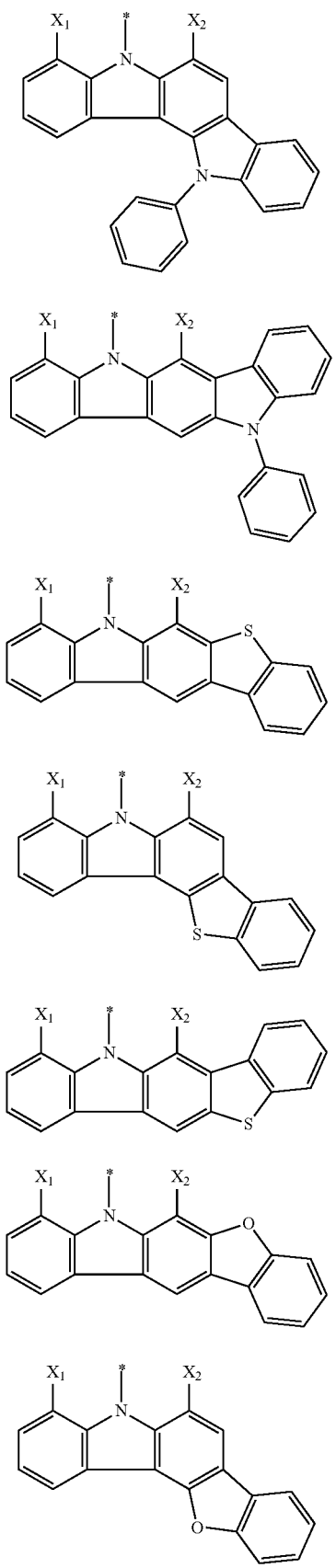

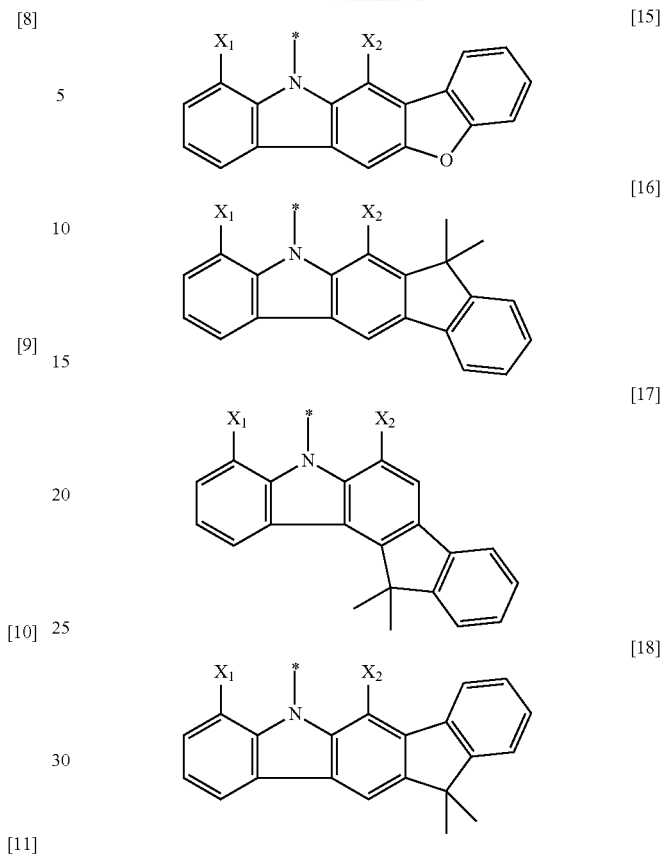

In formulae [2] to [18], $X_1$ and $X_2$ are each independently a substituent selected from a substituted or unsubstituted alkyl group, a substituted or unsubstituted aryl group, and a substituted or unsubstituted heterocyclic group. In formulae [2] to [18], $X_1$ and $X_2$ can each be a substituent independently selected from a substituted or unsubstituted alkyl group having 6 to 10 carbon atoms, a substituted or unsubstituted aryl group having 6 to 10 carbon atoms, and a substituted or unsubstituted heterocyclic group having 3 to 9 carbon atoms.

Non-limiting examples of an alkyl group that can be used as each of $X_1$ and $X_2$ include a methyl group, an ethyl group, a n-propyl group, an isopropyl group, a n-butyl group, a tert-butyl group, a sec-butyl group, and a cyclohexyl group. Among these, a methyl group, an ethyl group, a n-propyl group, an isopropyl group, a n-butyl group, a tert-butyl group, a sec-butyl group, and a cyclohexyl group, which have 1 to 6 carbon atoms, can be used as $X_1$ and $X_2$.

Non-limiting examples of an aryl group that can be used as each of $X_1$ and $X_2$ include a phenyl group, a naphthyl group, and an indenyl group. Among these, a phenyl group, a naphthyl group, and an indenyl group, which have 6 to 10 carbon atoms, can be used as $X_1$ and $X_2$.

Non-limiting examples of a heterocyclic group that can be used as each of $X_1$ and $X_2$ include a pyridyl group, a pyrimidinyl group, a pyrazinyl group, a triazinyl group, a quinolinyl group, an isoquinolinyl group, an indolyl group, a benzofuranyl group, and a benzothiophenyl group.

Among these, a pyridyl group, a pyrimidinyl group, a pyrazinyl group, a triazinyl group, a quinolinyl group, an isoquinolinyl group, an indolyl group, a benzofuranyl group, and a benzothiophenyl group, which have 3 to 9 carbon atoms, can be used as $X_1$ and $X_2$.

Non-limiting examples of a substituent that may be further included in the alkyl group, aryl group, or heterocyclic group denoted by $X_1$ and $X_2$ include alkyl groups, such as a methyl group, an ethyl group, a n-propyl group, an isopropyl group, a n-butyl group, and a tert-butyl group, aryl groups, such as a phenyl group and a naphthyl group, and heterocyclic groups, such as a pyridyl group and a pyrimidinyl group.

A method for synthesizing an organic compound according to the embodiment will be described below. The organic compound according to the embodiment is synthesized in accordance with, for example, any of reaction schemes 1 to 3 illustrated below.

Reaction scheme 1

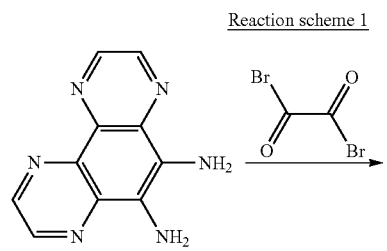

Reaction scheme 2

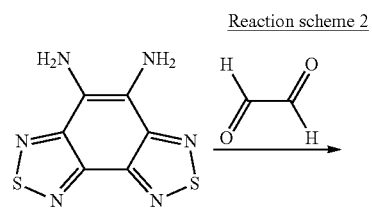

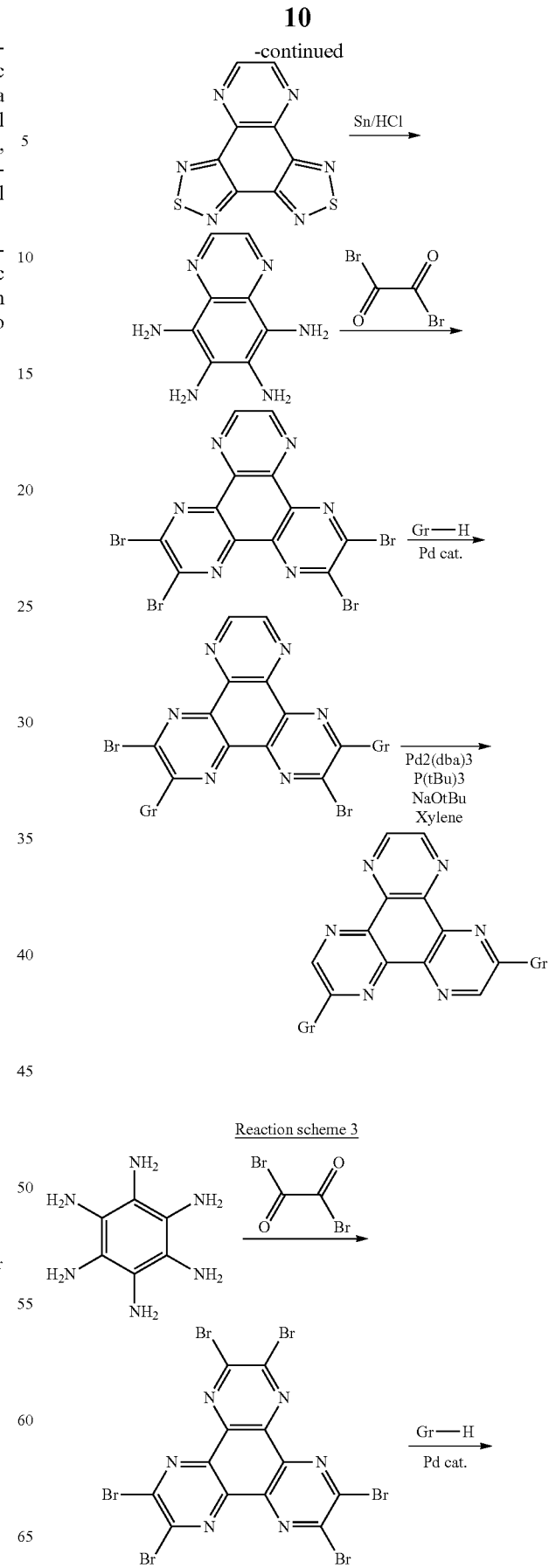

-continued

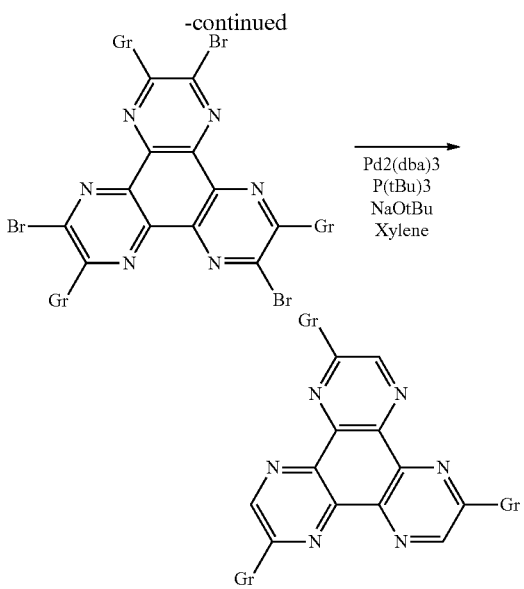

Each substituent Gr in the above reaction schemes 1 to 3 is selected from the above substituent group represented by formulae [2] to [18]. In each of the above reaction schemes 1 to 3, various compounds having different substituents Gr can be synthesized by appropriately using different compounds represented by Gr-H. The synthesis method is not limited thereto. The synthesis method will be described in detail in Examples.

The organic compound according to the embodiment has features described below. The use of the organic compound according to the embodiment for an organic light-emitting element allows the organic light-emitting element to have high luminous efficiency and superior driving durability characteristics. A basic skeleton according to the embodiment refers to a skeleton in which $R_1$ to $R_6$ of the compound represented by formula [1] are all hydrogen atoms. The skeleton in which $R_1$ to $R_6$ of the compound represented by formula [1] are all hydrogen atoms is also referred to as a "hexaazatriphenylene skeleton".

(1) The compound contains, as a basic skeleton, an electron-withdrawing hexaazatriphenylene skeleton in which at least one of $R_1$ to $R_6$ is an electron-donating substituent represented by any of formula [2] to [18], and thus has a small energy gap between $S_1$ and $T_1$.

(2) The substituent attached to the hexaazatriphenylene skeleton, which is the basic skeleton, having a structure with a high degree of flatness is a substituent represented by any of formulae [2] to [18] having a relatively large steric effect and thus is less likely to undergo molecular association.

(3) The compound has a structure in which a substituent represented by any of formulae [2] to [18] is arranged in a sterically twisted manner with respect to the hexaazatriphenylene skeleton serving as the basic skeleton and thus has an $S_1$ energy level such that the compound can be used as a material for a green- or red-light-emitting layer.

The above-described features will be described below.

(1) The compound contains, as a basic skeleton, an electron-withdrawing hexaazatriphenylene skeleton in which at least one of $R_1$ to $R_6$ is an electron-donating substituent represented by any of formula [2] to [18], and thus has a small energy gap between $S_1$ and $T_1$.

The inventors have focused on the electron distribution of the highest occupied molecular orbital (HOMO) and the lowest unoccupied molecular orbital (LUMO) of the compound represented by formula [1] in creating the organic compound.

Figure 6:
FIG. 6 is a schematic view of electron distributions of highest occupied molecular orbitals (HOMOs) and lowest unoccupied molecular orbitals (LUMOs) of compounds.
Figure 6:
Figure 6:
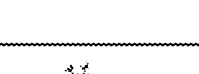
Figure 6:
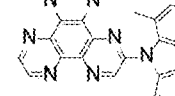
Figure 6:
Figure 6:
Figure 6:
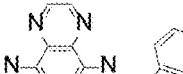
Figure 6:
Figure 6:
Figure 6:
Figure 6:
Figure 6:
Figure 6:
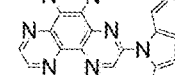
Figure 6:
Figure 6:
Figure 6:
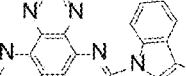
Figure 6:
Figure 6:

As illustrated in FIG. 6, in each of exemplified compounds B-1 and B-2 according to the embodiment, a moiety occupying the electron orbital distribution of the HOMO and a moiety occupying the electron orbital distribution of the LUMO are separated. It can be seen that there are only a few portions occupying both the HOMO and the LUMO.

This leads to a small overlap integral and a small energy difference between the excited singlet state $S_1$ and the excited triplet state $T_1$. Specifically, the energy gaps ($\Delta ST$) between $S_1$ and $T_1$ of exemplified compounds B-1 and B-2 are as small as 0.17 eV and 0.17 eV, respectively. In contrast, the energy gaps (AST) between $S_1$ and $T_1$ of comparative compounds a-1, a-2, a-3, and a-4 are as large as 0.36 eV, 0.36 eV, 0.36 eV, and 0.52 eV, respectively.

The above feature is an effect due to the fact that the compound contains an electron-withdrawing, nitrogen-containing fused-ring skeleton serving as the basic skeleton and an electron-donating amino group serving as a substituent and that the amino group serving as a substituent is arranged in a twisted manner with respect to the basic skeleton. The substituent in the compound represented by formula [1] according to the embodiment is represented by any of formulae [2] to [18], and the substituent represented by any of formulae [2] to [18] further contains substituents $X_1$ and $X_2$. The substituents $X_1$ and $X_2$ are arranged near a binding position where the entire substituent represented by any of formulae [2] to [18] is bound to the basic skeleton, and are arranged at positions that can provide a steric effect with respect to the basic skeleton. In this embodiment, the substituents $X_1$ and $X_2$ are each an alkyl group, an aryl group, or a heterocyclic group. Thus, the substituent represented by any of formulae [2] to [18] provides a relatively large steric effect with respect to the basic skeleton. The hexaazatriphenylene skeleton, which is the basic skeleton, has a structure with a high degree of flatness. Because of the steric effect described above, the substituent represented by any of formulae [2] to [18] is arranged in a twisted manner with respect to the basic skeleton. In other words, the compound represented by formula [1] has a structure in which a plane containing the substituent represented by any of formulae [2] to [18] and a plane containing the hexaazatriphenylene skeleton serving as the basic skeleton are not parallel but intersect each other.

Comparative compounds a-1 to a-3, A-1, and A-2 also each have a structure in which the hexaazatriphenylene skeleton serving as the basic skeleton contains an amino group as a substituent. Unlike the substituents represented by formulae [2] to [18], the substituents in these comparative compounds contain no substituents that provide a relatively high steric effect. More specifically, portions of the substituents of the comparative compounds a-1 to a-3, A-1, and A-2 corresponding to the substituents $X_1$ and $X_2$ of the substituents represented by formulae [2] to [18] are not substituted, that is, the portions are hydrogen atoms. Unlike the substituents represented by formulae [2] to [18], no steric effect is present. Thus, comparative compounds a-1 to a-3 and A-1 and A-2 each have a structure in which a plane containing the substituents and the plane containing the basic skeleton are parallel. That is, each of the comparative compounds does not have a structure in which the basic skeleton and the substituent are arranged in a sterically twisted manner. As also illustrated in FIG. 6, in each of comparative compounds a-1 to a-3, A-1, and A-2, a moiety occupying the electron orbital distribution of the HOMO and a moiety occupying the electron orbital distribution of the LUMO are not separated, and the overlap between the HOMO and LUMO is large. This results in a large energy gap between $S_1$ and $T_1$.

The above calculation results were visualized using molecular orbital calculations. As the molecular orbital calculation method, the density functional theory (DFT), which is widely used at present, was used with the B3LYP functional and 6-31G* as the basis function. The molecular orbital calculation method was performed using Gaussian 09 (Gaussian 09, Revision C.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford CT, 2010), which is widely used at present. Hereinafter, the molecular orbital calculations in the present specification were performed using the same method.

As described above, the compound represented by formula [1] according to the embodiment is characterized by having a small energy difference ($\Delta ST$) between $S_1$ and $T_1$. When the compound according to the embodiment is used in the light-emitting layer of an organic light-emitting element, it is possible to provide the device with high luminous efficiency. The reason for this is as follows: For excitons consisting of singlet and triplet excitons in a ratio of 1:3, the triplet excitons, which undergo thermal deactivation normally, can be used for delayed fluorescence from the excited singlet state due to the small energy difference between $S_1$ and $T_1$. For reverse intersystem crossing to convert the triplet excitons into the excited singlet state, a smaller energy difference between $S_1$ and $T_1$ is advantageous because of a smaller energy barrier. The compound according to the embodiment satisfies that condition and thus is advantageous. Accordingly, the device having high luminous efficiency can be provided.

(2) The substituent attached to the hexaazatriphenylene skeleton, which is the basic skeleton, having a structure with a high degree of flatness is a substituent represented by any of formulae [2] to [18] having a relatively large steric effect and thus is less likely to undergo molecular association.

The inventors have focused on the flatness of the organic compound represented by formula [1] in creating the organic compound. The basic skeleton of the compound according to the embodiment is the hexaazatriphenylene skeleton having a structure with a high degree of flatness. The high degree of flatness easily causes molecular stacking. In other words, molecular association may occur easily. In organic light-emitting elements, molecular association leads to a decrease in efficiency due to concentration quenching. It is also disadvantageous for reverse intersystem crossing. This is because triplet-triplet exciton annihilation (TTA) due to energy transfer of triplet excitons between molecules occurs easily, and reverse intersystem crossing to singlet excitons does not easily occur.

As described above, the compound represented by formula [1] has a structure in which the substituent represented by any of formulae [2] to [18] is arranged in a sterically twisted manner with respect to the basic skeleton. Thus, the substituent represented by any of formulae [2] to [18] can reduce the degree of flatness of the basic skeleton. Accordingly, the compound represented by formula [1] has relatively low degree of flatness. Thus, molecular stacking is less likely to occur, so that molecular association can be less likely to occur. For this reason, when the compound according to the embodiment is used in the light-emitting layer of an organic light-emitting element, concentration quenching is less likely to occur because molecular association is less likely to occur, thus resulting in an organic light-emitting element with high luminous efficiency.

The above feature is also effective in improving the amorphous nature of the organic compound. In the case where the compound according to the embodiment is used in the organic layer (organic compound layer) of an organic light-emitting element, a stable amorphous film that is less likely to crystallize can be formed. Thus, the organic light-emitting element has superior durability without the occurrence of crystallization even in the case of long-term operation.

The above feature is also effective in improving sublimability. The improvement of sublimability enables the purification of the material by sublimation and the production of an organic light-emitting element by vapor deposition. This can reduce the amount of impurities contained in the organic light-emitting element and can inhibit deteriorations in luminous efficiency and driving durability due to impurities.

(3) The compound has a structure in which a substituent represented by any of formulae [2] to [18] is arranged in a sterically twisted manner with respect to the hexaazatriphenylene skeleton serving as the basic skeleton and thus has an $S_1$ energy level such that the compound can be used as a material for a green- or red-light-emitting layer.

Exemplified compound B-1, which is one of the compounds represented by formula [1], has a structure in which the carbazole group, which is an amino substituent, is substituted with methyl groups at the 1- and 8-positions, as compared to the comparative compound a-1. This results in a structure in which the amino substituent is arranged in a sterically twisted manner with respect to the basic skeleton, as described above. The energy level of $S_1$ of comparative compound a-1 is 424 nm, whereas the energy level of $S_1$ of exemplified compound B-1 is 488 nm. In other words, exemplified compound B-1 is a compound having an emission wavelength about 64 nm longer than comparative compound a-1. It is thus possible to provide a compound that is advantageous as a green light-emitting material. A further increase in the number of amino substituents can further reduce the $S_1$ energy level to change the emission wavelength to an advantageous one as a green- or red-light-emitting material. Accordingly, the compound represented by formula [1] can be used as a green- or red-light-emitting material.

The compound according to an embodiment of the present disclosure can be used in the light-emitting layer of an organic light-emitting element. In this case, the compound has the following features.

(4) The compound according to the embodiment is mixed with a host material in the light-emitting layer to facilitate exciton recombination of the compound according to the embodiment, thereby providing the light-emitting element with high efficiency.

(5) The mixture of the compound according to the embodiment and the host material in the light-emitting layer and the presence of a light-emitting material provide the light-emitting element with high efficiency and high color purity.

(6) The use of a hydrocarbon compound as the light-emitting material provides the light-emitting element with high efficiency and good durability characteristics.

Features (4) to (6) above will be described below.

(4) The compound according to the embodiment is mixed with a host material in the light-emitting layer to facilitate exciton recombination of the compound according to the embodiment, thereby providing the light-emitting element with high efficiency.

The compound according to the embodiment is a compound containing an electron-withdrawing, nitrogen-containing heterocyclic group and an electron-donating amino group. When the compound according to the embodiment is mixed with the host material in the light-emitting layer of the organic light-emitting element, the light-emitting layer is an electron-trapping light-emitting layer due to the contribution of the electron-withdrawing properties or a hole-trapping light-emitting layer due to the contribution of the electron-donating properties.

Accordingly, in the light-emitting layer, electrons or holes fed from a transport layer are trapped by the compound according to the embodiment, and exciton recombination occurs. As described in feature (1) above, the compound according to the embodiment has a small energy difference between $S_1$ and $T_1$, can efficiently produce delayed fluorescence in the light-emitting layer, and can use a larger number of triplet excitons for light emission.

In particular, when the host material is a hydrocarbon compound, the LUMO of the compound according to the embodiment tends to be at a lower level (farther from the vacuum level) than the host material, or the HOMO of the compound according to the embodiment tends to be at a higher level (closer to the vacuum level) than the host material. Thus, the compound according to the embodiment traps electrons and holes more easily, resulting in a greater effect described above. The hydrocarbon compound is a compound that consists of only carbon and hydrogen in its molecule.

As described in feature (2) above, the compound according to the embodiment is less likely to undergo molecular association, and thus is less likely to undergo concentration quenching in the host material. This effect leads to the prevention of quenching due to exciton interaction when the compound according to the embodiment is in the excited state, and is effective in efficiently producing delayed fluorescence in the light-emitting layer.

(5) The mixture of the compound according to the embodiment and the host material in the light-emitting layer and the presence of a light-emitting material provide the light-emitting element with high efficiency and high color purity.

The use of the light-emitting layer that contains the compound according to the embodiment and that is doped with a light-emitting material having a high emission quantum yield or a light-emitting material whose emission spectrum has a spectrum appropriate for exhibiting high color purity provides a light-emitting element having even higher efficiency and high color purity. In this case, the compound according to the embodiment needs to be contained in a concentration sufficient to preferentially trap electrons and holes in the light-emitting layer in order to facilitate exciton recombination. For this reason, the concentration of the compound according to the embodiment is preferably 0.1% or more by mass and 45% or less by mass, more preferably 1% or more by mass and 35% or less by mass, particularly preferably 10% or more by mass and 30% or less by mass, based on the entire light-emitting layer. The concentration of the compound according to the embodiment may be 15% or more by mass based on the entire light-emitting layer. When the compound according to the embodiment is considered as a light-emitting material, a smaller doping concentration can be used because the element is less susceptible to influences of concentration quenching and a change in emission spectrum due to intermolecular interactions. Thus, the light-emitting layer can be doped with a light-emitting material other than the compound according to the embodiment. The doping concentration of the light-emitting material to be further doped in the light-emitting layer is preferably 0.01% or more by mass and 20% or less by mass, more preferably 1% or more by mass and 15% or less by mass, even more preferably 10% or less by mass. Accordingly, it is possible to provide the light-emitting element with high efficiency and high color purity. A green- or red-light-emitting material can be used as the light-emitting material. This is because the compound according to the embodiment is a green-light-emitting material.

(6) The use of a hydrocarbon compound as the light-emitting material provides the light-emitting element with high efficiency and good durability characteristics.

Since the compound according to the embodiment has a strong electron-withdrawing, nitrogen-containing heterocyclic group, the light-emitting material to be doped and used together as described in (5) above can be a light-emitting material that has no electron-donating amino group and that is a hydrocarbon compound. The reasons for this are as follows: When a light-emitting material having an amino group is used together with the compound according to the embodiment, the nitrogen-containing heterocyclic group of the compound according to the embodiment and the light-emitting material having an amino group interact with each other in the light-emitting layer. This may lead to a decrease in luminous efficiency due to exciplex formation and a deterioration in the color purity of the light-emitting element due to a change in the emission spectrum of the light-emitting material.

Thus, the light-emitting material to be used with the compound according to the embodiment can be a hydrocarbon compound, or even a fused polycyclic compound containing a five-membered ring. This is because the structure is less susceptible to oxidation due to its higher ionization potential. The hydrocarbon compound is a compound consisting of only carbon and hydrogen in its molecule.

As described above, the organic light-emitting element with high luminous efficiency can be provided by mixing the compound according to the embodiment with the host material in the light-emitting layer. Here, the light-emitting material may be the compound according to the embodiment. Alternatively, the light-emitting material according to the embodiment may be mixed with a light-emitting material, and the light-emitting material according to the embodiment functions as an assist material.

The use of a light-emitting material with good color purity makes it possible to provide an organic light-emitting element with high efficiency and high color purity. When the host material is a hydrocarbon compound, the compound according to the embodiment can easily trap electrons and holes to contribute to higher efficiency.
Specific examples of the organic compound according to the embodiment are illustrated below. However, the present disclosure is not limited thereto.
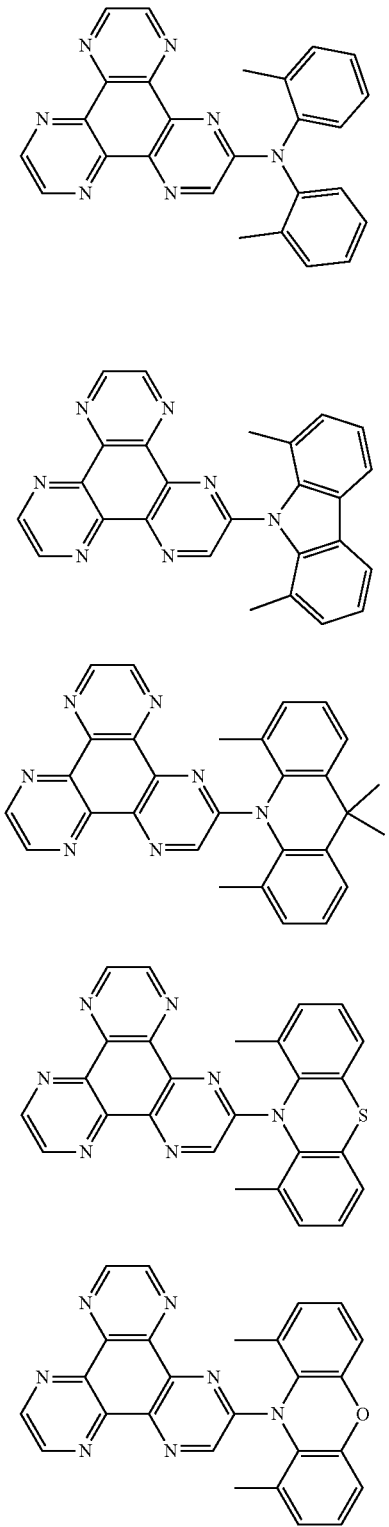
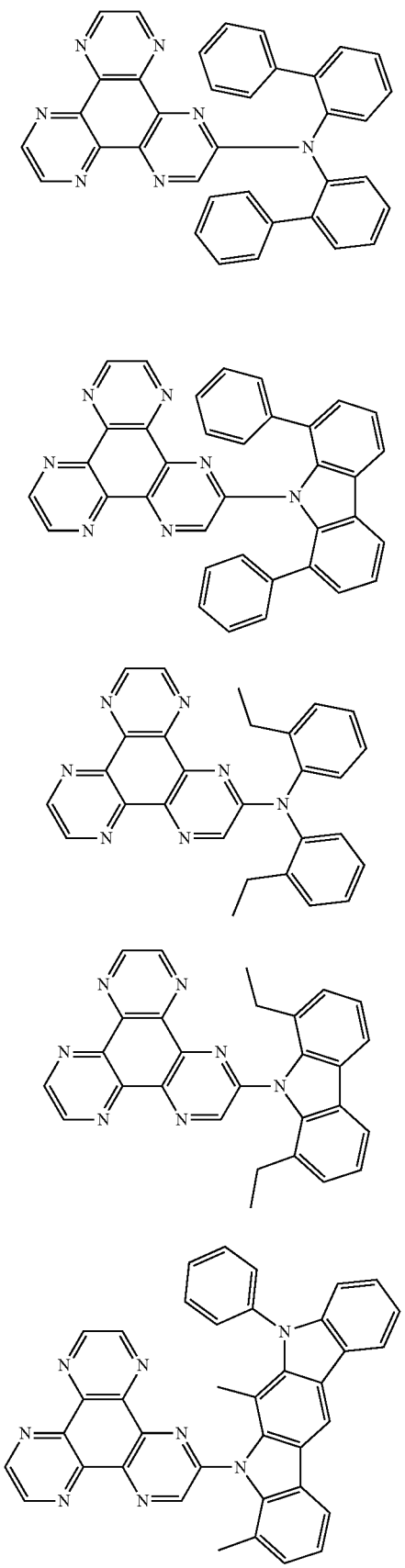

-continued
C-11
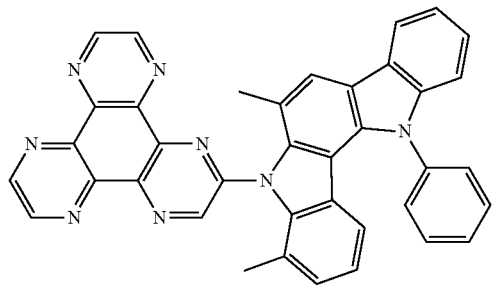
C-12
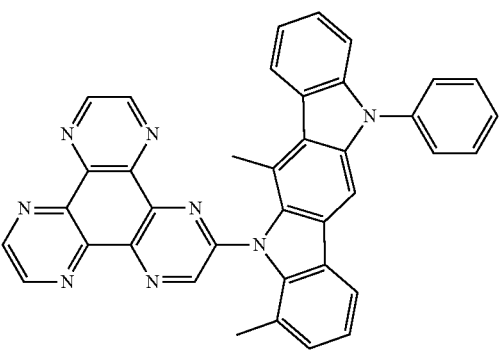
C-13
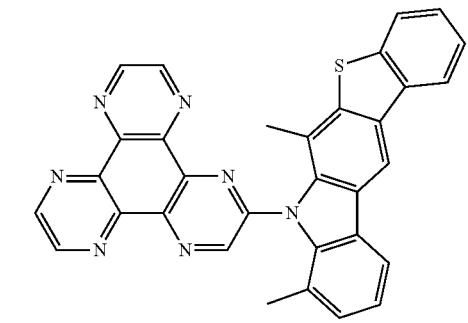
C-14
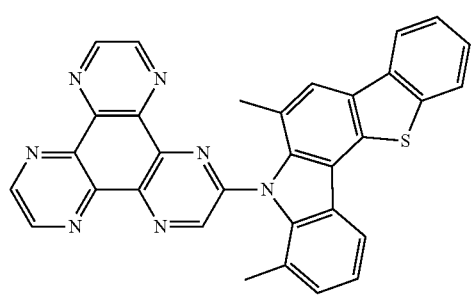
C-15
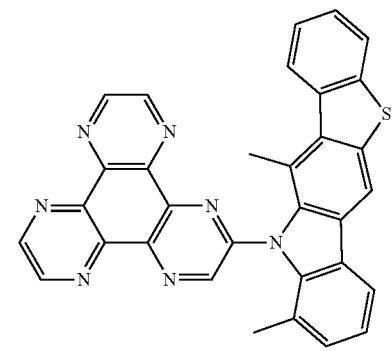
-continued
C-16
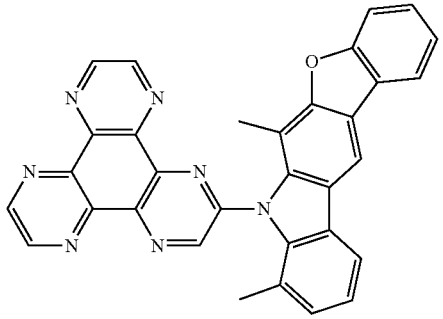
C-17
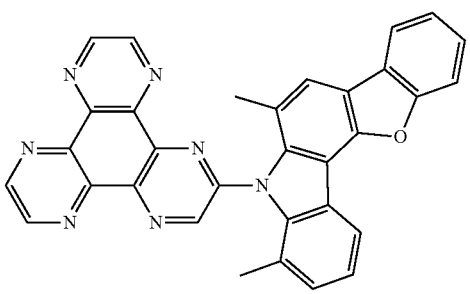
C-18
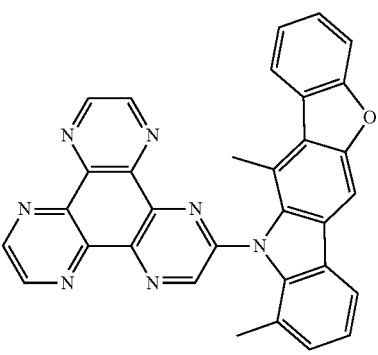
C-19
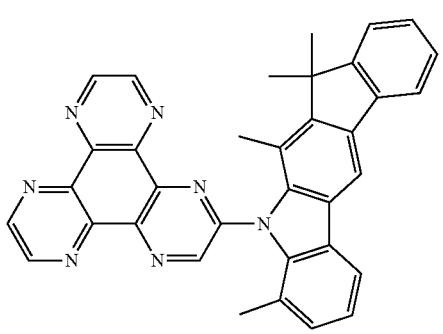
C-20
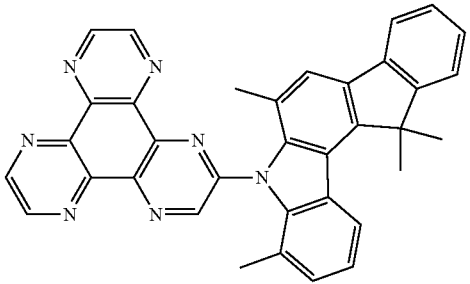

C-21
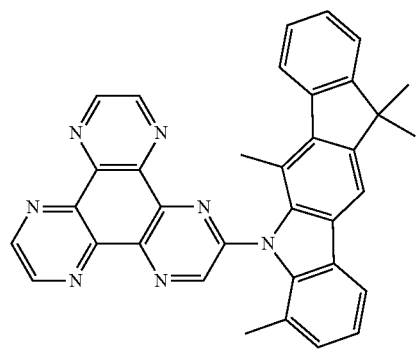
C-22
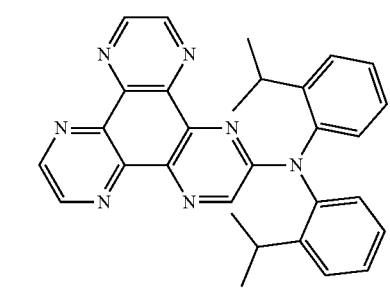
C-23
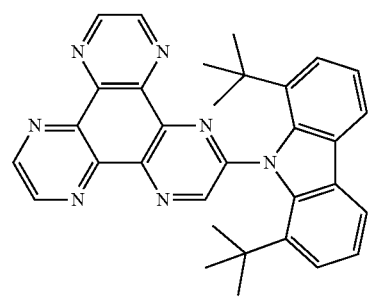
C-24
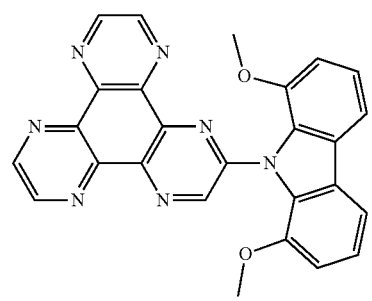
C-25
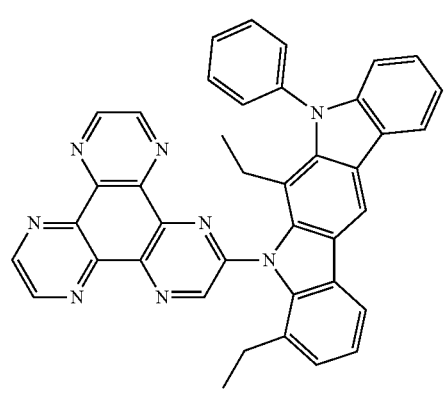
C-26
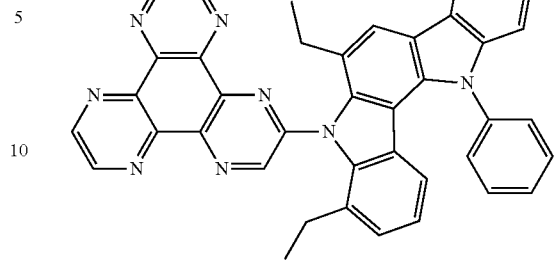
C-27
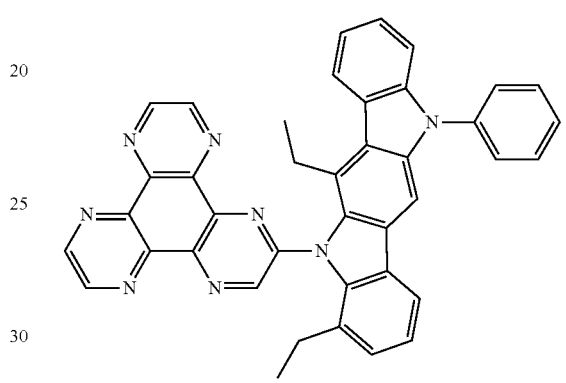
C-28
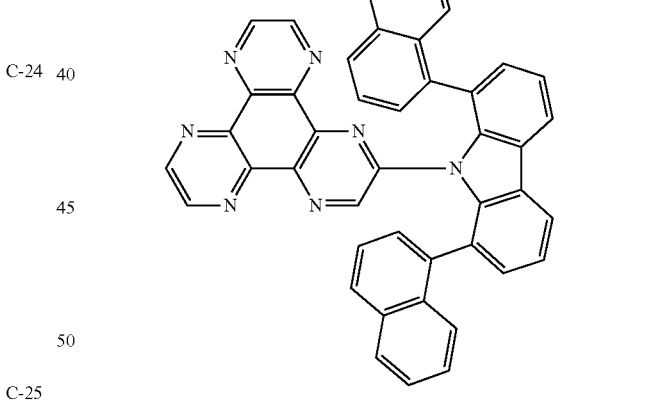
C-29
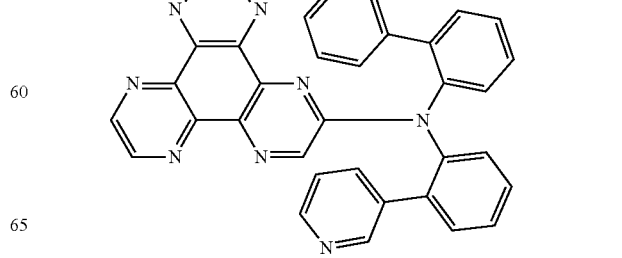

C-30
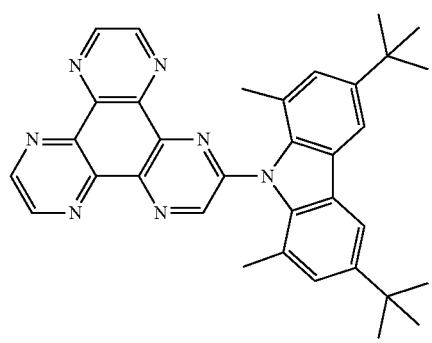
C-31
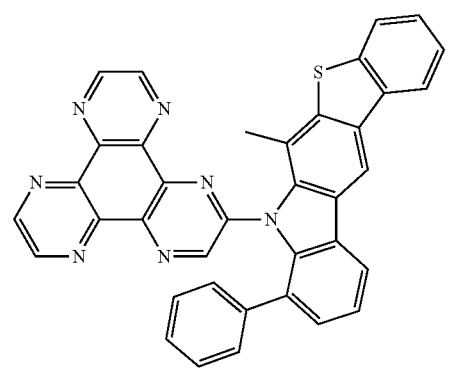
C-32
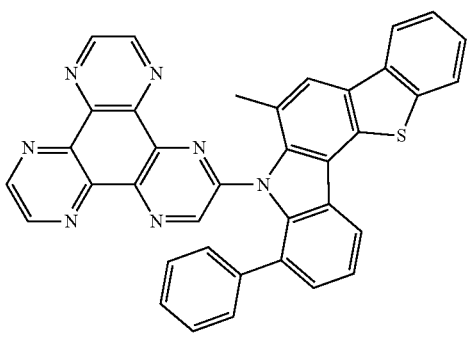
C-33
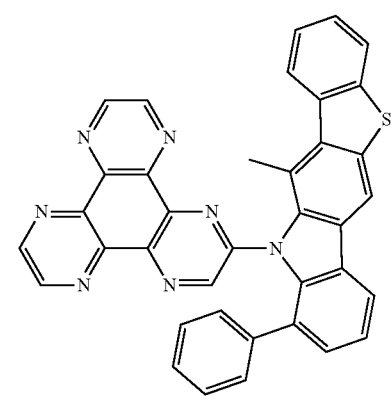
C-34
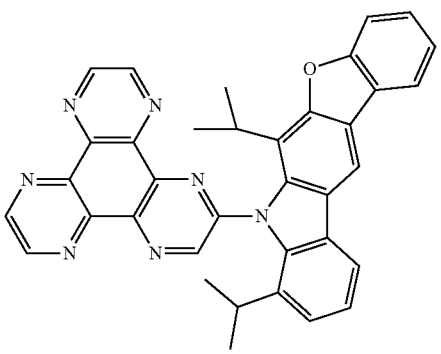
C-35
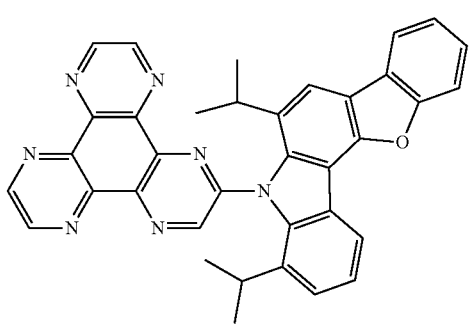
C-36
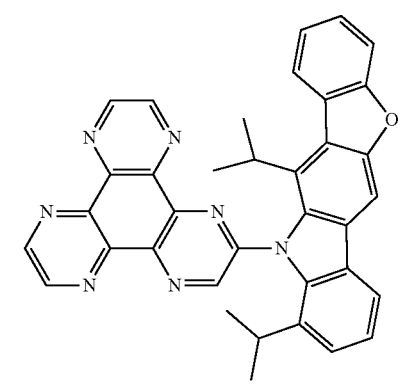
C-37
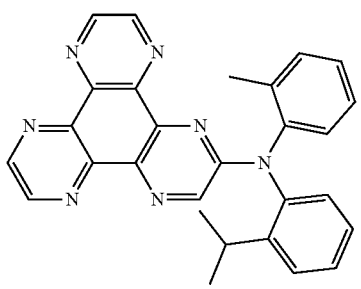
C-38
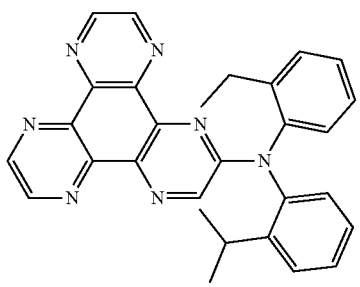

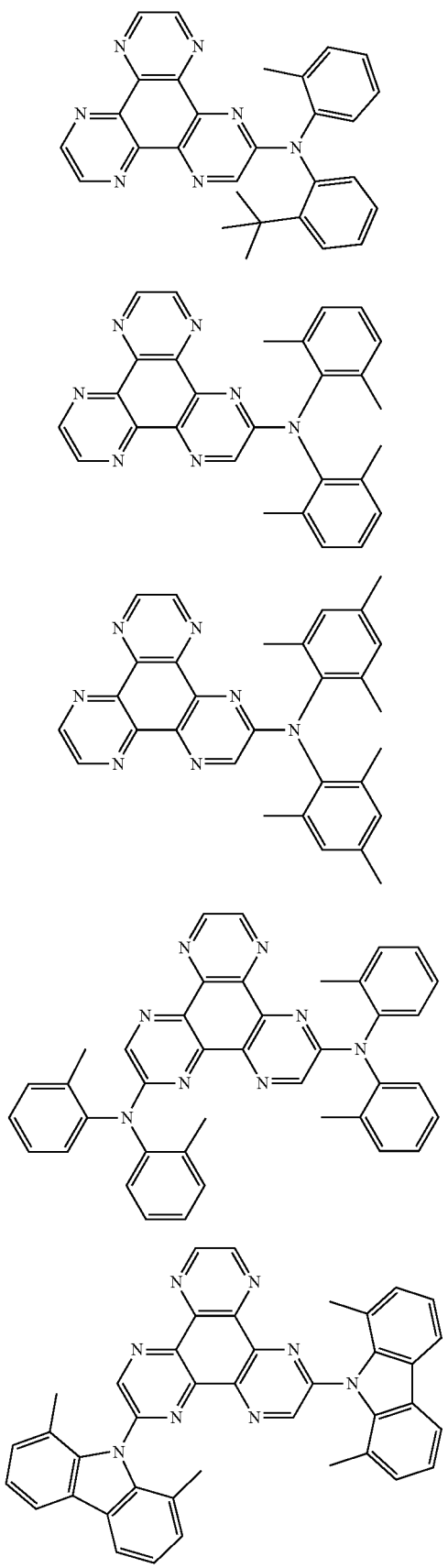
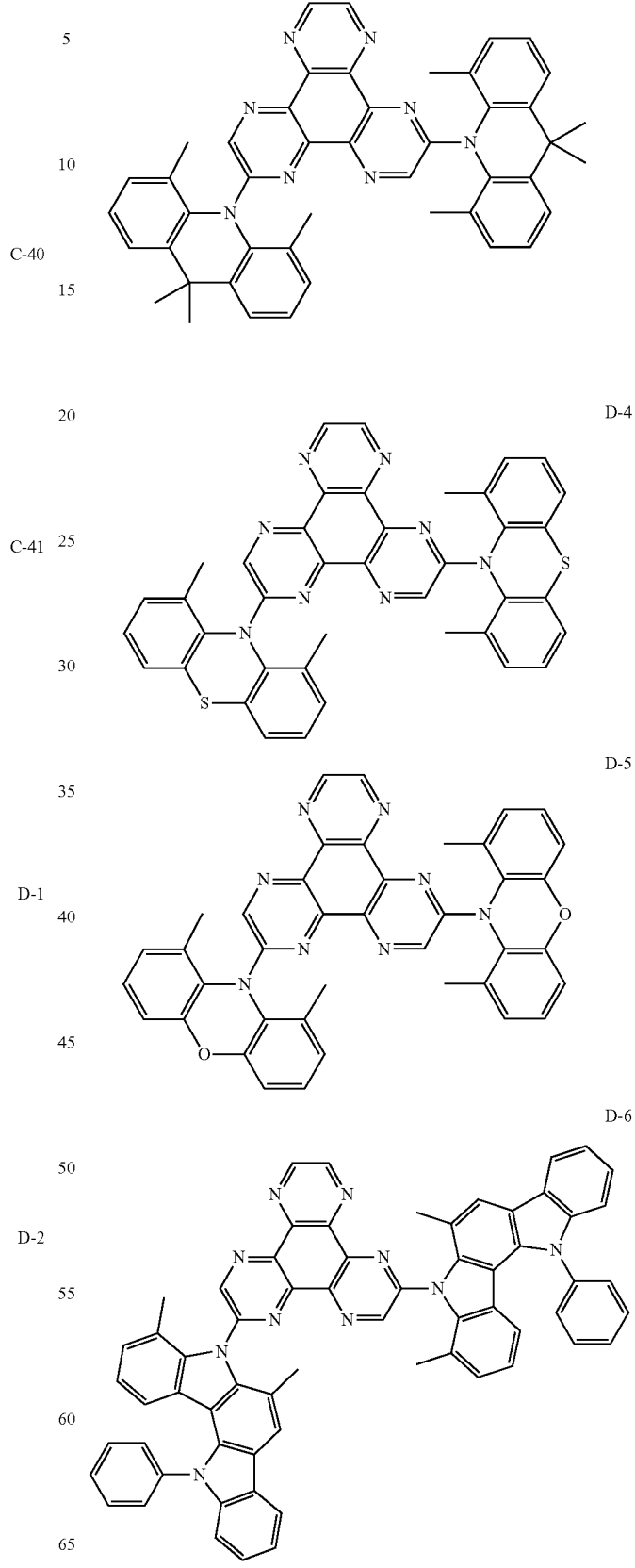

-continued
D-7
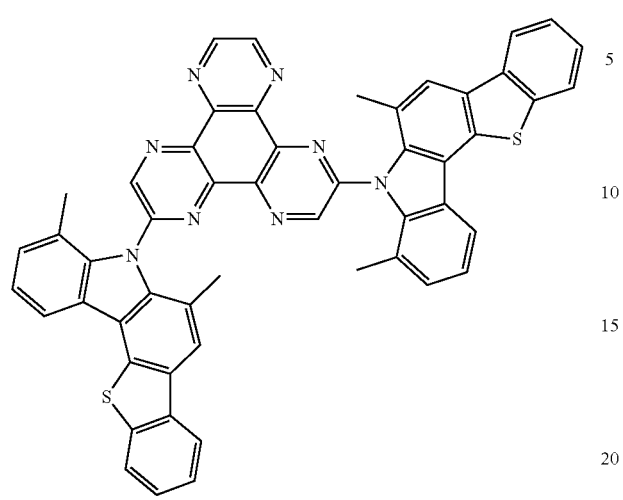
D-8
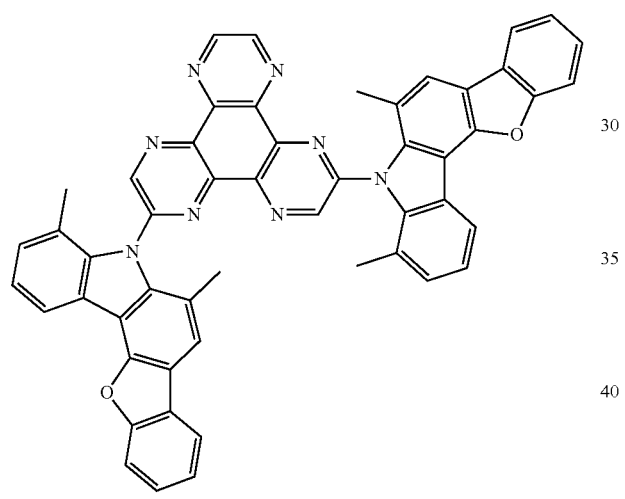
D-9
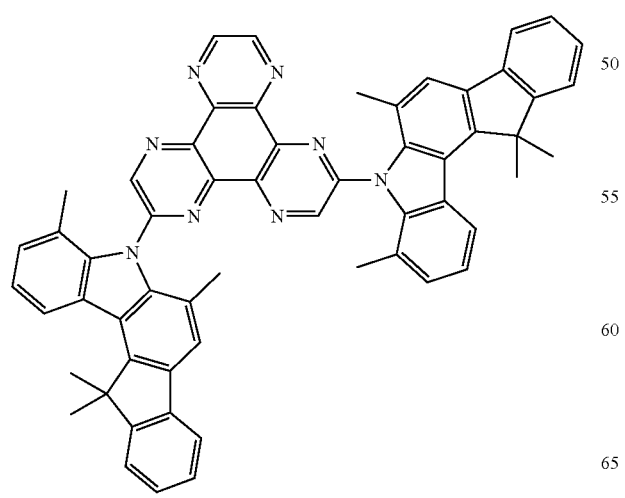
-continued
D-10
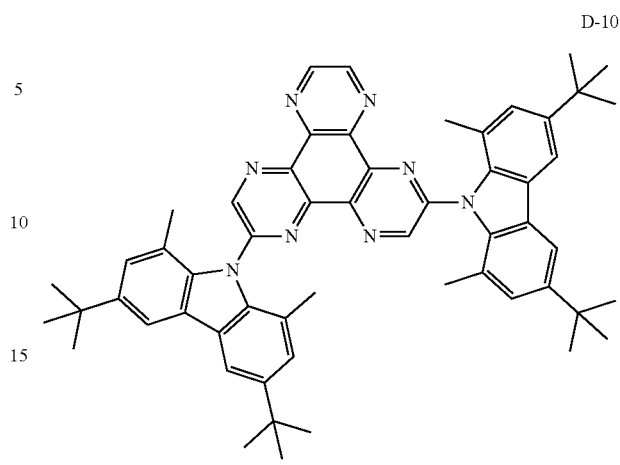
D-11
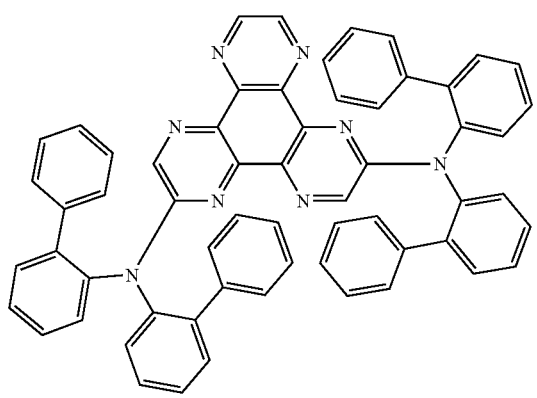
D-12
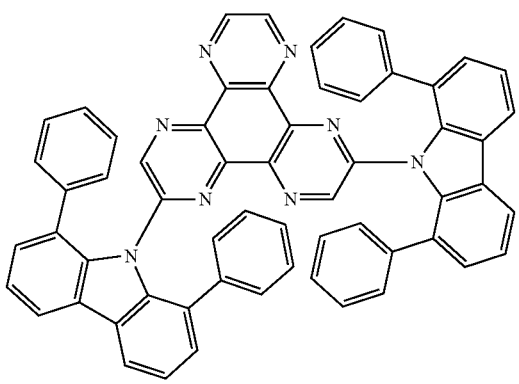

E-1
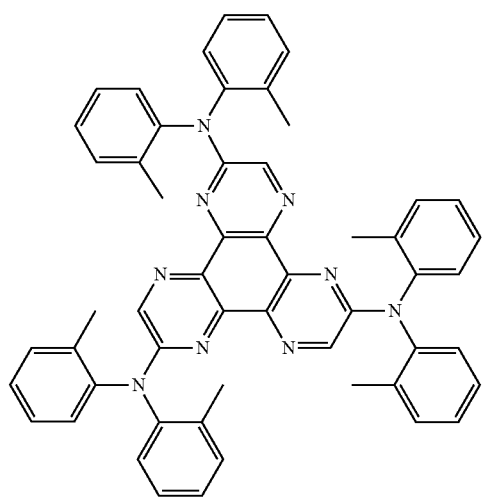
E-2
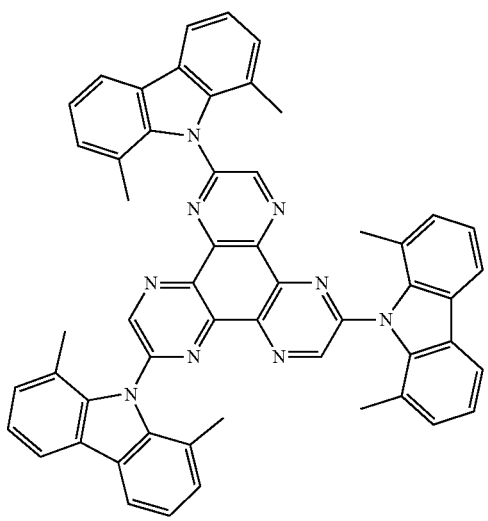
E-3
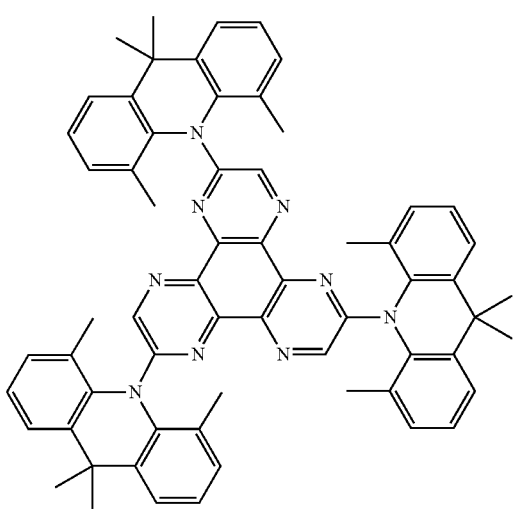
E-4
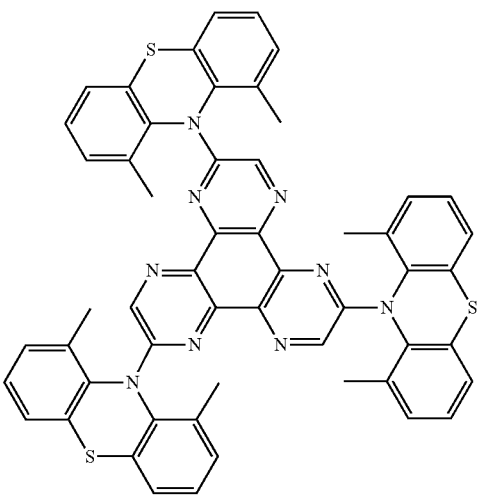
E-5
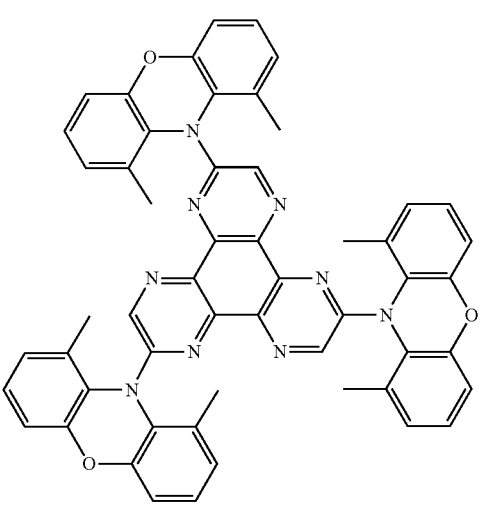
E-6
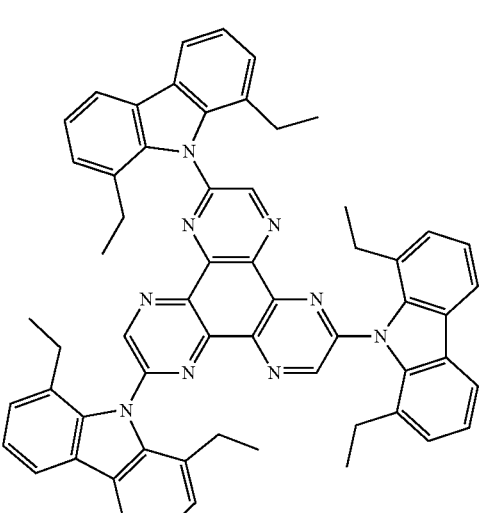

E-7

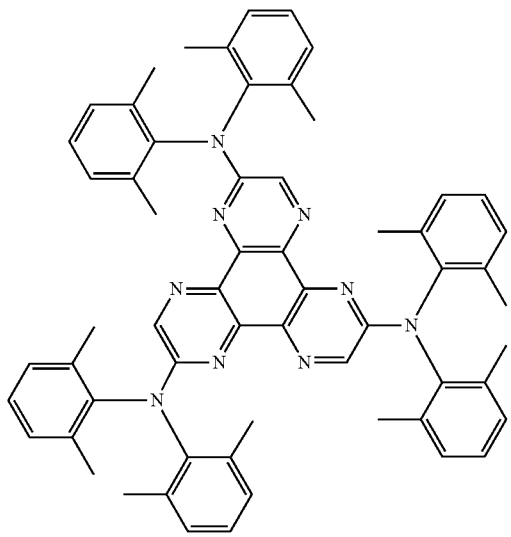

E-8

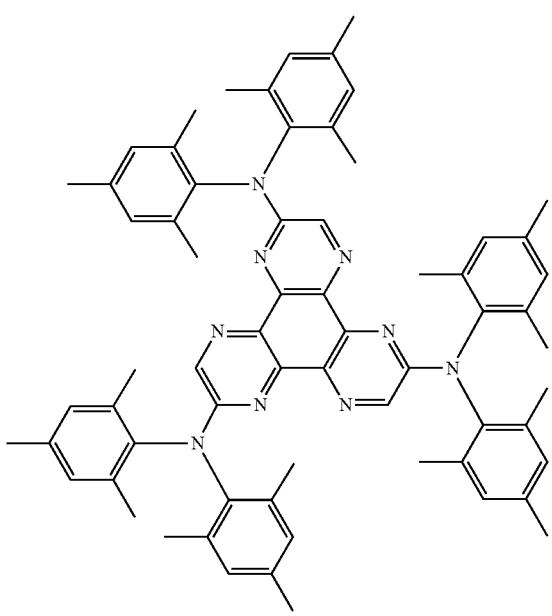

E-9

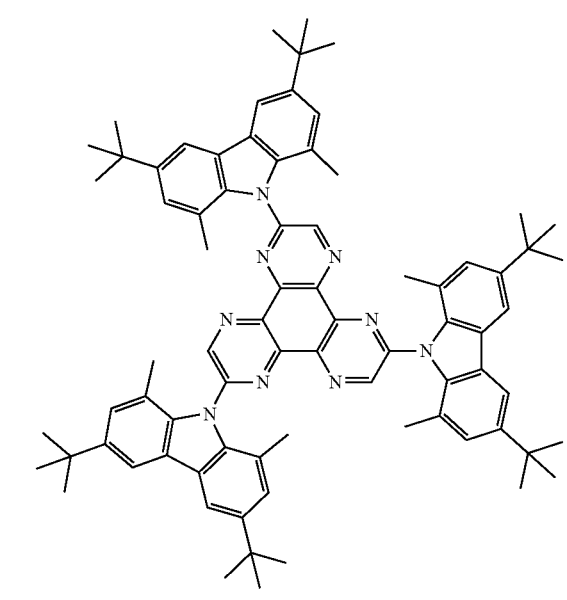

Compounds belonging to group C are monosubstituted compounds (monosubstituted substances) in which among $R_1$ to $R_6$ in each of the compounds represented by formula [1], any one of them is a substituent represented by any of formulae [2] to [18], and all the rest are hydrogen atoms. These compounds are monosubstituted compounds and thus have small $\Delta ST$ ($S_1$-$T_1$ difference) values and easily produce delayed fluorescence. The substituents represented by formulae [2] to [18] are electron-donating substituents. The LUMOs are distributed on the substituents represented by formulae [2] to [18] in the compounds represented by formula [1]. Since each compound belonging to group C is a monosubstituted substance, the number of substituents where the LUMO is distributed is small, and deactivation due to thermal vibration that may occur at the binding site between the basic skeleton and the substituent is reduced; thus, delayed fluorescence is more easily produced.

Compounds belonging to group D are disubstituted compounds (disubstituted substances) in which among $R_1$ to $R_6$ in each of the compounds represented by formula [1], any two of them are substituents each represented by any of formulae [2] to [18], and all the rest are hydrogen atoms. More specifically, each of the compounds may be a compound in which $R_1$ and $R_3$ are substituents each represented by any of formulae [2] to [18], and $R_2$ and $R_4$ to $R_6$ are hydrogen atoms. Each of the compounds contains two substituents and thus has greater steric bulkiness and intermolecular distance than the monosubstituted substances; hence, each compound is less likely to undergo molecular association and less likely to undergo concentration quenching. The AST is as small as those of the monosubstituted compounds; thus, delayed fluorescence is easily produced.

Compounds belonging to group E are trisubstituted compounds (trisubstituted substances) in which among $R_1$ to $R_6$ in each of the compounds represented by formula [1], any three of them are substituents each represented by any of formulae [2] to [18], and all the rest are hydrogen atoms. More specifically, each of the compounds may be a compound in which $R_1$, $R_3$, and $R_5$ are substituents each represented by any of formulae [2] to [18], and $R_2$, $R_4$, and $R_6$ are hydrogen atoms. Each of the compounds contains three substituents and thus has a lower degree of flatness of its molecule, in other words, more steric, than the monosubstituted substances and disubstituted substances. Accordingly, each compound is less likely to undergo molecular association and less likely to undergo concentration quenching, which is more advantageous when used at high concentrations. In addition, the chemical reaction sites of hexaazatriphenylene serving as the basic skeleton are reduced in number and sterically covered with substituents, thus resulting in higher chemical stability. This enables the production of an organic light-emitting element with superior durability.

Organic Light-Emitting Element

The organic light-emitting element according to the embodiment will be described below.

The organic light-emitting element according to the embodiment at least includes an anode and a cathode, which are a pair of electrodes, and an organic compound layer disposed between these electrodes. In the organic light-emitting element according to the embodiment, the organic compound layer may be formed of a single layer or a multilayer stack including multiple layers, as long as it includes a light-emitting layer.

In the case where the organic compound layer is formed of a multilayer stack including multiple layers, the organic compound layer may include, in addition to the light-emitting layer, a hole injection layer, a hole transport layer, an electron-blocking layer, a hole/exciton-blocking layer, an electron transport layer, an electron injection layer, and so forth. The light-emitting layer may be formed of a single layer or a multilayer stack including multiple layers.

In the organic light-emitting element according to the embodiment, at least one organic compound layer contains the organic compound according to the embodiment. Specifically, the organic compound according to the embodiment is contained in any of the light-emitting layer, the hole injection layer, the hole transport layer, the electron-blocking layer, the hole/exciton-blocking layer, the electron transport layer, the electron injection layer, and so forth described above. The organic compound according to the embodiment can be contained in the light-emitting layer. The light-emitting layer can emit green light or red light. The emission color is not limited thereto.

In the organic light-emitting element according to the embodiment, in the case where the organic compound according to the embodiment is contained in the light-emitting layer, the light-emitting layer may consist of only the organic compound according to the embodiment or may be composed of the organic compound according to the embodiment and another compound. In the case where the light-emitting layer is composed of the organic compound according to the embodiment and another compound, the organic compound according to the embodiment may be used as a host material or a guest material for the light-emitting layer. The organic compound may be used as an assist material that can be contained in the light-emitting layer. The term "host material" used here refers to a compound having the highest proportion by mass in compounds constituting the light-emitting layer. The term "guest material" refers to a compound that has a lower proportion by mass than the host material in the compounds constituting the light-emitting layer and that is responsible for main light emission. The term "assist material" refers to a compound that has a lower proportion by mass than the host material in the compounds constituting the light-emitting layer and that assists the light emission of the guest.

In the case where the organic compound according to the embodiment is used as a guest material in the light-emitting layer, the concentration of the organic compound, serving as the guest material, according to the embodiment is preferably 0.01% or more by mass and 20% or less by mass, more preferably 0.1% or more by mass and 5% or less by mass, based on the entire light-emitting layer. In the case where the organic compound according to the embodiment is used as an assist material in the light-emitting layer, the concentration of the organic compound, serving as the assist material, according to the embodiment is preferably 0.1% or more by mass and 45% or less by mass, more preferably 1% or more by mass and 30% or less by mass, based on the entire light-emitting layer.

When the organic compound according to the embodiment is used as the guest material for the light-emitting layer, the ratio by mass of the host material to the organic compound, which is the guest material, according to the embodiment, i.e., (host material/guest material), can be 1.1 or more and 10,000 or less. The above ratio by mass is preferably 2 or more and 1,000 or less, more preferably 2 or more and 100 or less.

In the case where the organic compound according to the embodiment is used as a guest material for the light-emitting layer, a material having a higher LUMO level than the organic compound according to the embodiment (a material having a LUMO level closer to the vacuum level) can be used as a host material. The reason for this is as follows: The organic compound according to the embodiment tends to have a low LUMO level. Thus, when a material having a higher LUMO level than the organic compound according to the embodiment is used as a host material, the organic compound according to the embodiment can receive more electrons supplied to the host material in the light-emitting layer.

When the organic compound according to the embodiment is used as a guest material for the light-emitting layer, the following relationship can be satisfied. Provided that $S_{h1}$ is the energy level of $S_1$ and $T_{h1}$ is the energy level of $T_1$ of the host material, and that $S_{g1}$ is the energy level of $S_1$ and $T_{g1}$ is the energy level of $T_1$ of the guest material, $S_{h1} > S_{g1}$ can be satisfied, and $T_{h1} > T_{g1}$ can be satisfied.

In the case where the organic compound according to the embodiment is used as an assist material in the light-emitting layer, a material having a higher LUMO level than the organic compound according to the embodiment (a material having a LUMO level closer to the vacuum level) can be used as a guest material. The organic compound according to the embodiment tends to have a low LUMO level. Thus, when a material having a higher LUMO level than the organic compound according to the embodiment is used as a light-emitting material (guest material), the organic compound according to the embodiment receives more electrons supplied to the host material of the light-emitting layer, and the assist material is responsible for exciton recombination. This enables efficient energy transfer to the light-emitting material (guest material). In the case where the organic compound according to the embodiment is used as the assist material for the light-emitting layer, a material having a lower $S_1$ energy level than the organic compound according to the embodiment can be used as a guest material (light-emitting material).

The inventors have conducted various studies and have found that when the organic compound according to the embodiment is used as a host material, a guest material, or an assist material for a light-emitting layer, especially as a guest material for a light-emitting layer, a device that emits light with high efficiency and high luminance and that is extremely durable can be provided.

The inventors have further found that when the organic compound according to the embodiment is used as an assist material in the light-emitting layer, a device that emits light with high efficiency and high luminance and that is extremely durable can be provided. The light-emitting layer may be formed of a single layer or multiple layers, and can contain multiple light-emitting materials. The term "multiple layers" may include a state in which the light-emitting layer and another light-emitting layer are stacked, or a state in which an intermediate layer is stacked between multiple light-emitting layers. Tandem devices or stacked devices are also acceptable. In these cases, the emission color of the organic light-emitting element is not limited to a single color. More specifically, the emission color may be white or an intermediate color. The film-forming method is not limited and can be performed by vapor deposition or coating. Details will be described in examples below.

The organic compound according to the embodiment can be used as a constituent material of an organic compound layer other than the light-emitting layer included in the organic light-emitting element according to the embodiment. Specifically, the organic compound may be used as a constituent material of, for example, the electron transport layer, the electron injection layer, the hole transport layer, the hole injection layer, and the hole blocking layer.

Material Contained in Organic Light-Emitting Element

Here, in addition to the organic compound according to the embodiment, various known low-molecular-weight and high-molecular-weight compounds can be used as materials for organic light-emitting elements, as needed. Typically, for example, a hole injection compound or a hole transport compound, a compound to be used as a host material, a light-emitting compound, and an electron injection compound or an electron transport compound can be used together. Examples of these compounds are described below.

As a hole injection-transport material (hole injection material or hole transport material), a material having a high hole mobility can be used so as to facilitate the injection of holes from the anode and to transport the injected holes to the light-emitting layer. To control a deterioration in film quality, such as crystallization, in the organic light-emitting element, a material having a high glass transition temperature can be used. Examples of a low- or high-molecular-weight material having the ability to inject and transport holes include triarylamine derivatives, aryl carbazole derivatives, phenylenediamine derivatives, stilbene derivatives, phthalocyanine derivatives, porphyrin derivatives, poly(vinyl carbazole), polythiophene, and other conductive polymers. Moreover, the hole injection-transport material can be used for the electron-blocking layer.

Non-limiting specific examples of a compound used as the hole injection-transport material will be illustrated below.

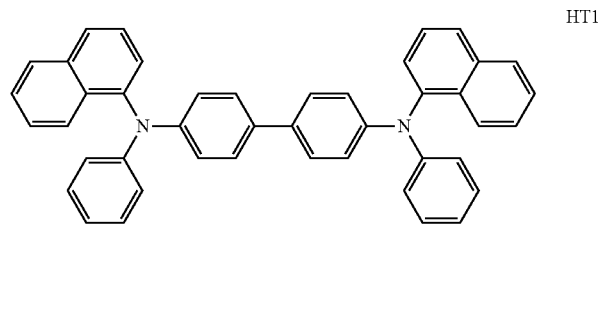

HT1

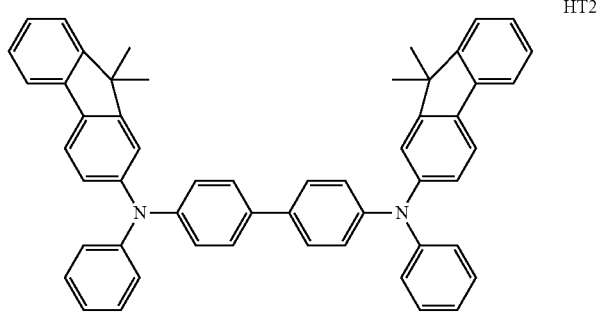

HT2

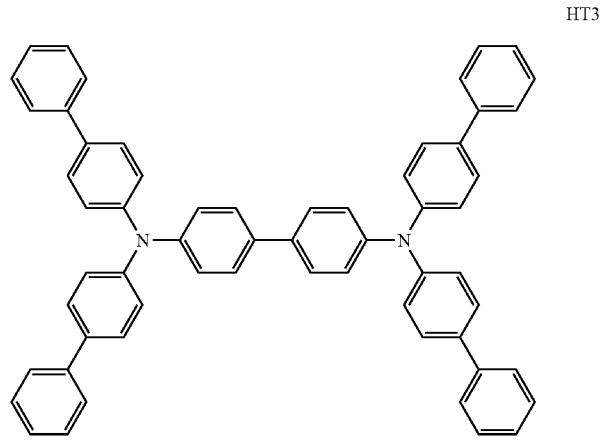

HT3

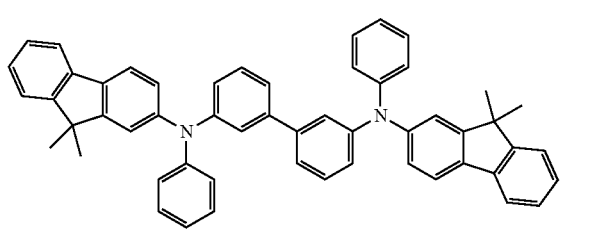

HT4

-continued
HT5
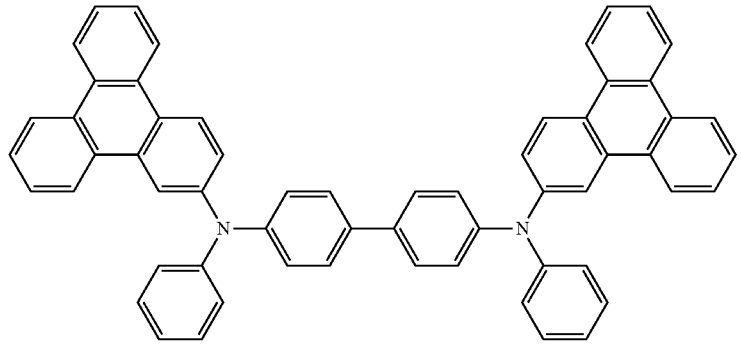
HT6
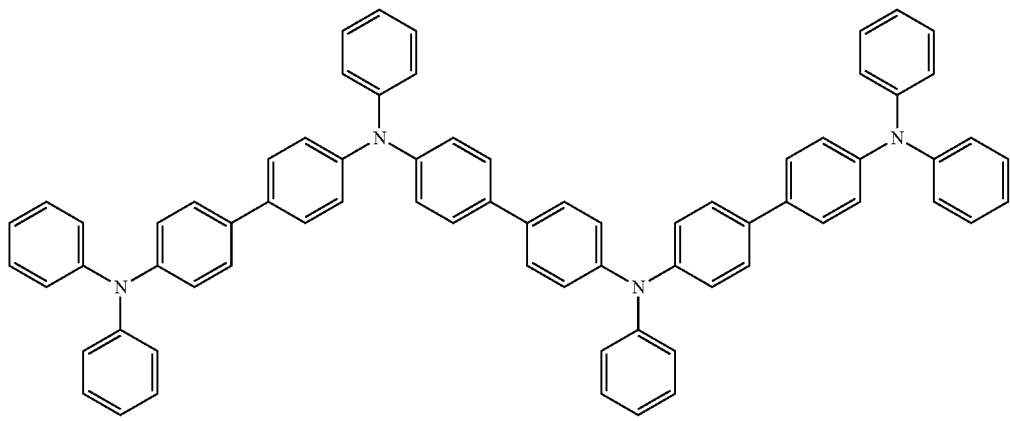
HT7
HT8
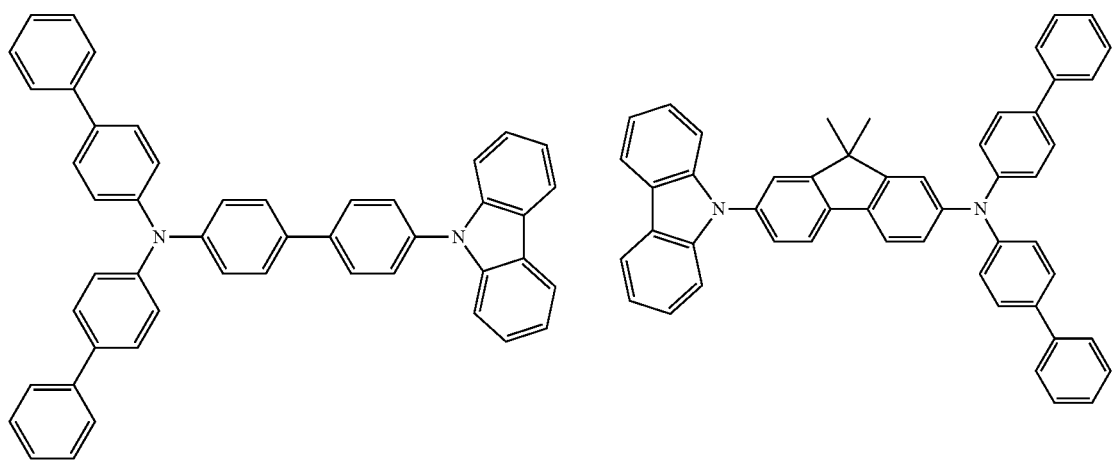
HT9
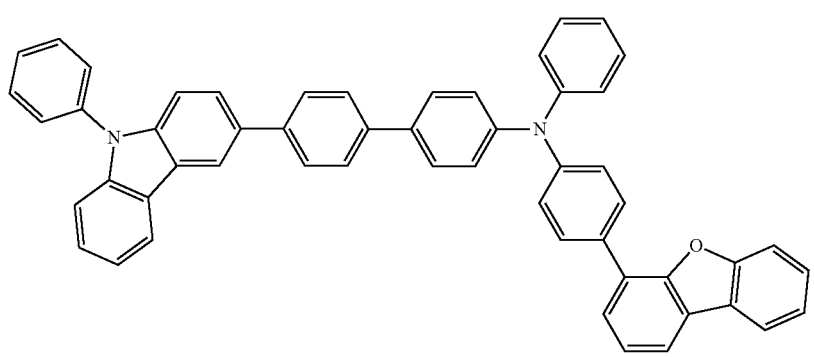

-continued
HT10
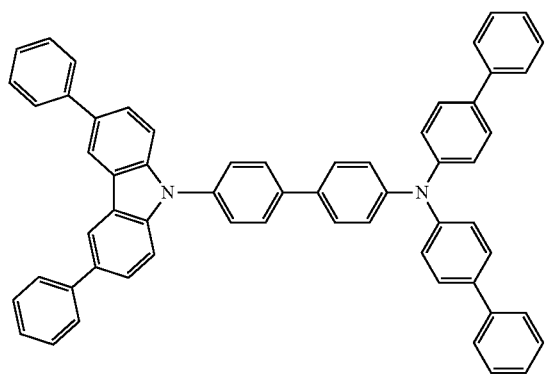
HT11
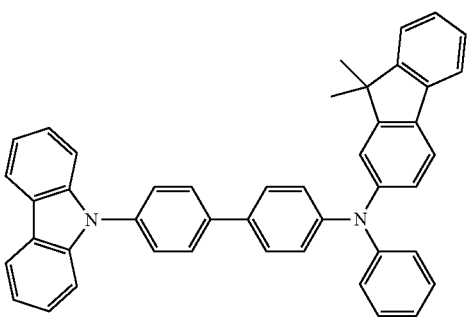
HT12
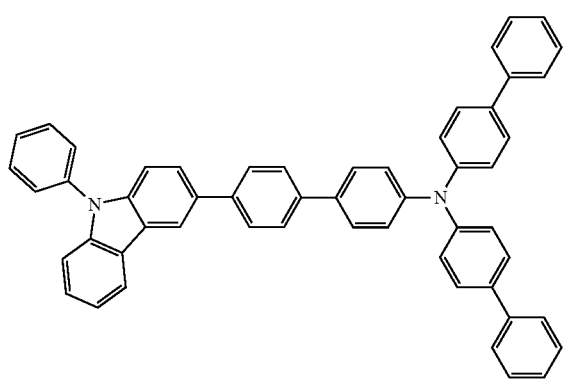
HT13
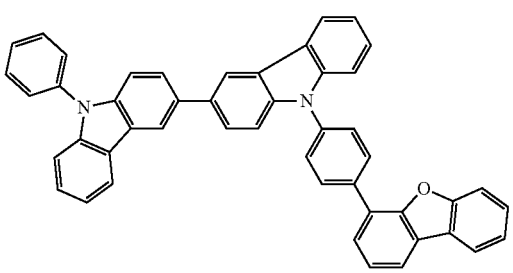
HT14
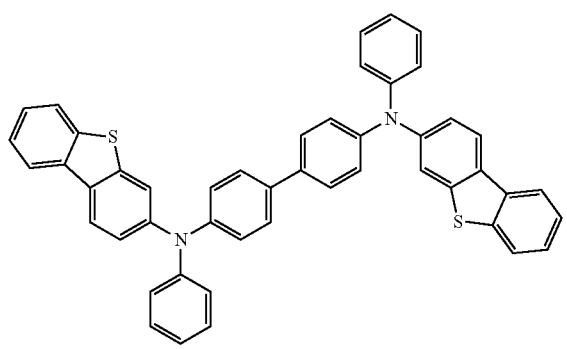
HT15
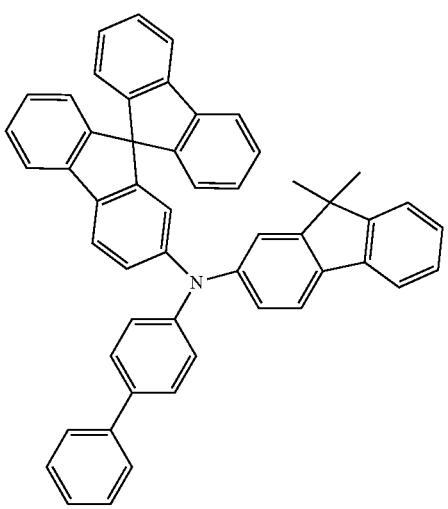
HT16
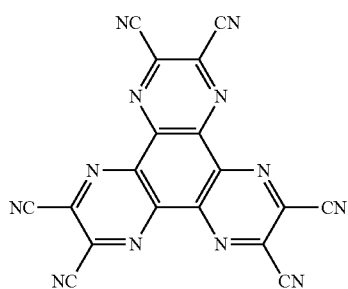
HT17
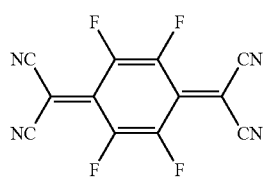

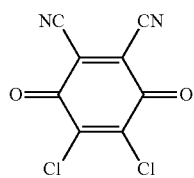
HT18

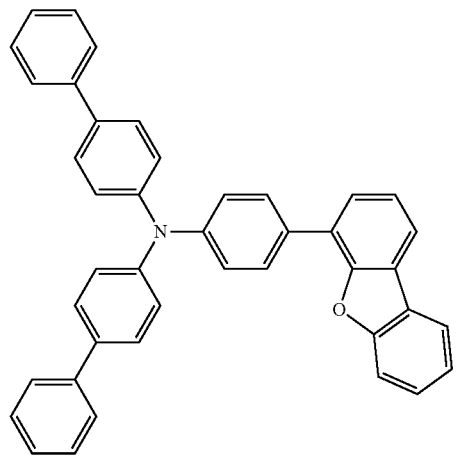
HT19

Among the hole injection-transport materials illustrated above, HT16 to HT18 can be used in the layer in contact with the anode to reduce the driving voltage. HT16 is widely used in organic light-emitting elements. HT2, HT3, HT4, HT5, HT6, HT10, and HT12 may be used in an organic compound layer adjacent to HT16. Multiple materials may be used in a single organic compound layer.

Examples of a light-emitting material mainly associated with a light-emitting function include, in addition to the organic compound represented by formula [1], fused-ring compounds, such as fluorene derivatives, naphthalene derivatives, pyrene derivatives, perylene derivatives, tetracene derivatives, anthracene compounds, and rubrene, quinacridone derivatives, coumarin derivatives, stilbene derivatives, organoaluminum complexes, such as tris(8-quinolinolato)aluminum, iridium complexes, platinum complexes, rhenium complexes, copper complexes, europium complexes, ruthenium complexes, and polymer derivatives, such as poly(phenylene vinylene)derivatives, polyfluorene derivatives, and polyphenylene derivatives.

Non-limiting specific examples of a compound used as a light-emitting material are illustrated below.

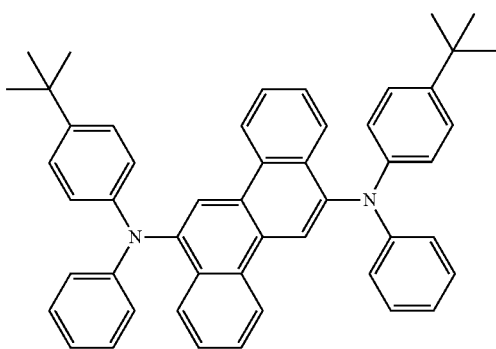
BD1

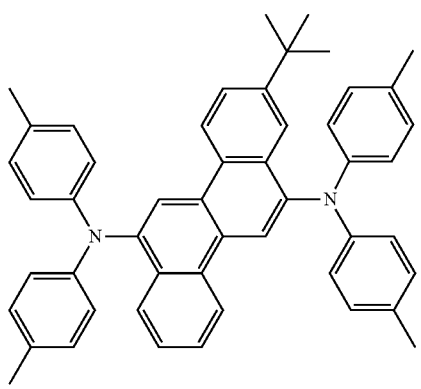
BD2

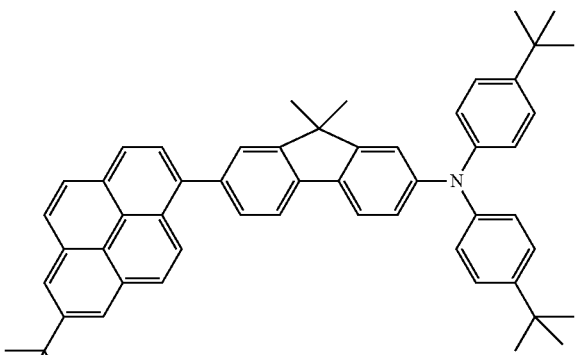
BD3

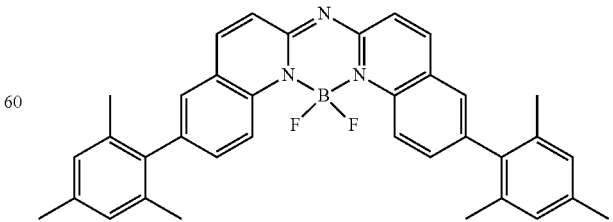
BD4

BD5
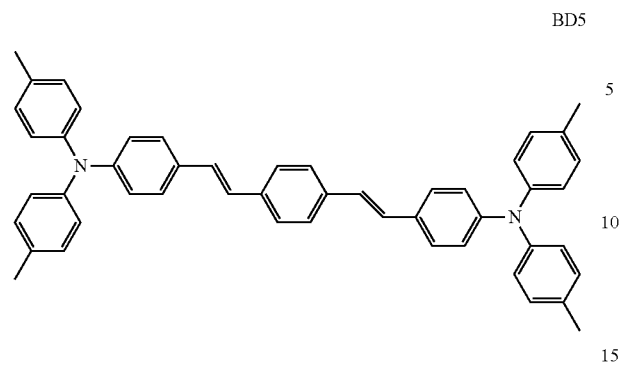
BD9
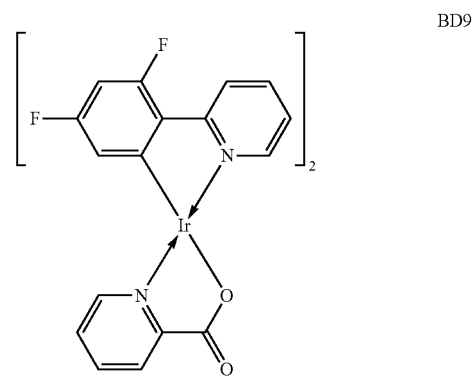
BD6
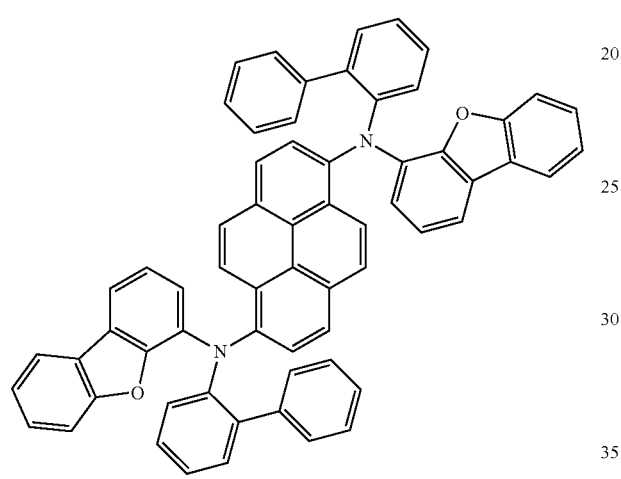
BD10
GD1
BD7
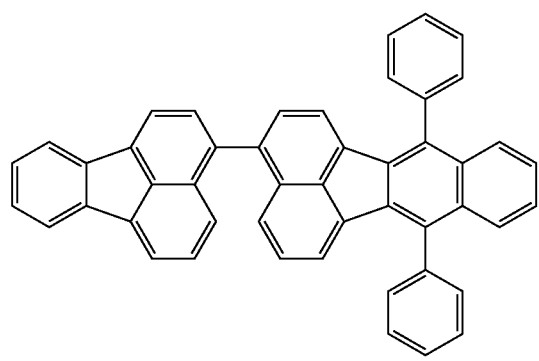
GD2
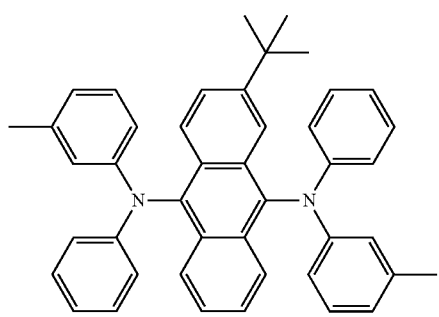
BD8

GD3
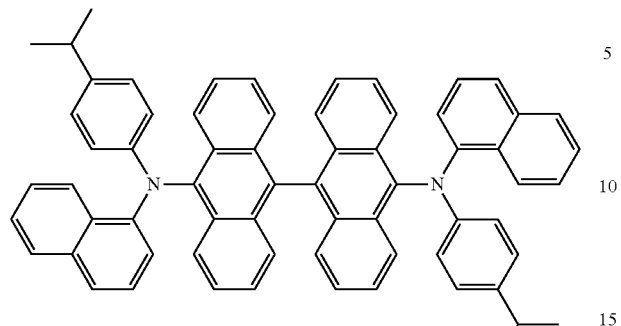
GD4
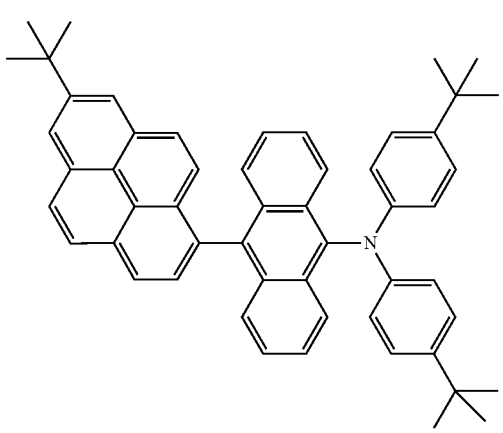
GD5
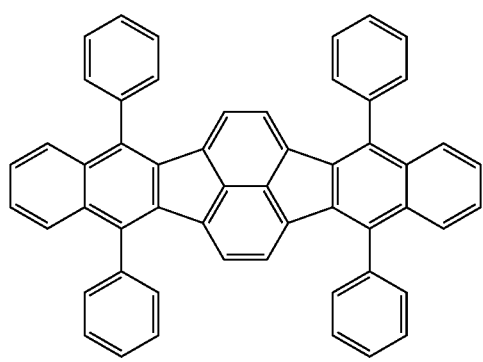
GD6
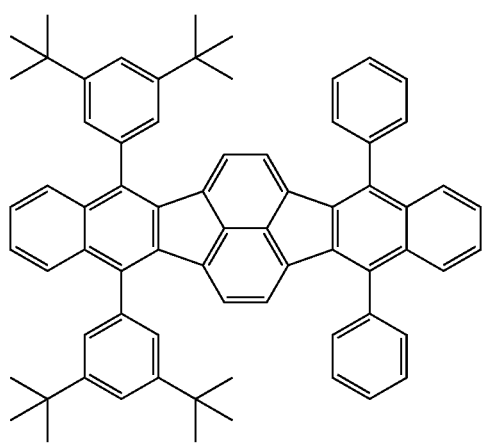
GD7
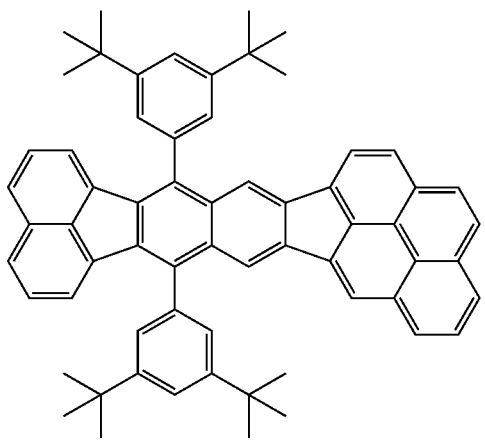
GD8
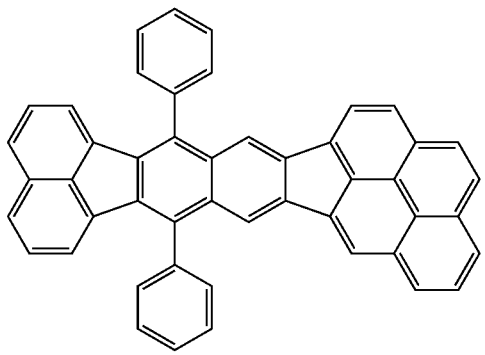
GD9
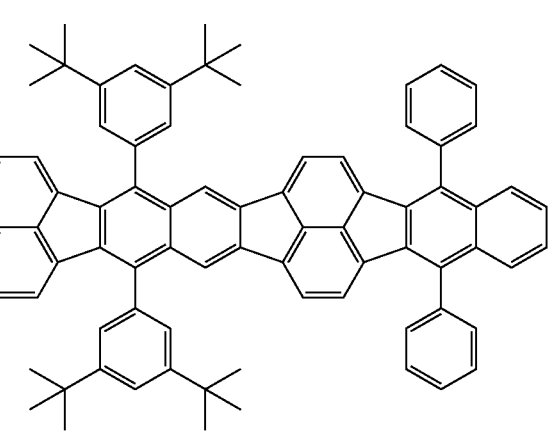
GD10
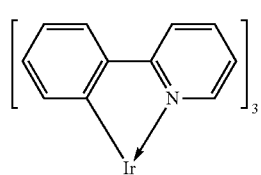

-continued
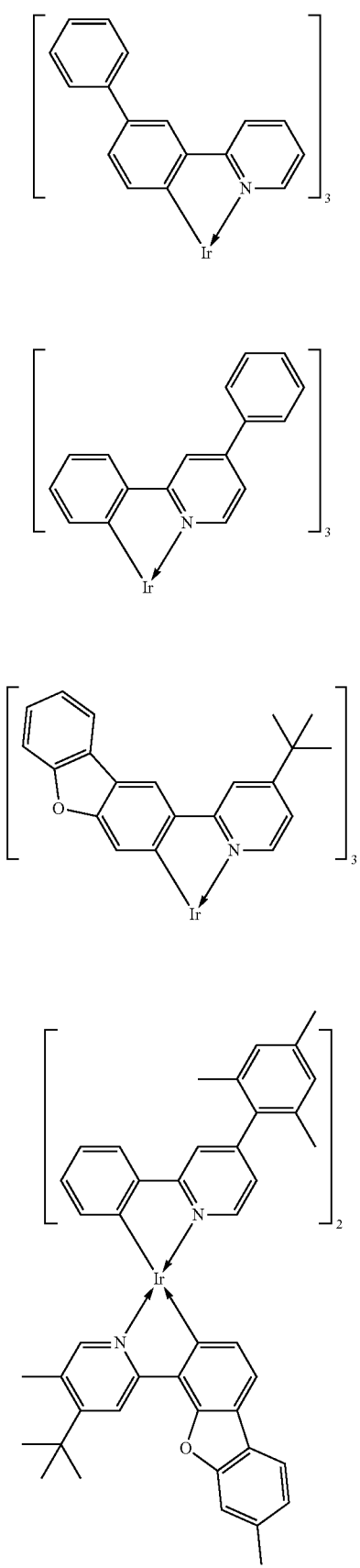
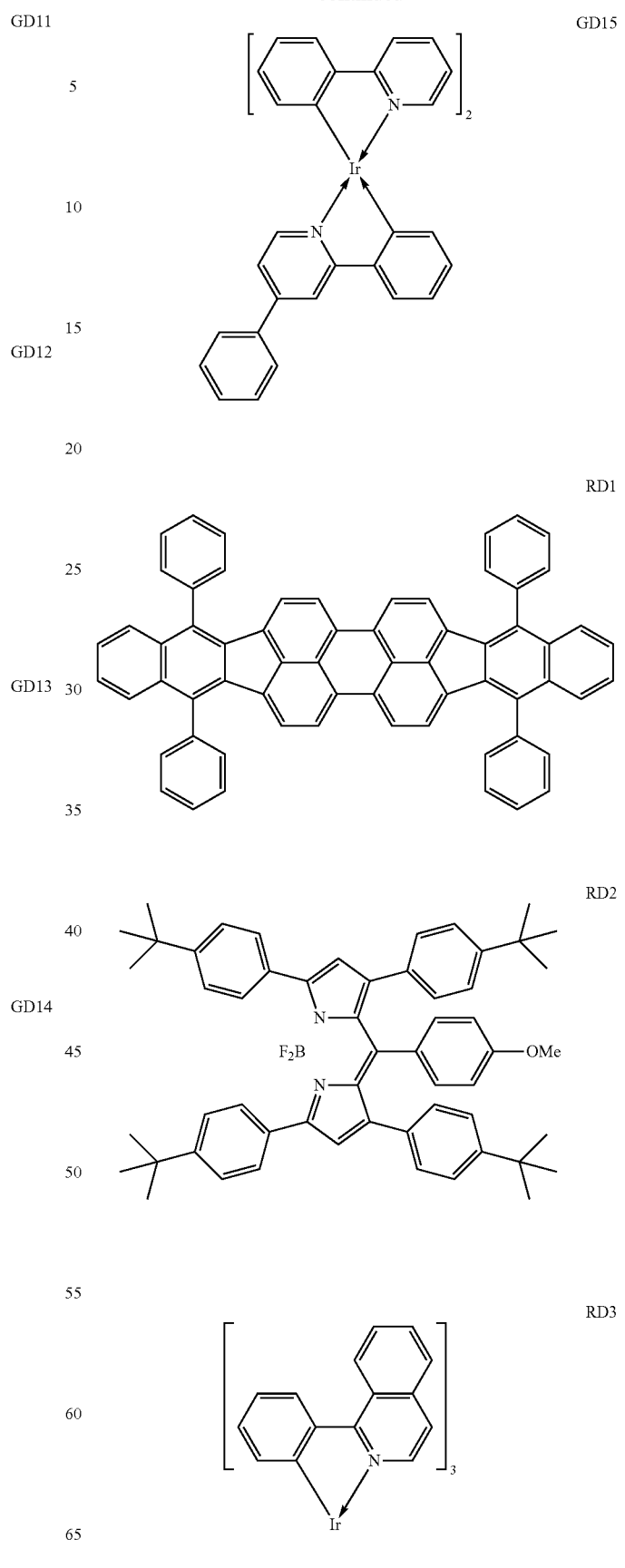

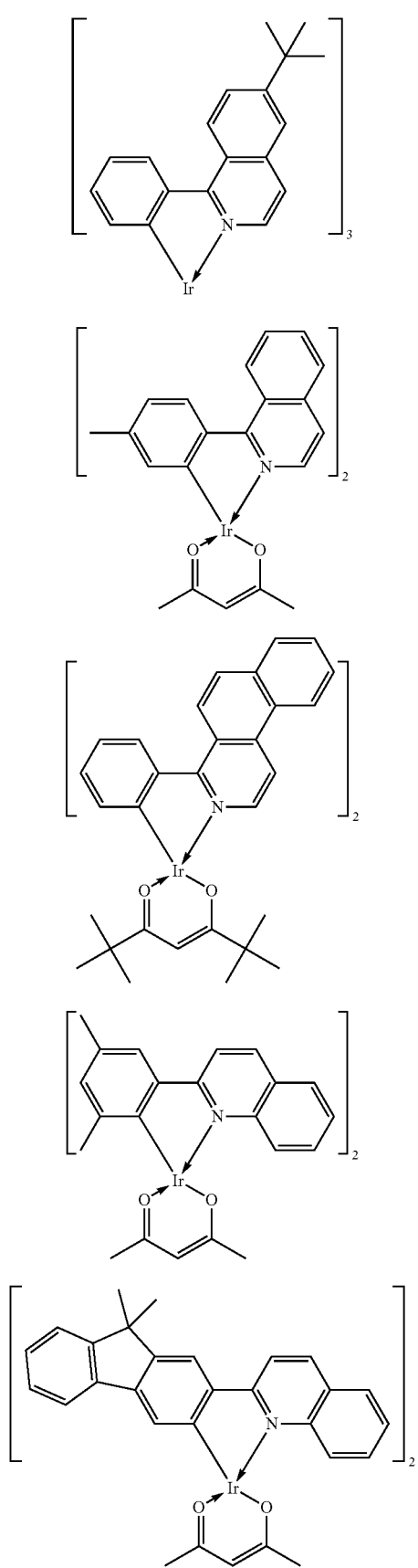

When the light-emitting material is a hydrocarbon compound, the material can prevent a decrease in luminous efficiency due to exciplex formation and a deterioration in color purity due to a change in the emission spectrum of the light-emitting material. The term "hydrocarbon compound" used here refers to a compound consisting of only carbon and hydrogen. Among the specific examples of the compound used as the light-emitting material, BD7, BD8, GD5 to GD9, and RD1 are hydrocarbon compounds.

When the light-emitting material is a fused polycyclic compound containing a five-membered ring, the material has a high ionization potential and high resistance to oxidation. This can provide a highly durable device with a long lifetime. Among the specific examples of the compound used as the light-emitting material, BD7, BD8, GD5 to GD9, and RD1 are each a fused polycyclic compound containing a five-membered ring.

Examples of a host material or an assist material in the light-emitting layer include aromatic hydrocarbon compounds and derivatives thereof, carbazole derivatives, dibenzofuran derivatives, dibenzothiophene derivatives, organoaluminum complexes, such as tris(8-quinolinolato) aluminum, and organoberyllium complexes.

Non-limiting specific examples of a compound used as a host material or an assist material in the light-emitting layer will be illustrated below.

EM1
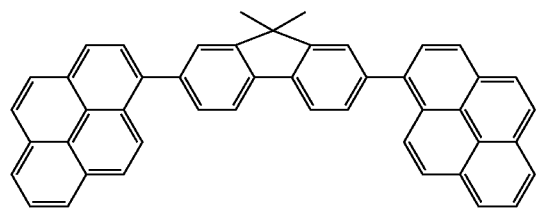
EM2
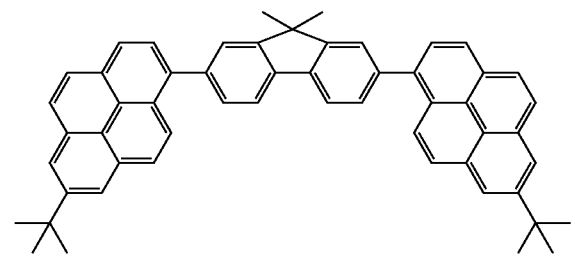
EM3
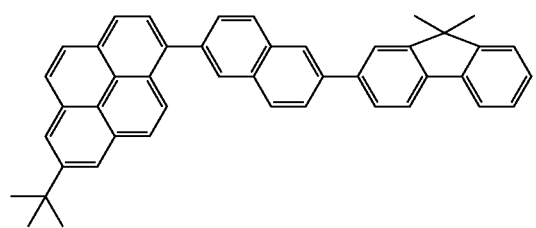
EM4
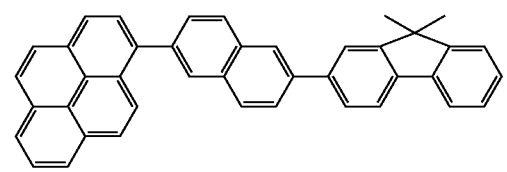
EM5
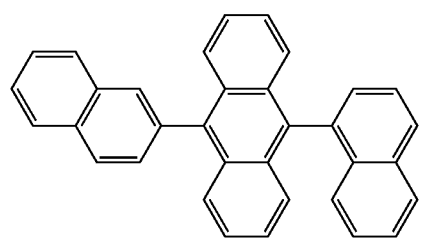
EM6
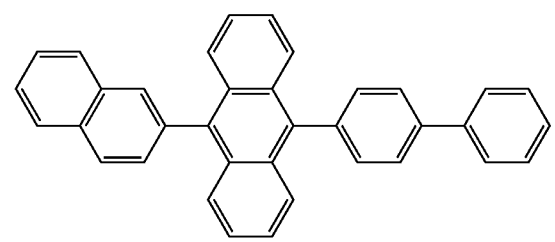
EM7
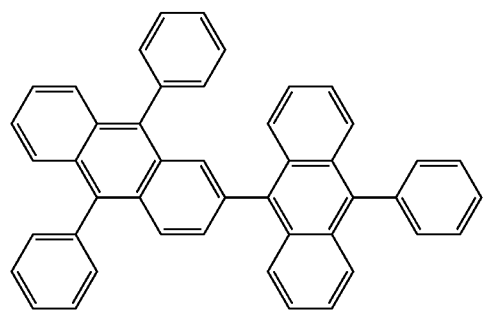
EM8
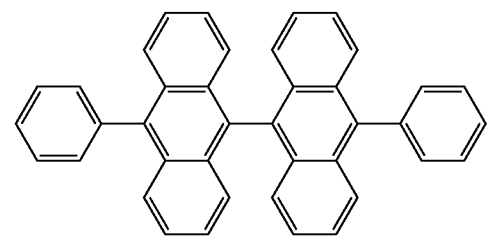
EM9
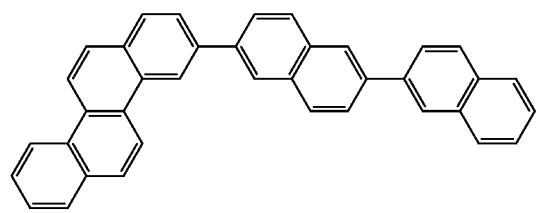
EM10
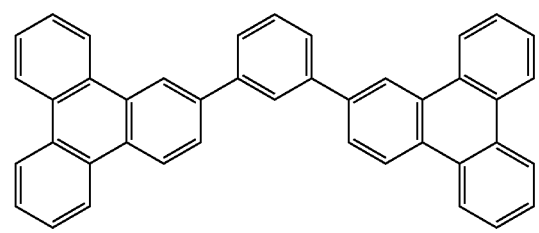
EM11
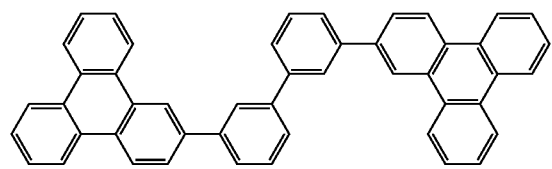
EM12
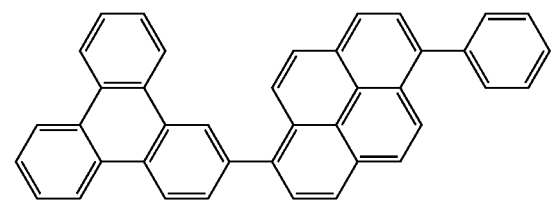

-continued
EM13
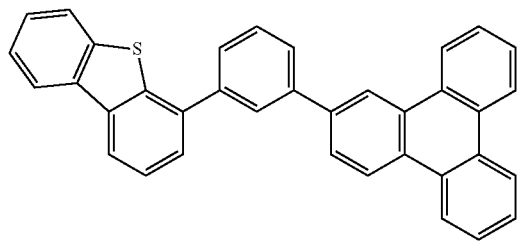
EM14
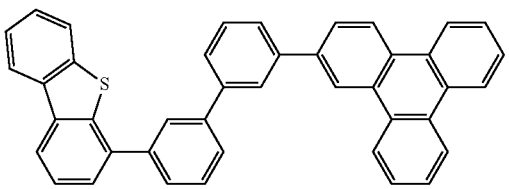
EM15
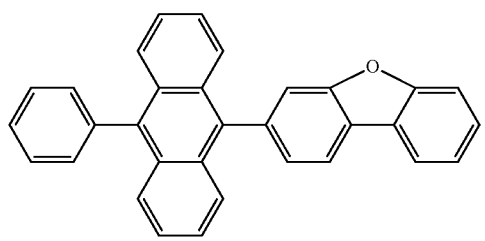
EM16
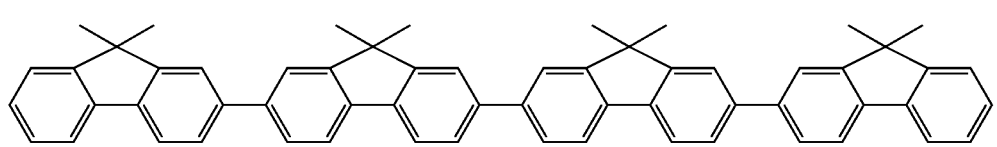
EM17
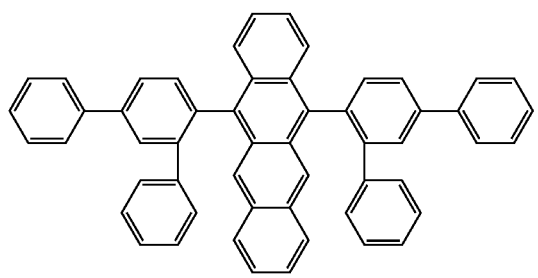
EM18
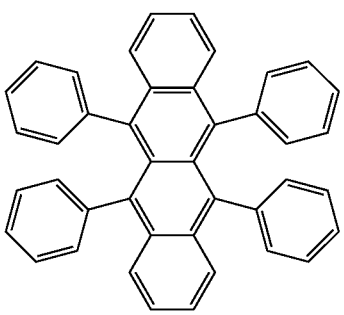
EM19
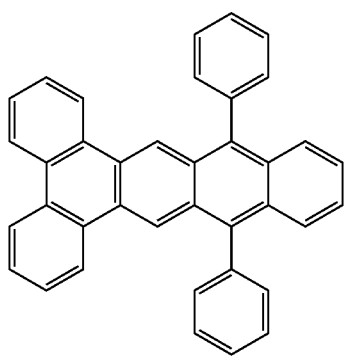
EM20
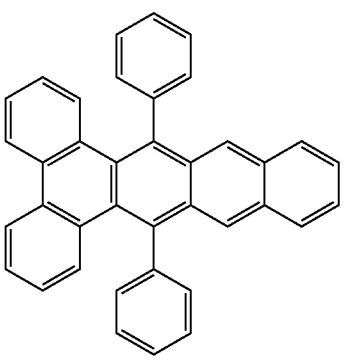

-continued
| | EM21 | | EM22 |
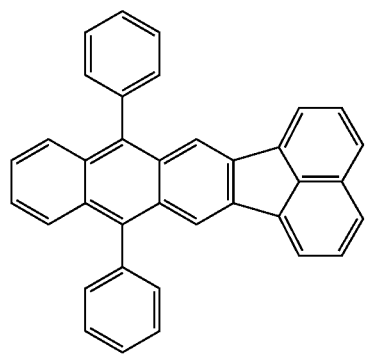
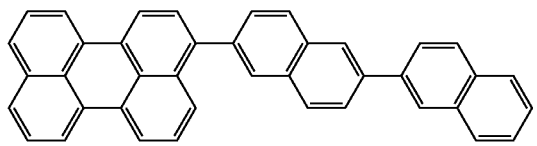
| | EM23 | | EM24 |
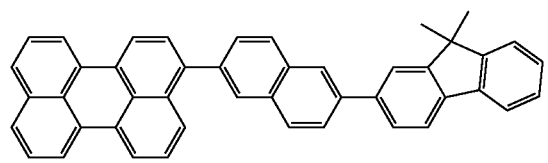
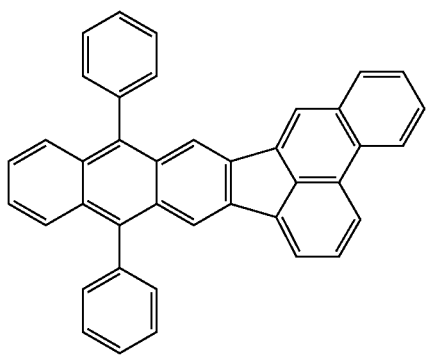
| | | | EM25 |
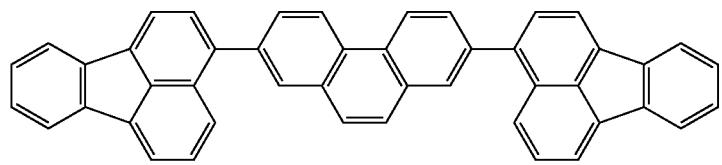
| | | | EM26 |
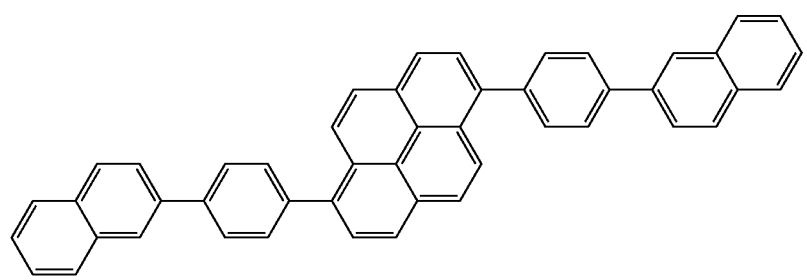
| EM27 | | | EM28 |
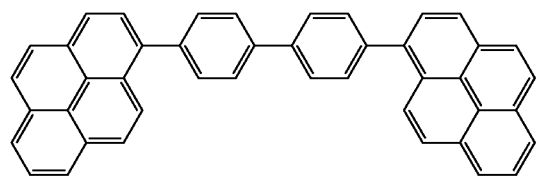
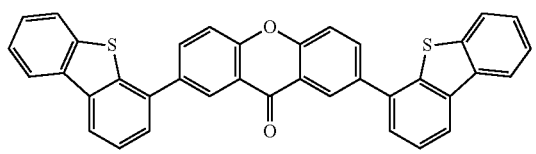

-continued
EM29
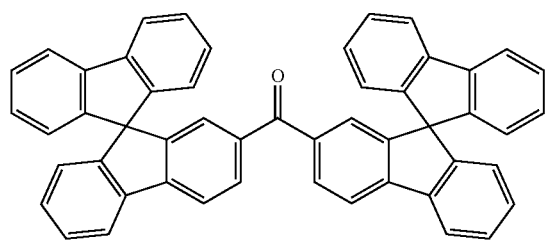
EM30
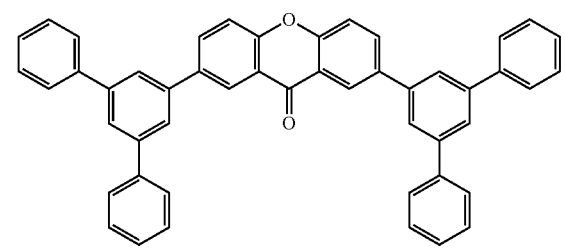
EM31
EM32
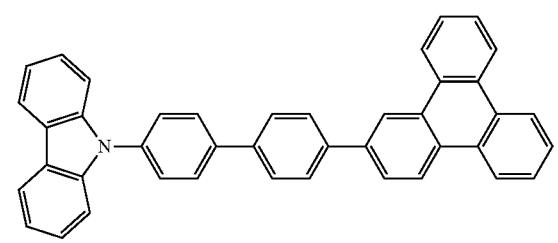
EM33
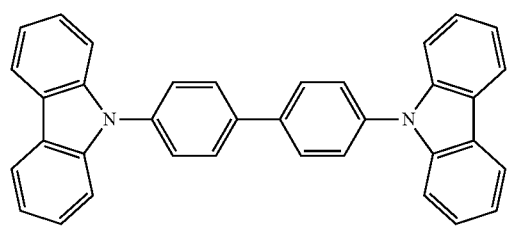
EM34
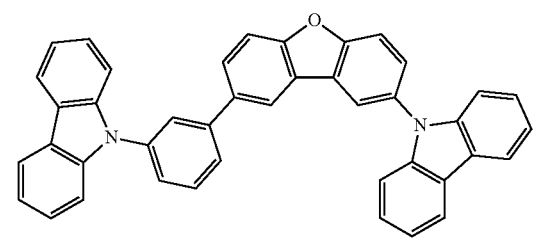
EM35
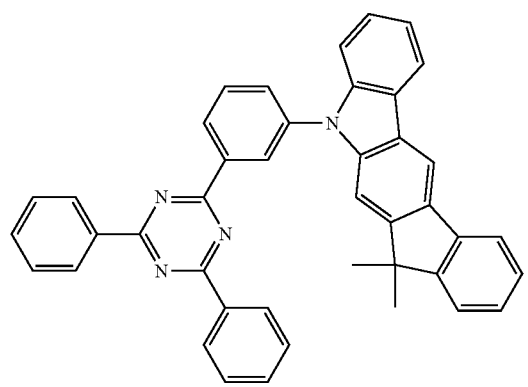
EM36
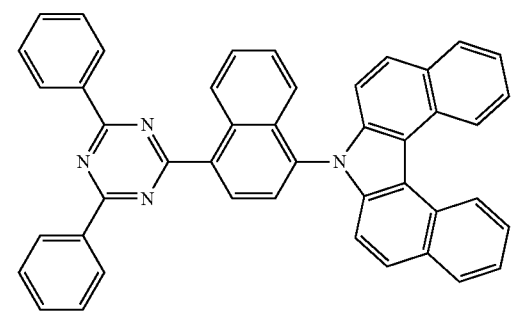
EM37
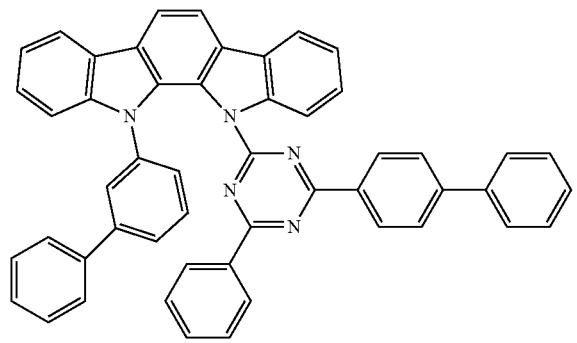
EM38
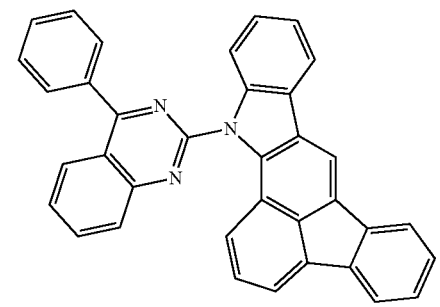

EM39
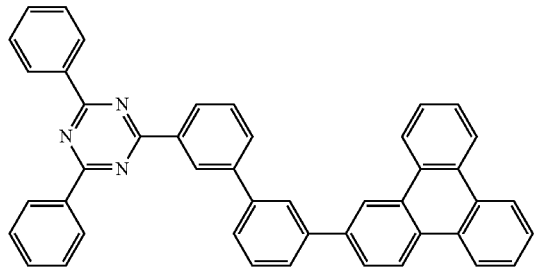

EM40
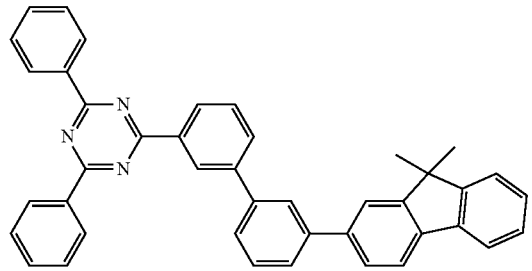

When the host material is a hydrocarbon compound, the compound according to the embodiment of the present disclosure can easily trap electrons and holes to greatly contribute to higher efficiency. The term "hydrocarbon compound" used here refers to a compound consisting of only carbon and hydrogen. Among the specific examples of the compound used as the host material, EM1 to EM12 and EM16 to EM27 are hydrocarbon compounds.

The electron transport material can be freely-selected from materials capable of transporting electrons injected from the cathode to the light-emitting layer and is selected in consideration of, for example, the balance with the hole mobility of the hole transport material. Examples of a material having the ability to transport electrons include oxadiazole derivatives, oxazole derivatives, pyrazine derivatives, triazole derivatives, triazine derivatives, quinoline derivatives, quinoxaline derivatives, phenanthroline derivatives, organoaluminum complexes, and condensed-ring compounds, such as fluorene derivatives, naphthalene derivatives, chrysene derivatives, and anthracene derivatives. The electron transport materials can be used for the hole-blocking layer.

Non-limiting specific examples of a compound used as the electron transport material will be illustrated below.

ET1
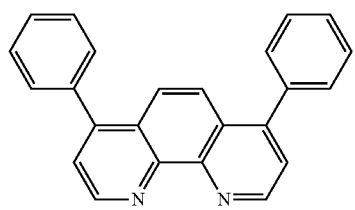

ET2
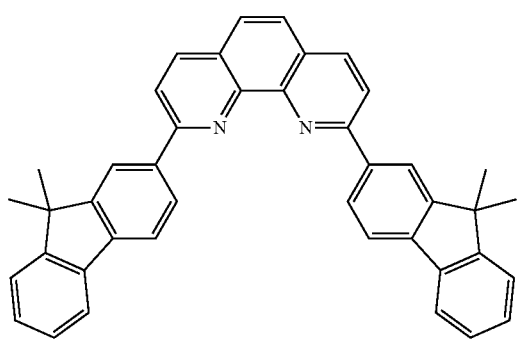

ET3
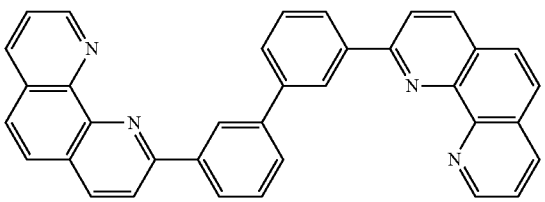

ET4
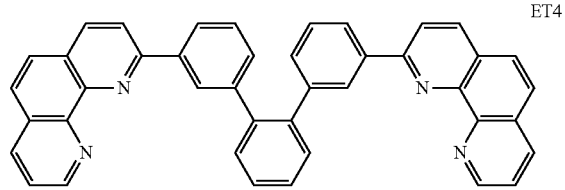

ET5
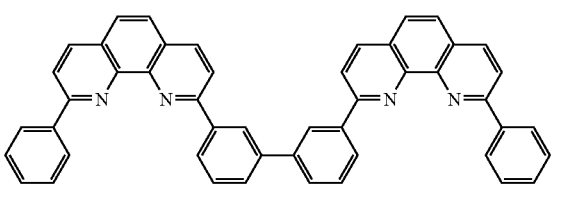

ET6
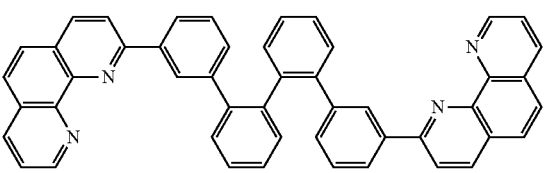

ET7
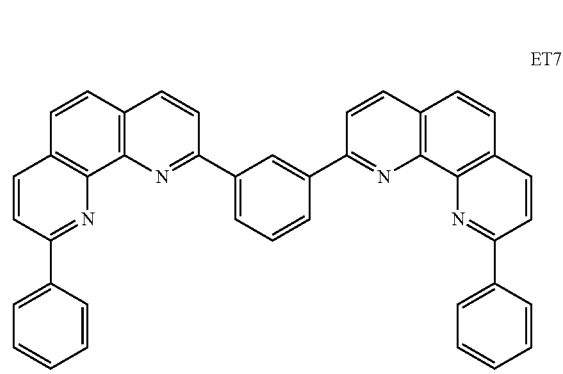

ET8
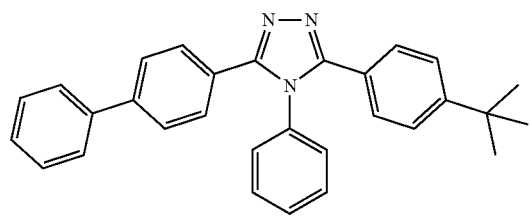
ET9
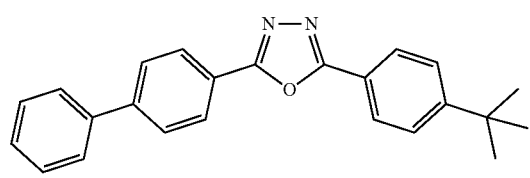
ET10
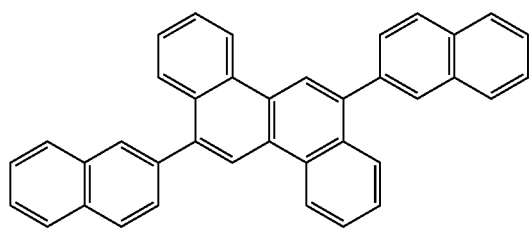
ET11
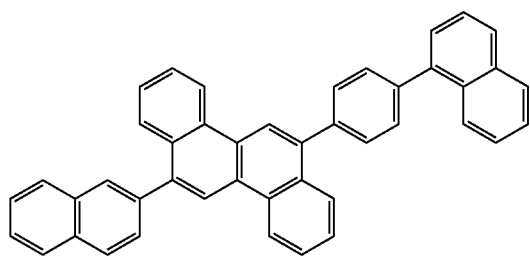
ET12
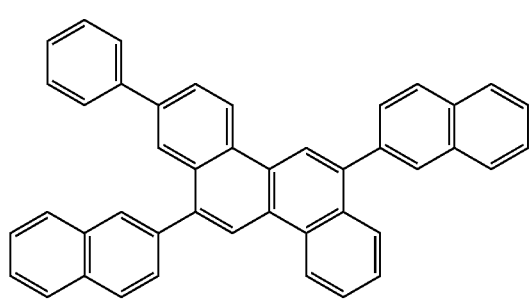
ET13
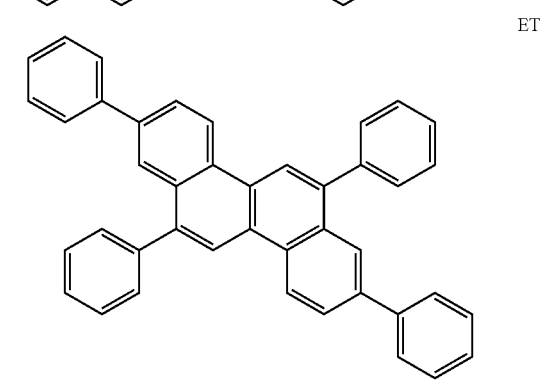
ET14
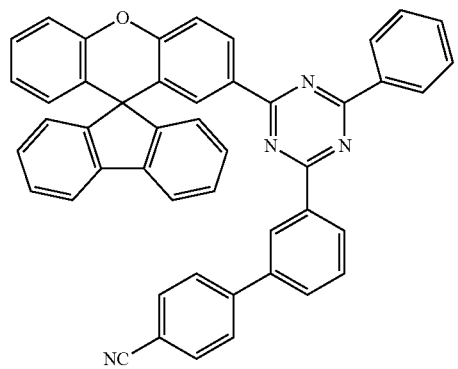
ET15
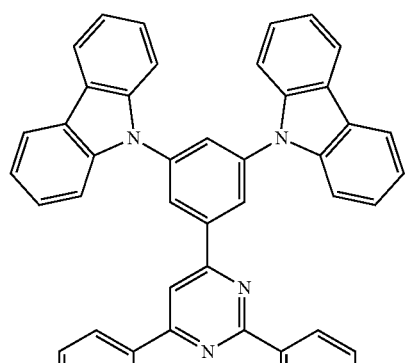
ET16
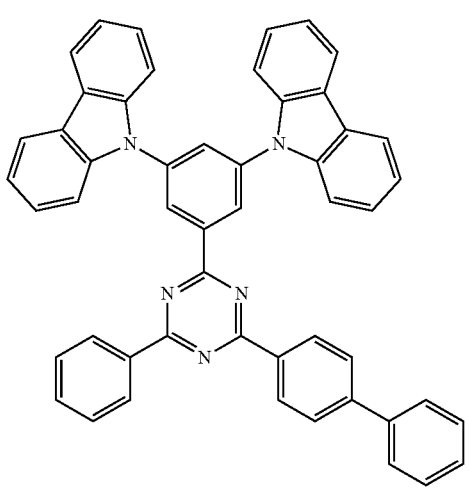
ET17
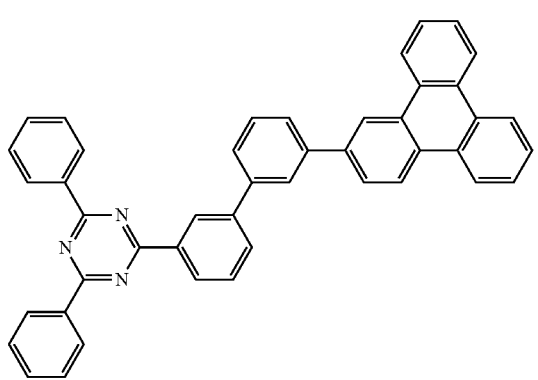

ET18
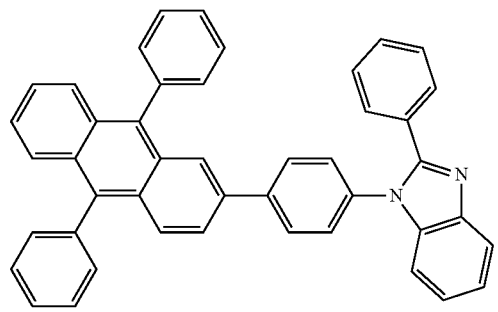
ET19
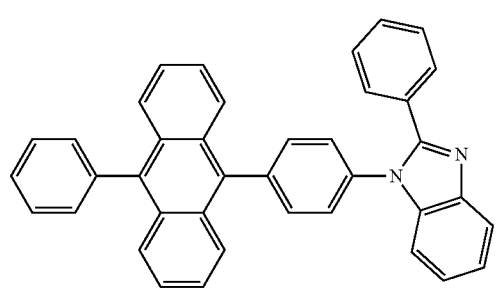
ET20
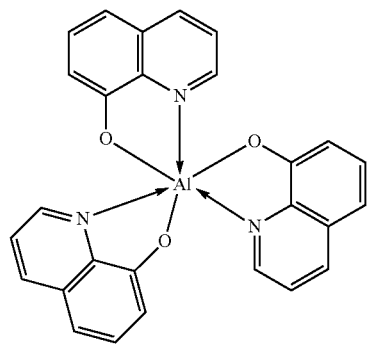
ET21
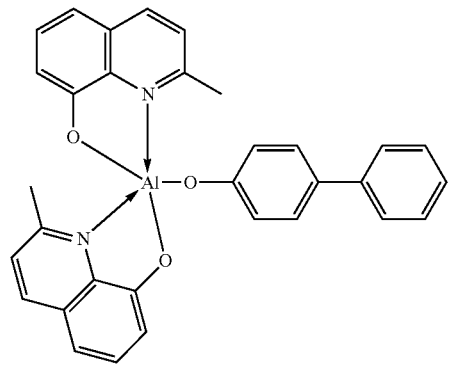
ET22
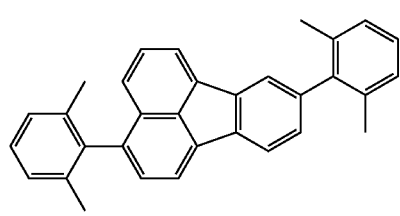
ET23
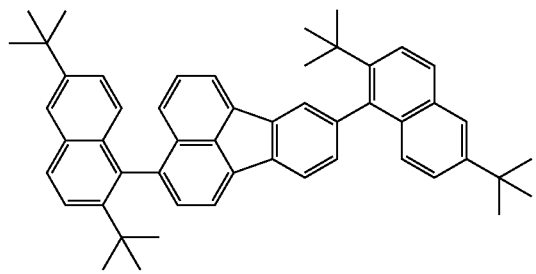
ET24
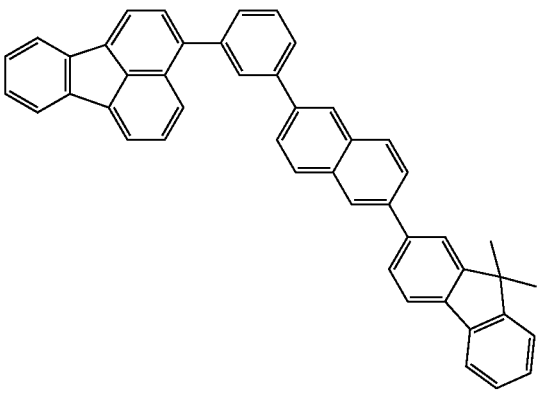
ET25
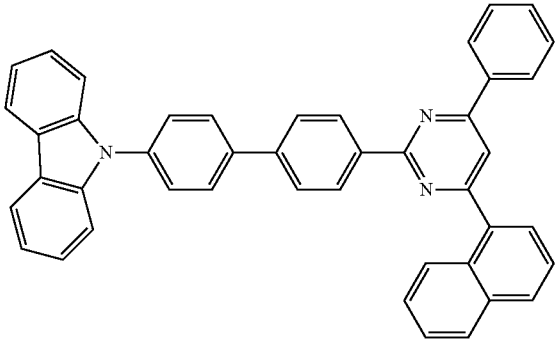

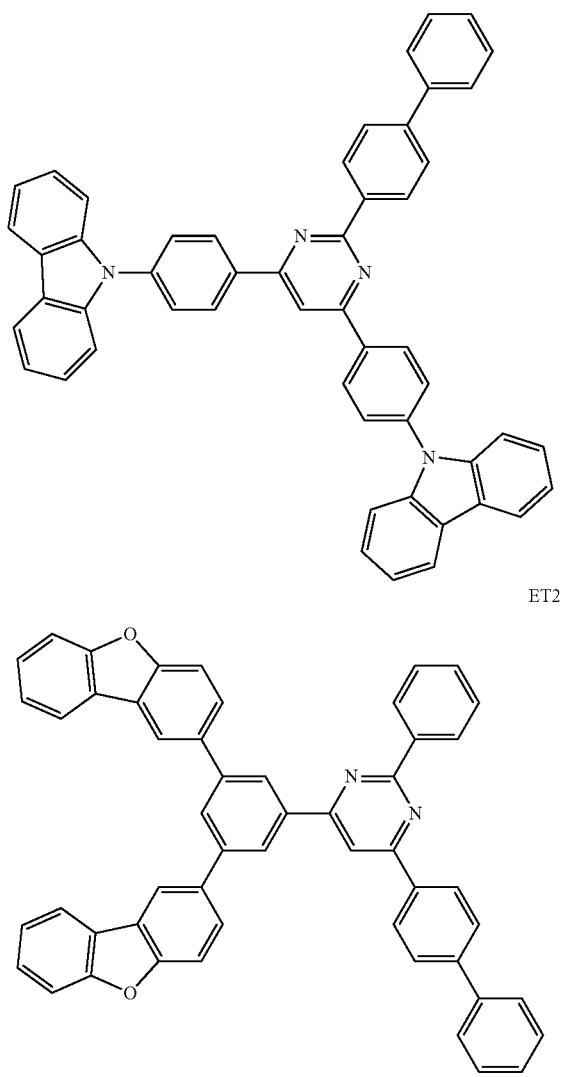

An electron injection material can be freely-selected from materials capable of easily injecting electrons from the cathode and is selected in consideration of, for example, the balance with the hole-injecting properties. As the organic compound, n-type dopants and reducing dopants are also included. Examples thereof include alkali metal-containing compounds, such as lithium fluoride, lithium complexes, such as lithium quinolinolate, benzimidazolidene derivatives, imidazolidene derivatives, fulvalene derivatives, and acridine derivatives.

Configuration of Organic Light-Emitting Element

The organic light-emitting element is provided by disposing an anode, the organic compound layer, and a cathode on a substrate. A protective layer, a color filter, and so forth may be disposed on the cathode. In the case of disposing the color filter, a planarization layer may be disposed between the protective layer and the color filter. The planarization layer can be composed of, for example, an acrylic resin.

Substrate

As the substrate, for example, quartz, glass, a semiconductor substrate, such as a silicon wafer, resin, or metal can be used. The substrate may include switching devices such as a transistor, a line, and an insulating layer thereon. As the insulating layer, any material can be used as long as a contact hole can be formed to establish the electrical connection between the anode and the line and as long as insulation with a non-connected line can be ensured. For example, a resin such as polyimide, silicon oxide, or silicon nitride can be used.

Electrode

A pair of electrodes can be used. The pair of electrodes may be an anode and a cathode.

In the case where an electric field is applied in the direction in which the organic light-emitting element emits light, an electrode having a higher potential is the anode, and the other is the cathode. It can also be said that the electrode that supplies holes to the light-emitting layer is the anode and that the electrode that supplies electrons is the cathode.

As the constituent material of the anode, a material having a work function as high as possible can be used. Examples of the material that can be used include elemental metals, such as gold, platinum, silver, copper, nickel, palladium, cobalt, selenium, vanadium, and tungsten, mixtures thereof, alloys of combinations thereof, and metal oxides, such as tin oxide, zinc oxide, indium oxide, indium-tin oxide (ITO), and indium-zinc oxide. Additionally, conductive polymers, such as polyaniline, polypyrrole, and polythiophene, may be used.

These electrode materials may be used alone or in combination of two or more. The anode may be formed of a single layer or multiple layers.

In the case where the anode is used as a reflective electrode, for example, chromium, aluminum, silver, titanium, tungsten, molybdenum, an alloy thereof, or a stack thereof may be used. In the case where the anode is used as a transparent electrode, a transparent conductive oxide layer composed of, for example, indium-tin oxide (ITO) or indium-zinc oxide may be used; however, the anode is not limited thereto.

The electrode may be formed by photolithography.

As the constituent material of the cathode, a material having a lower work function can be used. Examples thereof include elemental metals such as alkali metals, e.g., lithium, alkaline-earth metals, e.g., calcium, aluminum, titanium, manganese, silver, lead, and chromium, and mixtures thereof. Alloys of combinations of these elemental metals may also be used. For example, magnesium-silver, aluminum-lithium, aluminum-magnesium, silver-copper, and zinc-silver may be used. Metal oxides such as indium-tin oxide (ITO) may also be used. These electrode materials may be used alone or in combination of two or more. The cathode may have a single-layer structure or a multilayer structure. In particular, silver can be used. To suppress the aggregation of silver, a silver alloy can be used. Any alloy ratio may be used as long as the aggregation of silver can be suppressed. For example, 1:1 may be used.

A conductive oxide layer composed of, for example, ITO may be used as the cathode to provide a top-emission organic light-emitting element. A reflective electrode composed of, for example, aluminum (Al) may be used as the cathode to provide a bottom-emission organic light-emitting element. Any method for forming the cathode may be employed. For example, a direct-current or alternatingcurrent sputtering technique can be employed to provide good film coverage and facilitate a reduction in resistance.

Protective Layer

After the formation of the cathode, a protective layer may be provided. For example, a glass member provided with a moisture absorbent can be bonded to the cathode to reduce the entry of, for example, water into the organic compound layer, thereby suppressing the occurrence of display defects. In another embodiment, a passivation film composed of, for example, silicon nitride may be disposed on the cathode to reduce the entry of, for example, water into the organic light-emitting layer. For example, after the formation of the cathode, the substrate may be transported to another chamber without breaking the vacuum, and a silicon nitride film having a thickness of 2 μm may be formed by a chemical vapor deposition (CVD) method to provide a protective layer. After the film deposition by the CVD method, a protective layer may be formed by an atomic layer deposition (ALD) method.

Color Filter

A color filter may be disposed on the protective layer. For example, a color filter that matches the size of the organic light-emitting element may be disposed on another substrate and bonded to the substrate provided with the organic light-emitting element. A color filter may be formed by patterning on the protective layer composed of, for example, silicon oxide using photolithography. The color filter may be composed of a polymer.

Planarization Layer

A planarization layer may be disposed between the color filter and the protective layer. The planarization layer may be composed of an organic compound. A low- or high-molecular-weight organic compound may be used. A high-molecular-weight organic compound can be used.

The planarization layer may be provided on each of the top and bottom of the color filter. In this case, the planarization layers may be composed of the same material or different materials. Specific examples thereof include poly (vinyl carbazole) resins, polycarbonate resins, polyester resins, acrylonitrile butadiene styrene (ABS) resins, acrylic resins, polyimide resins, phenolic resins, epoxy resins, silicone resins, and urea resins.

Opposite Substrate

An opposite substrate may be disposed on the planarization layer. The opposite substrate is disposed at a position corresponding to the substrate described above and thus is called an opposite substrate. The opposite substrate may be composed of the same material as the substrate described above.

Organic Layer

The organic compound layer, such as the hole injection layer, the hole transport layer, the electron-blocking layer, the light-emitting layer, the hole-blocking layer, the electron transport layer, or the electron injection layer, included in the organic light-emitting element according to an embodiment of the present disclosure is formed by a method described below.

For the organic compound layer included in the organic light-emitting element according to an embodiment of the present disclosure, a dry process, such as a vacuum evaporation method, an ionized evaporation method, sputtering, or plasma, may be employed. Alternatively, instead of the dry process, it is also possible to employ a wet process in which a material is dissolved in an appropriate solvent and then a film is formed by a known coating method, such as spin coating, dipping, a casting method, a Langmuir-Blodgett (LB) technique, or an ink jet method.

In the case where the layer is formed by, for example, the vacuum evaporation method or the solution coating method, crystallization and so forth are less likely to occur, and good stability with time is obtained. In the case of forming a film by the coating method, the film may be formed in combination with an appropriate binder resin.

Non-limiting examples of the binder resin include poly (vinyl carbazole) resins, polycarbonate resins, polyester resins, acrylonitrile butadiene styrene (ABS) resins, acrylic resins, polyimide resins, phenolic resins, epoxy resins, silicone resins, and urea resins.

These binder resins may be used alone as a homopolymer or copolymer or in combination as a mixture of two or more. Furthermore, additives, such as a known plasticizer, antioxidant, and ultraviolet absorber, may be used, as needed.

Application of Organic Light-Emitting Element According to Embodiment of the Present Disclosure The organic light-emitting element according to an embodiment can be used as component member of a display apparatus or a lighting device. Other applications include exposure light sources for electrophotographic image-forming apparatuses, backlights for liquid crystal displays, and light-emitting apparatuses including white light sources and color filters.

The display apparatus may be an image information-processing unit having an image input unit that receives image information from an area or linear CCD sensor, a memory card, or any other source, an information-processing unit that processes the input information, and a display unit that displays the input image. The display apparatus includes multiple pixels, and at least one of the multiple pixels may include the organic light-emitting element according to the embodiment and a transistor coupled to the organic light-emitting element. In this case, the substrate may be a semiconductor substrate composed of, for example silicon, and the transistor may be a MOSFET formed on or at the substrate.

The display unit of an image pickup apparatus or an inkjet printer may have a touch panel function. The driving mode of the touch panel function may be, but is not limited to, an infrared mode, an electrostatic capacitance mode, a resistive film mode, or an electromagnetic inductive mode. The display apparatus may also be used for a display unit of a multifunction printer.

The following describes a display apparatus according to the embodiment with reference to the attached drawings. FIG. 1 is a schematic cross-sectional view of an example of a display apparatus including organic light-emitting elements and thin-film transistor (TFT) devices coupled to the respective organic light-emitting elements. Each of the TFT devices is an example of active devices.

A display apparatus 1 illustrated in FIG. 1 includes a substrate 11 composed of, for example, glass and a moisture-proof film 12 disposed thereon, the moisture-proof film 12 being configured to protect the TFT devices or the organic compound layers. A gate electrode 13 composed of a metal, a gate insulating film 14, and a semiconductor layer 15 are disposed on the moisture-proof film 12.

TFT devices 18 each include the semiconductor layer 15, a drain electrode 16, and a source electrode 17. An insulating film 19 is disposed on the TFT devices 18. An anode 21 included in an organic light-emitting element is coupled to the source electrode 17 through a contact hole 20.

The way of electric coupling between the electrodes (the anode 21 and a cathode 23) included in each of the organic light-emitting elements and the electrodes (the source electrode 17 and the drain electrode 16) included in a corresponding one of the TFT devices is not limited to the configuration illustrated in FIG. 1. It is sufficient that one of the anode 21 and the cathode 23 is electrically coupled to one of the source electrode 17 and the drain electrode 16 of the TFT device 18.

In the display apparatus 1 illustrated in FIG. 1, each organic compound layer 22 is illustrated as a single layer; however, the organic compound layer 22 may be formed of multiple layers. A first protective layer 25 and a second protective layer 24 are disposed on the cathodes 23 in order to suppress the deterioration of the organic light-emitting elements.

In the display apparatus 1 illustrated in FIG. 1, the transistors are used as switching devices; however, metal-insulator-metal (MIM) devices may be used as switching devices.

The transistors used in the display apparatus 1 illustrated in FIG. 1 are not limited to thin-film transistors each having an active layer on the insulating surface of a substrate and may be transistors formed using a single-crystal silicon wafer.

Examples of the material of the active layer include single-crystal silicon, non-single-crystal silicon materials, such as amorphous silicon and microcrystalline silicon, and non-single-crystal oxide semiconductors, such as indium-zinc oxide and indium-gallium-zinc oxide. Thin-film transistors are also referred to as TFT devices.

The transistors in the display apparatus 1 illustrated in FIG. 1 may be formed in the substrate such as a Si substrate. The expression "formed in the substrate" indicates that the transistors are produced by processing the substrate such as a Si substrate. In the case where the transistors are formed in the substrate, the substrate and the transistors can be deemed to be integrally formed.

In the organic light-emitting element according to the embodiment, the luminance is controlled by the TFT devices, which are an example of switching devices; thus, an image can be displayed at respective luminance levels by arranging multiple organic light-emitting elements in the plane. The switching devices according to the embodiment are not limited to the TFT devices and may be low-temperature polysilicon transistors or active-matrix drivers formed on a substrate such as a Si substrate. The expression "on a substrate" can also be said to be "in the substrate". Whether transistors are formed in the substrate or TFT devices are used is selected in accordance with the size of a display unit. For example, in the case where the display unit has a size of about 0.5 inches, organic light-emitting elements can be disposed on a Si substrate.

Figure 2:
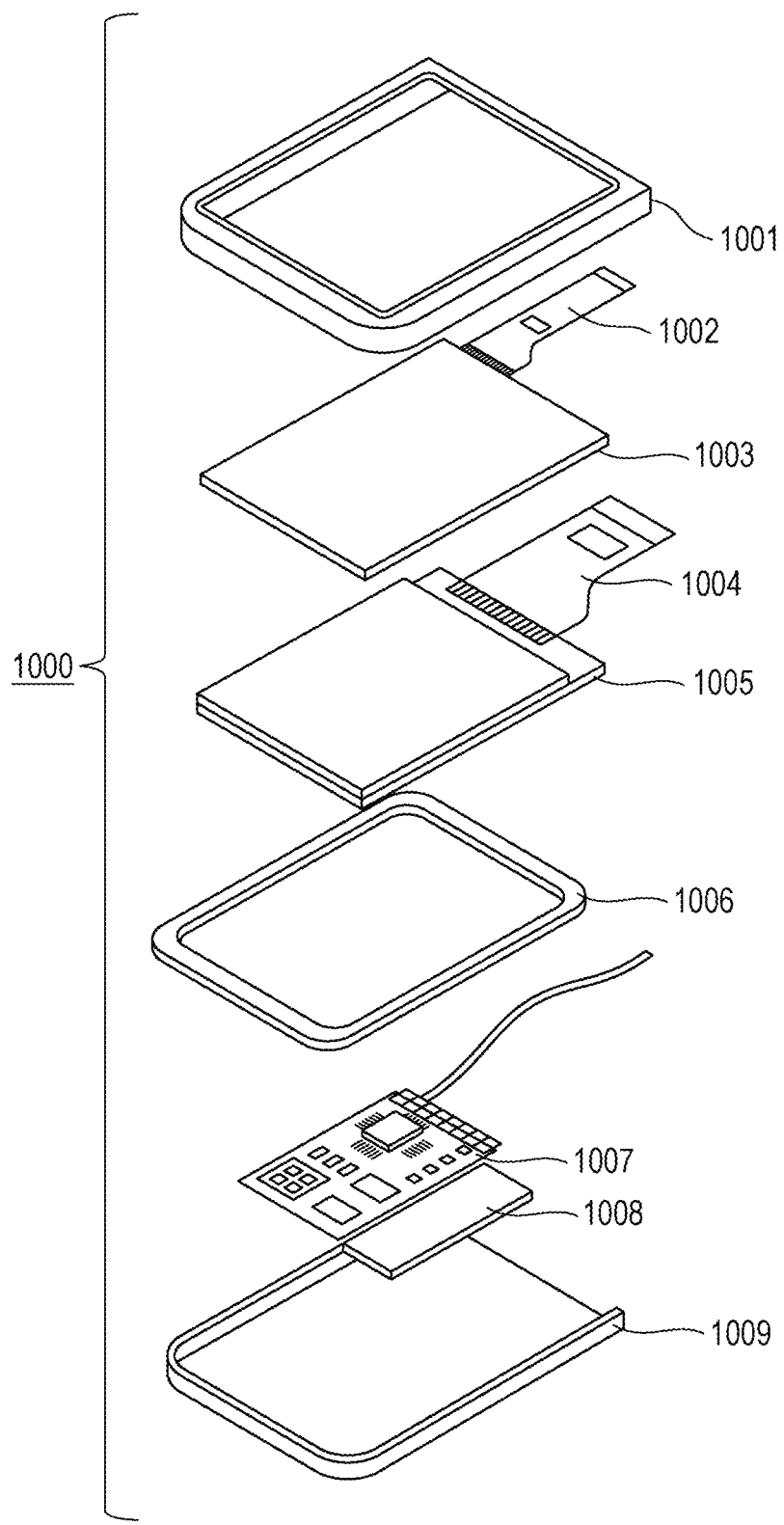
FIG. 2 is a schematic view of an example of a display apparatus according to an embodiment of the present disclosure.

FIG. 2 is a schematic view illustrating an example of a display apparatus according to the embodiment. A display apparatus 1000 may include a touch panel 1003, a display panel 1005, a frame 1006, a circuit substrate 1007, and a battery 1008 disposed between an upper cover 1001 and a lower cover 1009. The touch panel 1003 and the display panel 1005 are coupled to flexible printed circuits FPCs 1002 and 1004, respectively. The circuit substrate 1007 includes printed transistors. The battery 1008 need not be provided unless the display apparatus is a portable apparatus. The battery 1008 may be disposed at a different position even if the display apparatus is a portable apparatus.

The display apparatus according to the embodiment may be used for a display unit of an image pickup apparatus that includes an optical unit including multiple lenses and an image pickup device configured to receive light passing through the optical unit. The image pickup apparatus may include a display unit that displays information acquired by the image pickup device. The display unit may be a display unit exposed to the outside of the image pickup apparatus or a display unit disposed in a finder. The image pickup apparatus may be a digital camera or a digital camcorder. The image pickup apparatus may be rephrased as a photoelectric conversion apparatus.

Figure 3A:
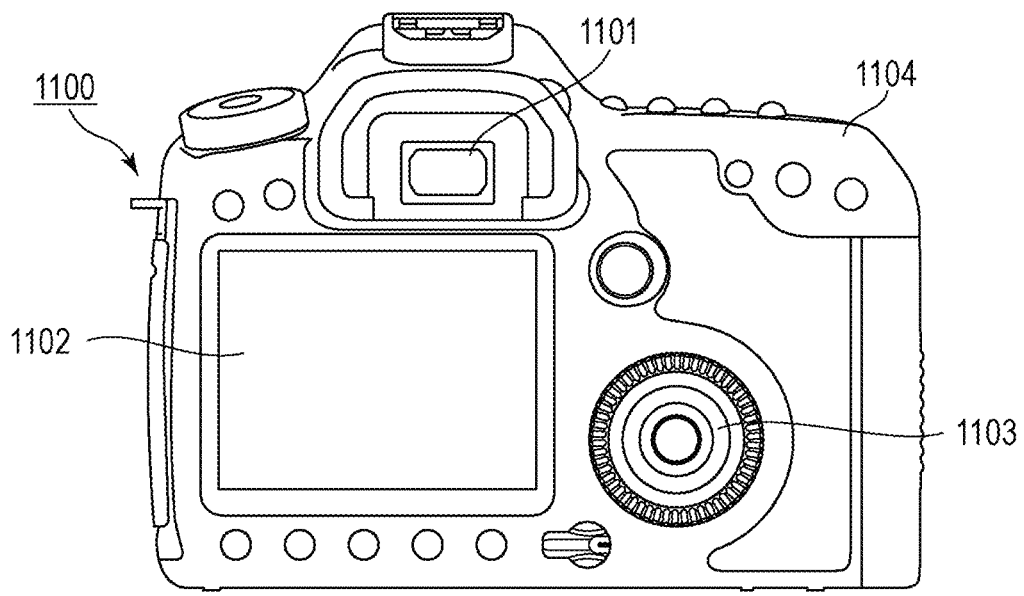
FIG. 3A is a schematic view of an example of an image pickup apparatus according to an embodiment of the present disclosure.

FIG. 3A is a schematic view illustrating an example of an image pickup apparatus according to the embodiment. An image pickup apparatus 1100 may include a viewfinder 1101, a rear display 1102, an operation unit 1103, and a housing 1104. The viewfinder 1101 may include the display apparatus according to the embodiment. In this case, the display apparatus may display environmental information, imaging instructions, and so forth in addition to an image to be captured. The environmental information may include, for example, the intensity of external light, the direction of the external light, the moving speed of a subject, and the possibility that a subject is shielded by a shielding material.

The timing suitable for imaging is only for a short time; thus, the information may be displayed as soon as possible. Accordingly, the display apparatus including the organic light-emitting element according to the embodiment can be used because of its short response time. The display apparatus including the organic light-emitting element can be used more suitably than liquid crystal displays for these units required to have a high display speed.

The image pickup apparatus 1100 includes an optical unit (not illustrated). The optical unit includes multiple lenses and is configured to form an image on an image pickup device in the housing 1104. The relative positions of the multiple lenses can be adjusted to adjust the focal point. This operation can also be performed automatically.

The display apparatus according to the embodiment may include a color filter having red, green, and blue portions. In the color filter, the red, green, and blue portions may be arranged in a delta arrangement.

A display apparatus according to the embodiment may be used for a display unit of an electronic apparatus, such as a portable terminal. In that case, the display apparatus may have both a display function and an operation function. Examples of the portable terminal include cellular phones, such as smartphones, tablets, and head-mounted displays.

Figure 3B:
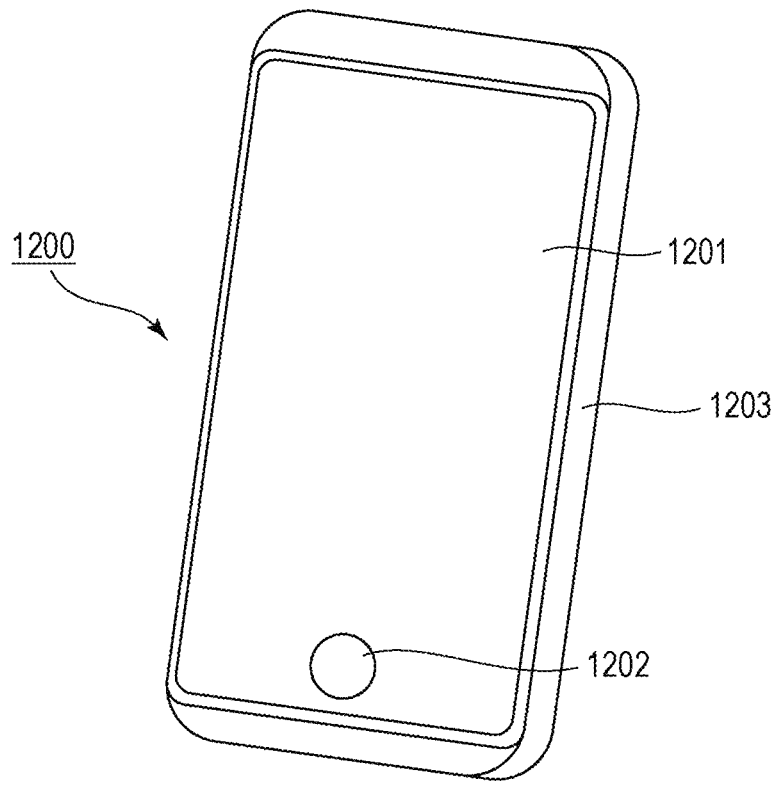
FIG. 3B is a schematic view of an example of a portable apparatus according to an embodiment of the present disclosure.

FIG. 3B is a schematic view illustrating an example of an electronic apparatus according to the embodiment. An electronic apparatus 1200 includes a display unit 1201, an operation unit 1202, and a housing 1203. The housing 1203 may accommodate a circuit, a printed circuit board including the circuit, a battery, and a communication unit. The operation unit 1202 may be a button or a touch-panel-type reactive unit. The operation unit may be a biometric recognition unit that recognizes a fingerprint to release the lock or the like. An electronic apparatus having a communication unit can also be referred to as a communication apparatus.

Figure 4A:
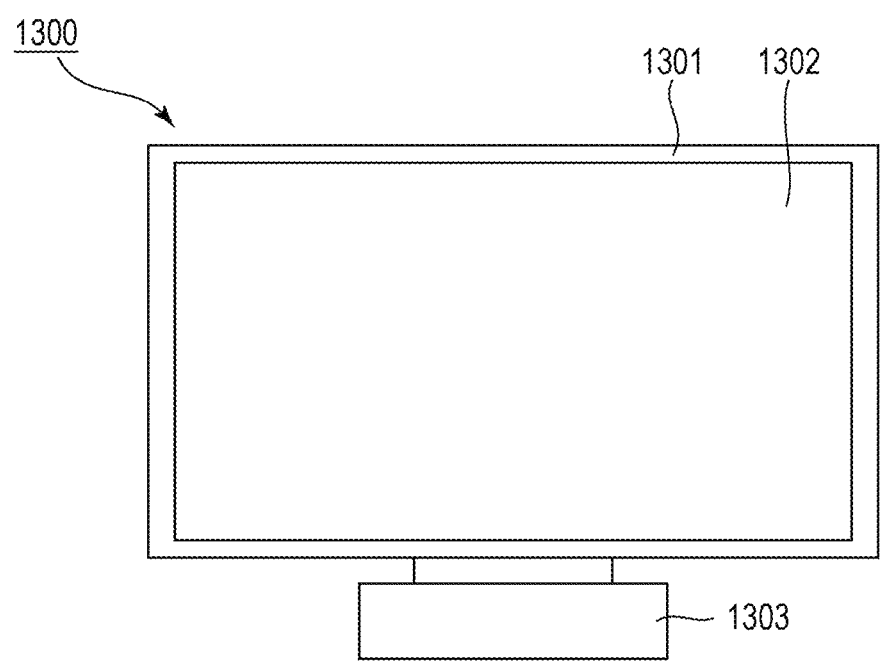
FIG. 4A is a schematic view of an example of a display apparatus according to an embodiment of the present disclosure.
Figure 4B:
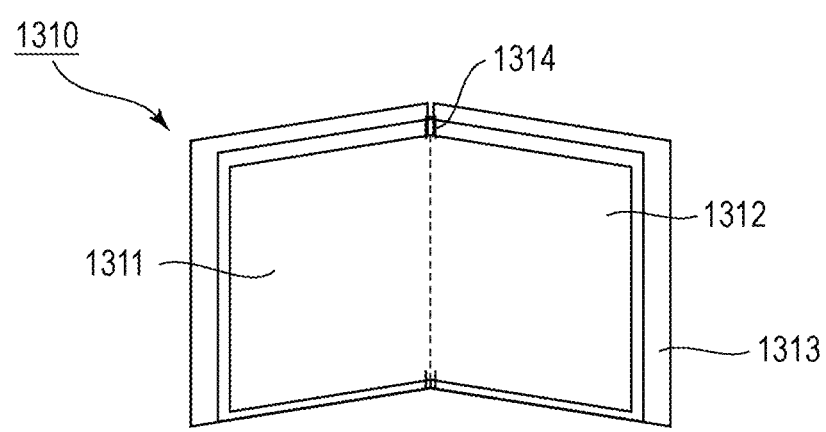
FIG. 4B is a schematic view of an example of a foldable display apparatus according to an embodiment of the present disclosure.

FIGS. 4A and 4B are schematic views illustrating examples of a display apparatus according to the embodiment. FIG. 4A illustrates a display apparatus, such as a television monitor or a personal computer monitor. A display apparatus 1300 includes a frame 1301 and a display unit 1302. The display unit 1302 may include a light-emitting element according to the embodiment. The display device 1300 also includes a base 1303 that supports the frame 1301 and the display unit 1302. The base 1303 is not limited to a form illustrated in FIG. 4A. The lower side of the frame 1301 may also serve as a base. The frame 1301 and the display unit 1302 may be curved in such a manner that the display surface of the display unit 1302 is curved. The radius of curvature may be 5,000 mm or more and 6,000 mm or less.

FIG. 4B is a schematic view illustrating another example of a display apparatus according to the embodiment. A display apparatus 1310 illustrated in FIG. 4B can be folded and is what is called a foldable display apparatus. The display apparatus 1310 includes a first display portion 1311, a second display portion 1312, a housing 1313, and an inflection point 1314. The first display portion 1311 and the second display portion 1312 may include a light-emitting element according to the embodiment. The first display portion 1311 and the second display portion 1312 may be a single, seamless display apparatus. The first display portion 1311 and the second display portion 1312 can be divided from each other at the inflection point. The first display portion 1311 and the second display portion 1312 may display different images from each other. Alternatively, a single image may be displayed in the first and second display portions.

Figure 5A:
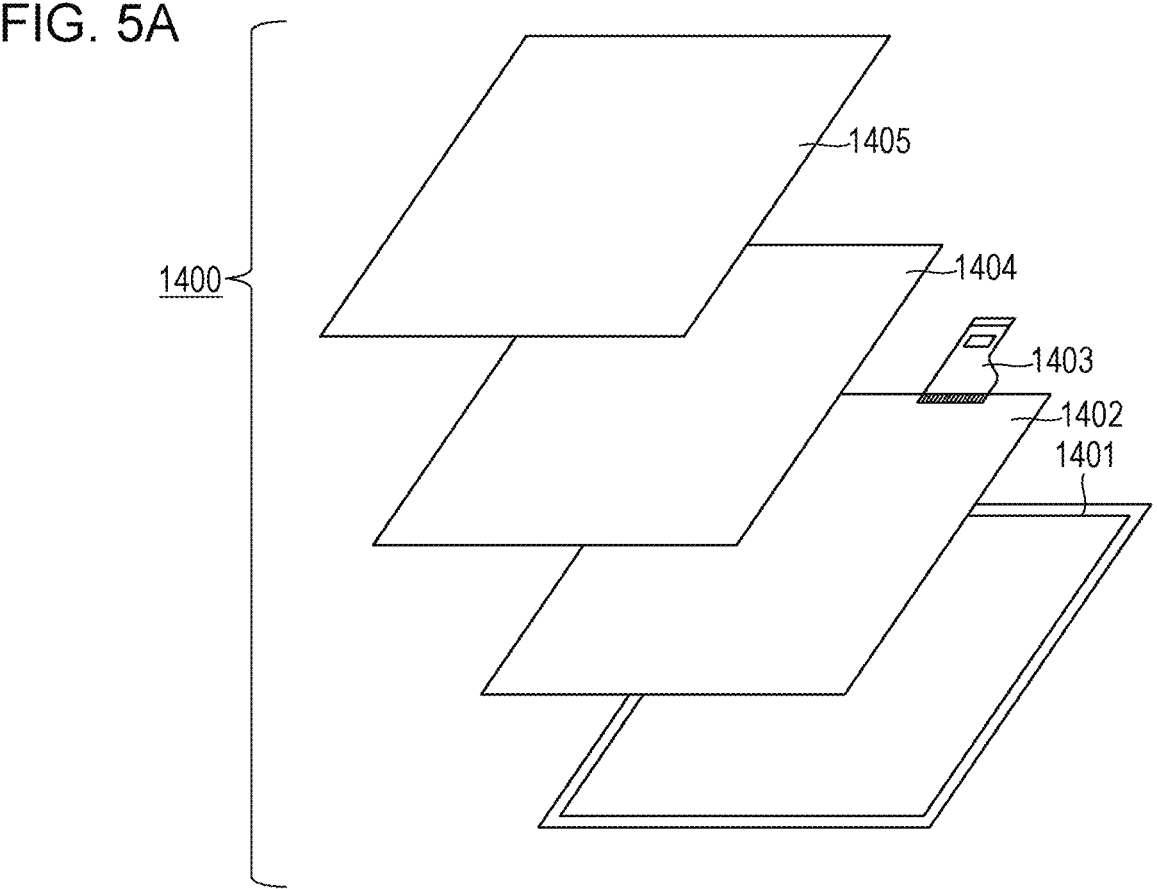
FIG. 5A is a schematic view of an example of a lighting device according to an embodiment of the present disclosure.

FIG. 5A is a schematic view illustrating an example of a lighting device according to the embodiment. A lighting device 1400 may include a housing 1401, a light source 1402, a circuit board 1403, an optical filter 1404 that transmits light emitted from the light source 1402, and a light diffusion unit 1405. The light source 1402 may include an organic light-emitting element according to the embodiment. The optical filter may be a filter that improves the color rendering properties of the light source. The light diffusion unit can effectively diffuse light from the light source to deliver the light to a wide range when used for illumination and so forth. The optical filter and the light diffusion unit may be disposed at the light emission side of the lighting device. A cover may be disposed at the outermost portion, as needed.

The lighting device is, for example, a device that lights a room. The lighting device may emit light of white, neutral white, or any color from blue to red. A light control circuit configured to control the light and a color control circuit configured to control the emission color may be provided. The lighting device may include the organic light-emitting element according to the embodiment and a power supply circuit coupled thereto. The power supply circuit is a circuit that converts an AC voltage into a DC voltage. The color temperature of white is 4,200 K, and the color temperature of neutral white is 5,000 K. The lighting device may include a color filter.

The lighting device according to the embodiment may include a heat dissipation unit. The heat dissipation unit is configured to release heat in the device to the outside of the device and is composed of, for example, a metal having a high specific heat and liquid silicone.

Figure 5B:
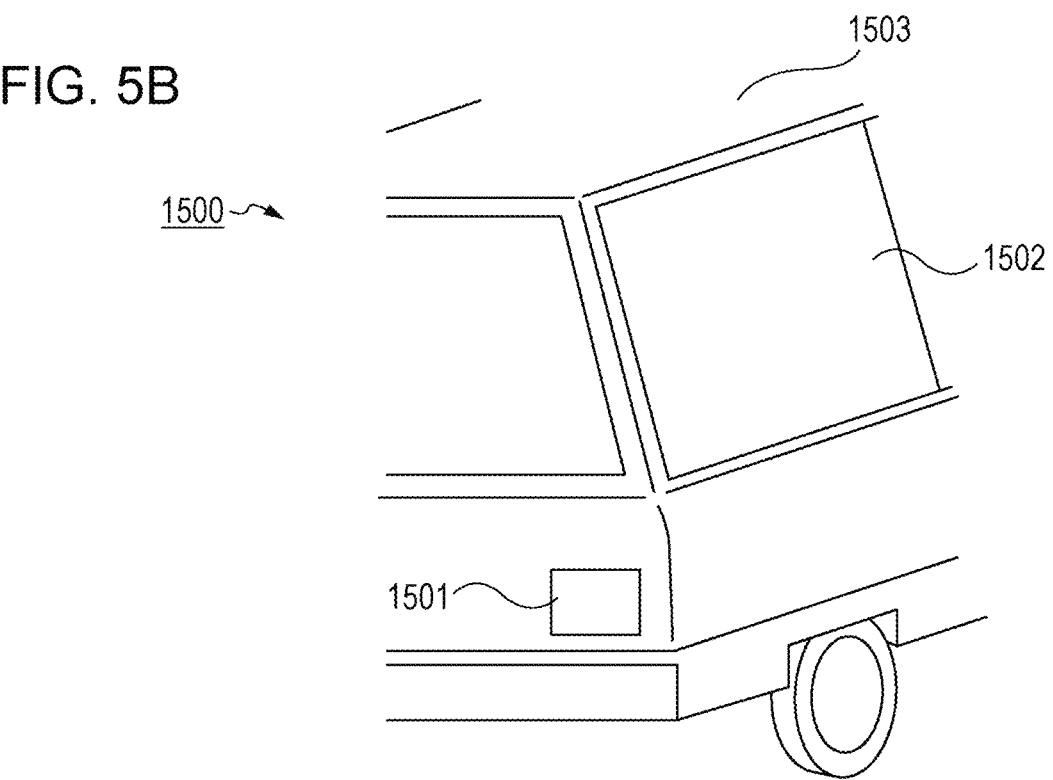
FIG. 5B is a schematic view of an automobile as an example of a moving object according to an embodiment of the present disclosure.

FIG. 5B is a schematic view illustrating an automobile as an example of a moving object. The automobile includes a tail lamp, which is an example of lighting units. An automobile 1500 includes a tail lamp 1501 and may be configured to light the tail lamp when a brake operation or the like is performed.

The tail lamp 1501 may include an organic light-emitting element according to the embodiment. The tail lamp 1501 may include a protective member that protects the organic light-emitting element. The protective member may be composed of any transparent material having high strength to some extent and can be composed of, for example, polycarbonate. The polycarbonate may be mixed with, for example, a furandicarboxylic acid derivative or an acrylonitrile derivative.

The automobile 1500 may include an automobile body 1503 and windows 1502 attached thereto. The windows 1502 may be transparent displays if the windows are not used to check the front and back of the automobile. The transparent displays may include an organic light-emitting element according to the embodiment. In this case, the components, such as the electrodes, of the organic light-emitting element are formed of transparent members.

The moving object according to the embodiment may be, for example, a ship, an aircraft, or a drone. The moving object may include a body and a lighting unit attached to the body. The lighting unit may emit light to indicate the position of the body. The lighting unit includes the organic light-emitting element according to the embodiment.

As described above, the use of an apparatus including the organic light-emitting element according to the embodiment enables a stable display with good image quality even for a long time.

EXAMPLES

While the present disclosure will be described below by examples, the present disclosure is not limited to these examples.

Example 1

Synthesis of Exemplified Compound C-1

Exemplified compound C-1 was synthesized according to the following scheme. The following scheme is a reaction scheme where in reaction scheme 1 above, substituent Gr is the substituent represented by formula [2] above, and $X_1$ and $X_2$ are each a methyl group.

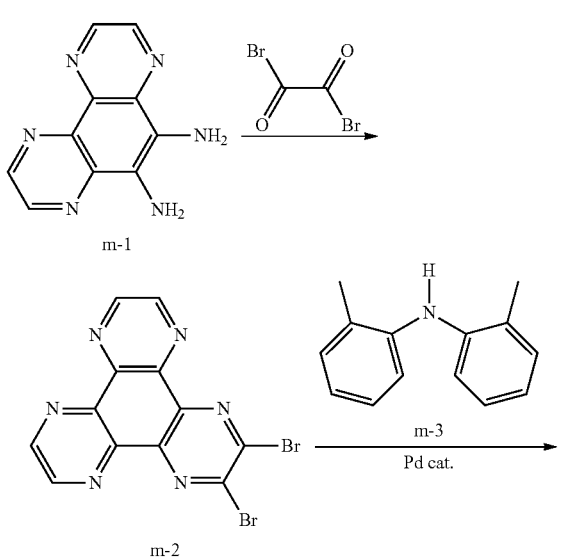

-continued

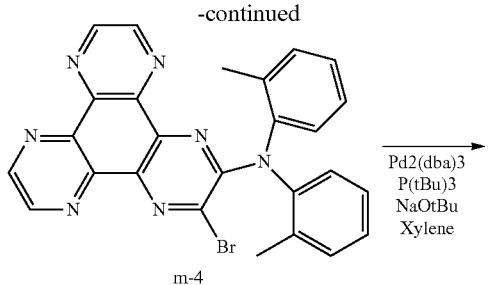

m-4

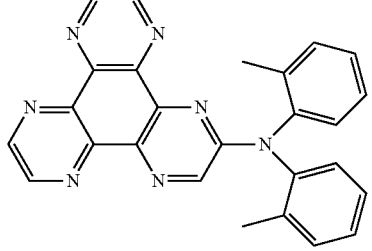

C-1

(1) Synthesis of Compound m-2

The following reagents and solvent were placed in a 200-mL recovery flask.
Compound m-1: 3.0 g
Oxalyl dibromide: 3.0 mL
Acetic acid: 60 mL The reaction solution was heated to reflux under stirring. After 3 hours, the reaction solution was brought to room temperature. The resulting precipitate was filtered by suction, washed with methanol, and then dried under reduced pressure to give 5.0 g (yield: 90%) of compound m-2.

(2) Synthesis of Compound m-4

The following reagents and solvent were placed in a 200-mL recovery flask.
Compound m-2: 2.0 g (5.10 mmol)
Compound m-3: 1.1 g (5.61 mmol)
Sodium tert-butoxide: 0.73 g (7.67 mmol)
Pd(dba)$_2$: 146 mg (0.52 mmol)
Tri-tert-butylphosphine: 318 mg (1.59 mmol)
o-Xylene: 60 mL The reaction solution was heated and stirred at 140° C. for 5 hours under a stream of nitrogen. After the completion of the reaction, filtration was performed through Celite, and then the filtrate was concentrated to dryness. The resulting solid was purified by silica gel column chromatography (toluene-ethyl acetate mixture) to give 1.95 g (yield: 75%) of m-4 as a yellow solid.

(3) Synthesis of Compound C-1

The following reagents and solvent were placed in a 200-mL recovery flask.
Compound m-4: 1.0 g (1.97 mmol)
Sodium tert-butoxide: 0.28 g (2.97 mmol)
Pd$_2$(dba)$_3$: 91 mg (0.99 mmol)
Tri-tert-butylphosphine: 60 mg (2.96 mmol)
o-Xylene: 30 mL The reaction solution was heated and stirred at 140° C. for 5 hours under a stream of nitrogen. After the completion of the reaction, filtration was performed through Celite, and then the filtrate was concentrated to dryness. The resulting solid was purified by silica gel column chromatography (toluene-ethyl acetate mixture) to give 0.67 g (yield: 80%) of C-1 as a yellow solid.

Yellow solid C-1 thus synthesized was subjected to mass spectrometry with MALDI-TOF-MS (Bruker Autoflex LRF). Mass spectrometry indicated that target compound C-1 was synthesized.

MALDI-TOF-MS
Measured value: m/z=429
Calculated value: $C_{26}H_{19}N_7$=429

Examples 2 to 11

Syntheses of Exemplified Compounds

As presented in Table 1, exemplified compounds of Examples 2 to 11 were synthesized as in Example 1, except that raw material m-3 in Example 1 was changed to raw material 1. The resulting exemplified compounds were subjected to mass spectrometry as in Example 1. Table 1 summarizes the measured values (m/z).

TABLE 1

| | Exemplified compound | Raw material 1 | m/z |
|---|---|---|---|
| Example 2 | C-2 | (structure) | 427 |
| Example 3 | C-3 | (structure) | 469 |
| Example 4 | C-4 | (structure) | 459 |
| Example 5 | C-5 | (structure) | 443 |
| Example 6 | C-10 | (structure) | 592 |
| Example 7 | C-13 | (structure) | 533 |

TABLE 1-continued

| Exemplified compound | Raw material 1 | m/z |
|---|---|---|
| Example 8 | C-16 | 517 |
| Example 9 | C-19 | 543 |
| Example 10 | C-30 | 539 |
| Example 11 | C-40 | 457 |

Example 12

Synthesis of Exemplified Compound D-2

Exemplified compound D-2 was synthesized according to the following scheme. The following scheme is a reaction scheme where in reaction scheme 2 above, each substituent Gr is a substituent represented by formula [3] above, and $X_1$ and $X_2$ are each a methyl group.

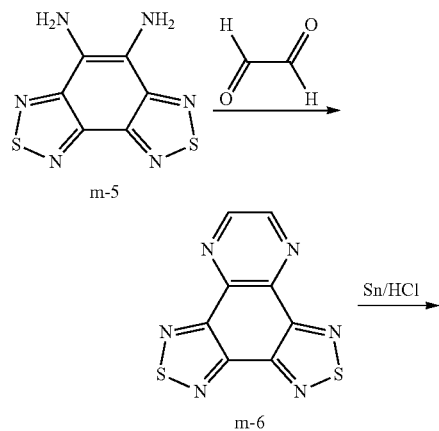

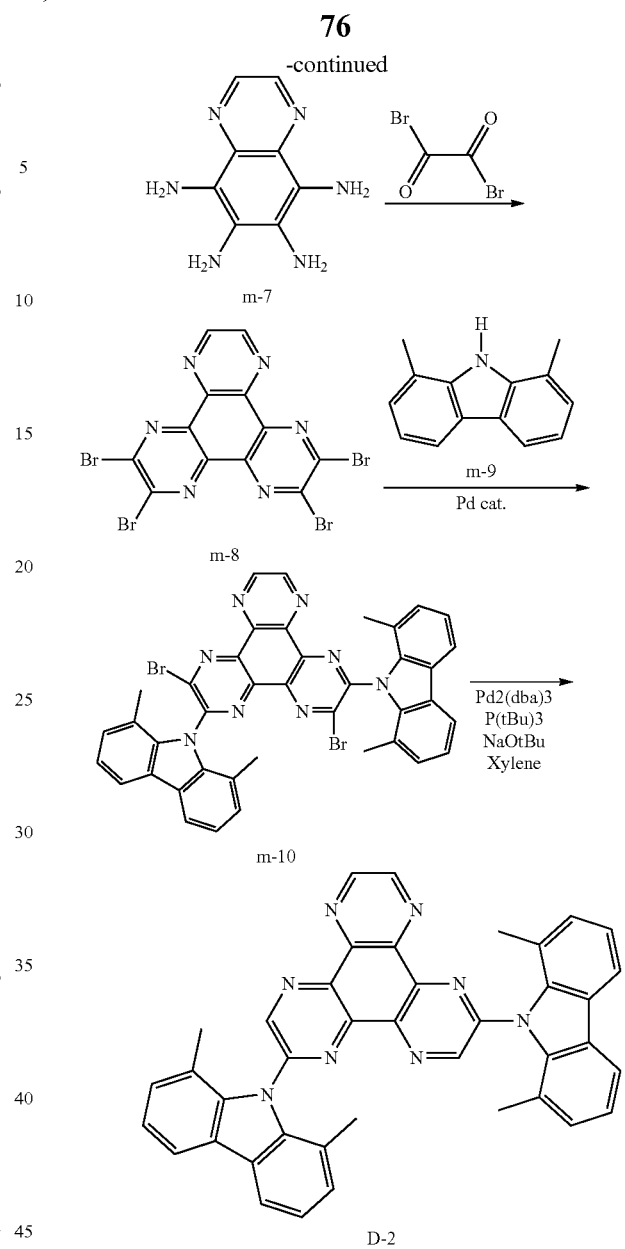

(1) Synthesis of Compound m-7

The following reagents and solvent were placed in a 500-mL recovery flask. Compound m-6 was synthesized via compound m-5 by a method described in J. Heterocyclic Chem., 12, 829(1975).

Compound m-6: 6.0 g
Tin powder: 11.6 g
Dioxane: 200 mL

The reaction solution was heated to reflux with stirring under a stream of nitrogen. Then 42 mL of concentrated hydrochloric acid was added dropwise thereto, and the mixture was reacted for about 6 hours. The reaction solution was brought to room temperature. The resulting precipitate was filtered by suction, washed with ethanol, and then dried at 90° C. under reduced pressure to give 6.2 g of the hydrochloride (tetrahydrochloride) of compound m-7.

(2) Synthesis of Compound m-8

The following reagents and solvent were placed in a 200-mL recovery flask.

Tetrahydrochloride of compound m-7: 3.0 g

Oxalyl dibromide: 3.3 mL
Acetic acid: 60 mL

The reaction solution was heated to reflux under stirring. After 3 hours, the reaction solution was brought to room temperature. The resulting precipitate was filtered by suction, washed with methanol, and then dried under reduced pressure to give 3.7 g of compound m-8.

(3) Synthesis of Compound m-10

The following reagents and solvent were placed in a 200-mL recovery flask.
Compound m-8: 2.0 g (3.63 mmol)
Compound m-9: 1.5 g (7.64 mmol)
Sodium tert-butoxide: 0.52 g (5.46 mmol)
Pd(dba)$_2$: 104 mg (0.18 mmol)
Tri-tert-butylphosphine: 110 mg (0.55 mmol)
o-Xylene: 60 mL The reaction solution was heated and stirred at 140° C. for 5 hours under a stream of nitrogen. After the completion of the reaction, filtration was performed through Celite, and then the filtrate was concentrated to dryness. The resulting solid was purified by silica gel column chromatography (toluene-ethyl acetate mixture) to give 2.0 g (yield: 70%) of m-10 as a yellow solid.

(4) Synthesis of Compound D-2

The following reagents and solvent were placed in a 200-mL recovery flask.
Compound m-10: 1.0 g (1.28 mmol)
Sodium tert-butoxide: 0.18 g (1.93 mmol)
Pd$_2$(dba)$_3$: 59 mg (0.64 mmol)
Tri-tert-butylphosphine: 39 mg (1.92 mmol)
o-Xylene: 30 mL The reaction solution was heated and stirred at 140° C. for 5 hours under a stream of nitrogen. After the completion of the reaction, filtration was performed through Celite, and then the filtrate was concentrated to dryness. The resulting solid was purified by silica gel column chromatography (toluene-ethyl acetate mixture) to give 0.64 g (yield: 80%) of D-2 as a yellow solid.

Yellow solid D-2 thus synthesized was subjected to mass spectrometry with MALDI-TOF-MS (Bruker Autoflex LRF). Mass spectrometry indicated that target compound D-2 was synthesized.

MALDI-TOF-MS
Measured value: m/z=620
Calculated value: $C_{40}H_{28}N_8$=620

Examples 13 to 19

Syntheses of Exemplified Compounds

As presented in Table 2, exemplified compounds of Examples 13 to 19 were synthesized as in Example 12, except that raw material m-9 in Example 12 was changed to raw material 2. The resulting exemplified compounds were subjected to mass spectrometry as in Example 12. Table 2 summarizes the measured values (m/z).

TABLE 2

| | Exemplified compound | Raw material 2 | m/z |
|---|---|---|---|
| Example 13 | D-1 | | 624 |
| Example 14 | D-3 | | 705 |
| Example 15 | D-4 | | 685 |
| Example 16 | D-5 | | 652 |
| Example 17 | D-6 | | 951 |
| Example 18 | D-7 | | 833 |
| Example 19 | D-10 | | 845 |

Example 20

Synthesis of Exemplified Compound E-2

Exemplified compound E-2 was synthesized according to the following scheme. The following scheme is a reaction scheme where in reaction scheme 3 above, each substituent Gr is a substituent represented by formula [3] above, and $X_1$ and $X_2$ are each a methyl group.

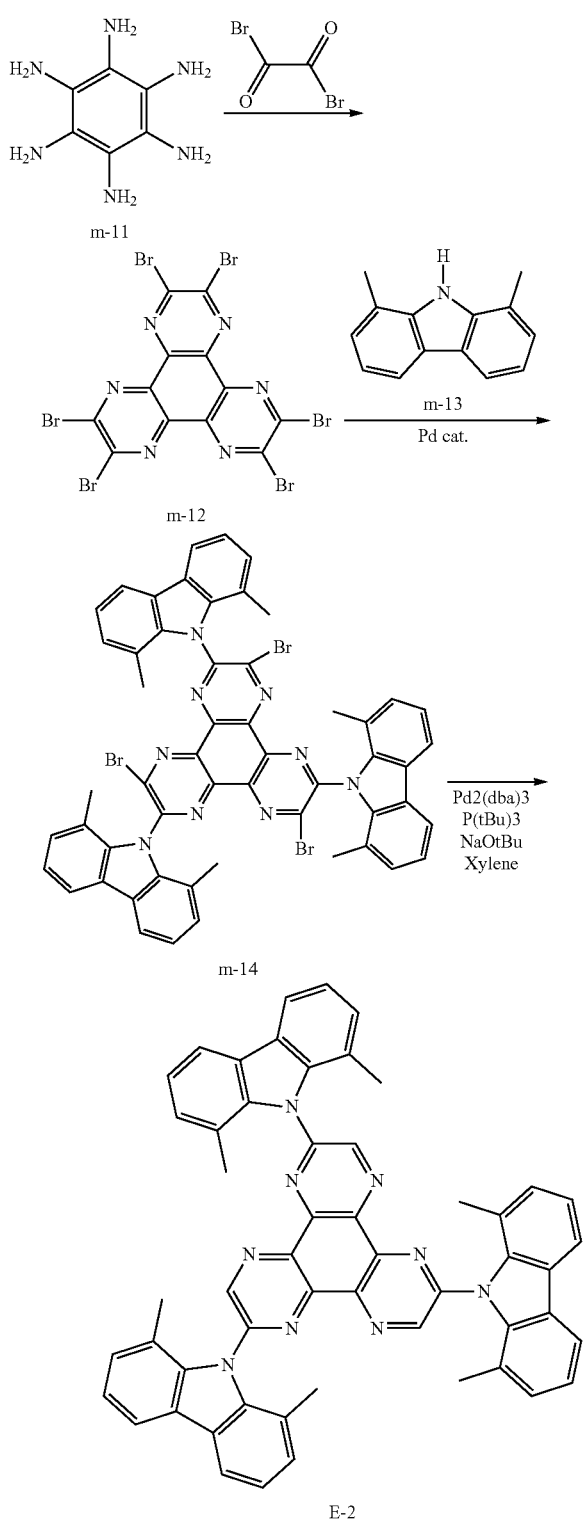

(1) Synthesis of Compound m-12
The following reagents and solvent were placed in a 200-mL recovery flask.
Compound m-11: 3.0 g
Oxalyl dibromide: 8.9 mL
Acetic acid: 90 mL
The reaction solution was heated to reflux under stirring. After 3 hours, the reaction solution was brought to room temperature. The resulting precipitate was filtered by suction, washed with methanol, and then dried under reduced pressure to give 11.4 g (yield: 90%) of compound m-12.

(2) Synthesis of Compound m-14
The following reagents and solvent were placed in a 200-mL recovery flask.
Compound m-12: 2.0 g (2.83 mmol)
Compound m-13: 1.7 g (6.76 mmol)
Sodium tert-butoxide: 0.40 g (4.24 mmol)
Pd(dba)$_2$: 46 mg (0.08 mmol)
Tri-tert-butylphosphine: 50 mg (0.25 mmol)
o-Xylene: 60 mL
The reaction solution was heated and stirred at 140° C. for 5 hours under a stream of nitrogen. After the completion of the reaction, filtration was performed through Celite, and then the filtrate was concentrated to dryness. The resulting solid was purified by silica gel column chromatography (toluene-ethyl acetate mixture) to give 2.4 g (yield: 80%) of m-14 as a yellow solid.

(3) Synthesis of Compound E-2
The following reagents and solvent were placed in a 200-mL recovery flask.
Compound m-14: 1.0 g (0.95 mmol)
Sodium tert-butoxide: 0.13 g (1.43 mmol)
Pd$_2$(dba)$_3$: 30 mg (0.48 mmol)
Tri-tert-butylphosphine: 29 mg (1.43 mmol)
o-Xylene: 30 mL
The reaction solution was heated and stirred at 140° C. for 5 hours under a stream of nitrogen. After the completion of the reaction, filtration was performed through Celite, and then the filtrate was concentrated to dryness. The resulting solid was purified by silica gel column chromatography (toluene-ethyl acetate mixture) to give 0.62 g (yield: 80%) of E-2 as a yellow solid.

Yellow solid E-2 thus synthesized was subjected to mass spectrometry with MALDI-TOF-MS (Bruker Autoflex LRF). Mass spectrometry indicated that target compound E-2 was synthesized.
MALDI-TOF-MS
Measured value: m/z=814
Calculated value: $C_{54}H_{39}N_9$=814

Examples 21 to 23

Synthesis of Exemplified Compounds

As presented in Table 3, exemplified compounds of Examples 21 to 23 were synthesized as in Example 20, except that raw material m-13 in Example 20 was changed to raw material 3. The resulting exemplified compounds were subjected to mass spectrometry as in Example 20. Table 3 summarizes the measured values (m/z).

TABLE 3

| | Exemplified compound | Raw material 3 | m/z |
|---|---|---|---|
| Example 21 | E-1 | (structure) | 820 |

TABLE 3-continued

| | Exemplified compound | Raw material 3 | m/z |
|---|---|---|---|
| Example 22 | E-3 | 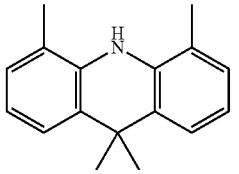 [SMILES: Cc1cccc2c1Nc1c(C)cccc1C2(C)C] | 940 |
| Example 23 | E-7 | 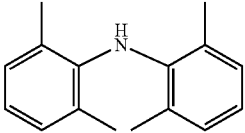 [SMILES: Cc1cccc(C)c1Nc1c(C)cccc1C] | 904 |

Example 24

In this Example, an organic light-emitting element having a bottom-emission structure was produced in which an anode, a hole injection layer, a hole transport layer, an electron-blocking layer, a light-emitting layer, a hole-blocking layer, an electron transport layer, an electron injection layer, and a cathode were sequentially formed on a substrate.

An ITO film was formed on a glass substrate and subjected to desired patterning to form an ITO electrode (anode). The ITO electrode had a thickness of 100 nm. The substrate on which the ITO electrode had been formed in this way was used as an ITO substrate in the following steps. Next, vacuum evaporation was performed by resistance heating in a vacuum chamber to continuously form organic compound layers and an electrode layer (cathode) presented in Table 4 on the ITO substrate. Here, the electrode (cathode) opposite the ITO electrode had an electrode area of 3 mm².

TABLE 4

| | | Material | Proportion in light-emitting layer (% by mass) | Thickness (nm) |
|---|---|---|---|---|
| Electrode layer | Cathode | Al | — | 100 |
| Organic compound layer | Electron injection layer (EIL) | LiF | — | 1 |
| | Electron transport layer (ETL) | ET2 | — | 15 |
| | Hole-blocking layer (HBL) | ET11 | — | 15 |
| Light-emitting layer (EML) | Host | EM11 | 88 | 20 |
| | Light-emitting material | C-2 | 12 | |
| | Electron-blocking layer (EBL) | HT12 | — | 15 |
| | Hole transport layer (HTL) | HT3 | — | 30 |
| | Hole injection layer (HIL) | HT16 | — | 5 |

The characteristics of the resulting device were measured and evaluated. As the initial characteristics associated with the light emission, green light emission with a maximum external quantum efficiency (E.Q.E.) of 5.9% was obtained. With regard to measurement instruments, specifically, the current-voltage characteristics were measured with a Hewlett-Packard 4140B microammeter, and the luminance was measured with a Topcon BM7. The device was subjected to a continuous operation test at a current density of 50 mA/cm². The time when the percentage of luminance degradation reached 5% (LT95) was measured to be 120 hours.

Examples 25 to 29

Organic light-emitting elements were produced in the same manner as in Example 24, except that the materials used to form the layers in Example 24 were appropriately changed to compounds listed in Table 5. The layers not listed in Table 5 had the same configurations as in Example 24. The characteristics of the resulting devices were measured and evaluated in the same way as in Example 24. Table 5 presents the results of the measurements, together with the results of the measurements in Example 24.

TABLE 5

| | HTL | EBL | EML Host | Light-emitting material | HBL | ETL | E.Q.E. [%] | LT95 [h] | Emission color |
|---|---|---|---|---|---|---|---|---|---|
| Example 24 | HT3 | HT12 | EM11 | C-2 | ET11 | ET2 | 5.9 | 120 | green |
| Example 25 | HT3 | HT12 | EM11 | C-1 | ET12 | ET2 | 5.8 | 125 | green |
| Example 26 | HT3 | HT10 | EM10 | C-2 | ET12 | ET2 | 5.6 | 115 | green |

TABLE 5-continued

| | HTL | EBL | Host | Light-emitting material | HBL | ETL | E.Q.E. [%] | LT95 [h] | Emission color |
|---|---|---|---|---|---|---|---|---|---|
| Example 27 | HT3 | HT12 | EM9 | D-2 | ET12 | ET2 | 5.6 | 113 | green |
| Example 28 | HT2 | HT11 | EM14 | D-3 | ET12 | ET2 | 5.5 | 90 | green |
| Example 29 | HT2 | HT10 | EM32 | E-2 | ET12 | ET5 | 5.7 | 85 | green |

Example 30

In this Example, an organic light-emitting element having a bottom-emission structure was produced in which an anode, a hole injection layer, a hole transport layer, an electron-blocking layer, a light-emitting layer, a hole-blocking layer, an electron transport layer, an electron injection layer, and a cathode were sequentially formed on a substrate.

An ITO film was formed on a glass substrate and subjected to desired patterning to form an ITO electrode (anode). The ITO electrode had a thickness of 100 nm. The substrate on which the ITO electrode had been formed in this way was used as an ITO substrate in the following steps. Next, vacuum evaporation was performed by resistance heating in a vacuum chamber to continuously form organic compound layers and an electrode layer (cathode) presented in Table 6 on the ITO substrate. Here, the electrode (cathode) opposite the ITO electrode had an electrode area of 3 mm².

TABLE 6

| | | Material | Proportion in light-emitting layer (% by mass) | Thickness (nm) |
|---|---|---|---|---|
| Electrode layer | Cathode | Al | — | 100 |
| Organic compound layer | Electron injection layer (EIL) | LiF | — | 1 |
| | Electron transport layer (ETL) | ET2 | — | 15 |
| | Hole-blocking layer (HBL) | ET12 | — | 15 |
| | Light-emitting layer (EML) Host | EM10 | 82 | 20 |
| | Assist | C-1 | 15 | |
| | Light-emitting material | GD6 | 3 | |
| | Electron-blocking layer (EBL) | HT12 | — | 15 |
| | Hole transport layer (HTL) | HT3 | — | 30 |
| | Hole injection layer (HIL) | HT16 | — | 5 |

The characteristics of the resulting device were measured and evaluated. As the initial characteristics associated with the light emission, green light emission with a maximum external quantum efficiency (E.Q.E.) of 6.8% was obtained. With regard to measurement instruments, specifically, the current-voltage characteristics were measured with a Hewlett-Packard 4140B microammeter, and the luminance was measured with a Topcon BM7. The device was subjected to a continuous operation test at a current density of 50 mA/cm². The time when the percentage of luminance degradation reached 5% (LT95) was measured to be 153 hours.

Examples 31 to 45 and Comparative Examples 1 and 2

Organic light-emitting elements were produced in the same manner as in Example 30, except that the compounds used in Example 30 were appropriately changed to compounds listed in Table 7. The layers not listed in Table 7 had the same configurations as in Example 30. The characteristics of the resulting devices were measured and evaluated in the same way as in Example 30. Table 7 presents the results of the measurements, together with the results of the measurements in Example 30. Compounds (comparative compounds) used as assist materials in Comparative examples 1 and 2 are illustrated below.

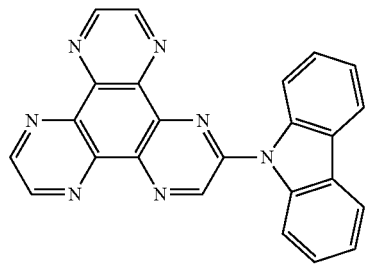

F-1

-continued

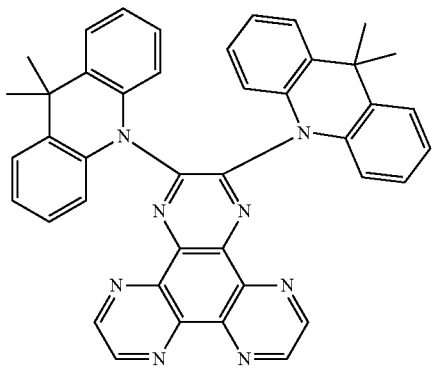

F-2 have a structure with a large steric effect, the compound has a structure in which the substituents and the basic skeleton are arranged on the same plane and which has a high degree of flatness. Accordingly, comparative compound F-2 also has a large difference between $S_1$ and $T_1$, and delayed fluorescence is less likely to occur; thus, the organic light-emitting element of Comparative example 2 has low luminous efficiency.

The 5% degradation lifetime (LT95) of the organic light-emitting element in each of Comparative examples 1 and 2 was 50 hours or less, which indicated low durability. This is presumably because comparative compounds F-1 and F-2 have a high degree of flatness and thus are likely to undergo molecular association, have poor film properties, and crystallize easily.

In contrast, the organic light-emitting elements of Examples 30 to 45 exhibited good results in both luminous

TABLE 7

| | | | | EML | | | | | |
| | | | | Light-emitting | | | E.Q.E. | LT95 | |
| | HTL | EBL | Host | Assist | material | HBL | ETL | [%] | [h] | Emission color |
|---|---|---|---|---|---|---|---|---|---|---|
| Example 30 | HT3 | HT12 | EM10 | C-1 | GD6 | ET12 | ET2 | 6.8 | 153 | green |
| Example 31 | HT3 | HT12 | EM11 | C-2 | GD6 | ET12 | ET2 | 6.9 | 150 | green |
| Example 32 | HT3 | HT11 | EM11 | C-3 | GD6 | ET11 | ET2 | 6.6 | 160 | green |
| Example 33 | HT3 | HT12 | EM10 | C-4 | GD7 | ET12 | ET2 | 6.9 | 170 | green |
| Example 34 | HT2 | HT11 | EM9 | C-10 | GD7 | ET12 | ET2 | 6.8 | 150 | green |
| Example 35 | HT2 | HT10 | EM9 | C-30 | GD6 | ET12 | ET5 | 6.8 | 165 | green |
| Example 36 | HT3 | HT11 | EM14 | C-40 | GD9 | ET12 | ET2 | 7.1 | 140 | green |
| Example 37 | HT3 | HT12 | EM11 | D-1 | GD1 | ET11 | ET2 | 6.4 | 195 | green |
| Example 38 | HT3 | HT10 | EM14 | D-2 | GD1 | ET12 | ET2 | 6.4 | 190 | green |
| Example 39 | HT3 | HT12 | EM32 | D-10 | GD4 | ET11 | ET2 | 6.3 | 190 | green |
| Example 40 | HT2 | HT12 | EM11 | E-2 | GD6 | ET12 | ET2 | 5.9 | 200 | green |
| Example 41 | HT2 | HT12 | EM11 | C-2 | RD1 | ET12 | ET5 | 7 | 270 | red |
| Example 42 | HT3 | HT10 | EM9 | C-3 | RD1 | ET12 | ET2 | 7.1 | 250 | red |
| Example 43 | HT2 | HT12 | EM14 | D-2 | RD1 | ET11 | ET5 | 6.8 | 300 | red |
| Example 44 | HT3 | HT10 | EM32 | E-1 | RD1 | ET12 | ET2 | 6.5 | 350 | red |
| Example 45 | HT3 | HT12 | EM14 | E-2 | RD1 | ET12 | ET2 | 6.4 | 300 | red |
| Comparative example 1 | HT3 | HT11 | EM14 | F-1 | GD9 | ET12 | ET2 | 3.8 | 30 | green |
| Comparative example 2 | HT3 | HT12 | EM14 | F-2 | RD1 | ET12 | ET2 | 3.9 | 40 | red |

As presented in Table 7, the maximum external quantum efficiency (E.Q.E.) of each of the organic light-emitting elements of Comparative examples 1 and 2 was as low as 4.0 or less. That is, the organic light-emitting elements in Comparative examples 1 and 2 had low luminous efficiency. Comparative compound F-1 used as the assist material in Comparative example 1 is compound a-1 illustrated in FIG. 6. As described above, compound a-1 has a structure in which the amino group, which is a substituent, is attached to the hexaazatriphenylene skeleton, which is the basic skeleton. However, because the substituent does not have a structure with a large steric effect, the compound has a structure in which the substituent and the basic skeleton are arranged on the same plane and which has a high degree of flatness. This results in a large overlap between the electron orbital distribution of the HOMO and the electron orbital distribution of the LUMO, and a large energy difference between $S_1$ and $T_1$. As a result, the reverse intersystem crossing is less likely to occur, and delayed fluorescence is less likely to occur; thus, the organic light-emitting element of Comparative example 1 has low luminous efficiency. The same is true for comparative compound F-2 used as an assist material in Comparative example 2. As in comparative compound F-1, because each of the substituents does not efficiency and durability. Each of the compounds according to embodiments of the present disclosure used as the assist materials in Examples 30 to 45 has a substituent having a relatively large steric effect with respect to the hexaazatriphenylene skeleton, which is the basic skeleton. Thus, each substituent is arranged in a sterically twisted manner with respect to the basic skeleton, resulting in a low degree of flatness. This results in a small overlap between the electron orbital distribution of the HOMO and the electron orbital distribution of the LUMO, and a small energy difference between $S_1$ and $T_1$. This seemingly facilitates the reverse intersystem crossing to promote delayed fluorescence, leading to high luminous efficiency. The above structure seemingly resulted in the light-emitting layer with a high degree of amorphous nature, leading to good durability.

In Example 36 and Comparative example 1, the same structure is used, except for the assist material. In Example 36, compound C-36, which is one of the compounds according to an embodiment of the present disclosure, is used as an assist material. In Comparative example 1, comparative compound F-1 is used as an assist material. As described above, compound C-36 contains an amino group, which is a substituent attached to the basic skeleton, having a relatively large steric effect, so that the substituent is arranged in a sterically twisted manner with respect to the basic skeleton. This seems to result in a small energy difference between $S_1$ and $T_1$ to facilitate delayed fluorescence.

Accordingly, the organic light-emitting element of Example 36 had superior luminous efficiency and durability, compared to Comparative example 1 in which comparative compound F-1 that does not easily induce delayed fluorescence was used.

In Example 45 and Comparative example 2, the same structure is used, except for the assist material. In Example 45, compound E-1, which is one of the compounds according to an embodiment of the present disclosure, is used as an assist material. In Comparative example 2, comparative compound F-2 is used as an assist material. As described above, compound E-1 contains amino groups, which are substituents attached to the basic skeleton, having a relatively large steric effect, so that the substituents are arranged in a sterically twisted manner with respect to the basic skeleton. This seemingly results in a small energy difference between $S_1$ and $T_1$ to facilitate delayed fluorescence. Accordingly, the organic light-emitting element of Example 45 had superior luminous efficiency and durability, compared to Comparative example 2 in which comparative compound F-2 that does not easily induce delayed fluorescence was used.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2020-198285 filed Nov. 30, 2020, which is hereby incorporated by reference herein in its entirety.

What is claimed is:

1. An organic compound represented by formula [1]:

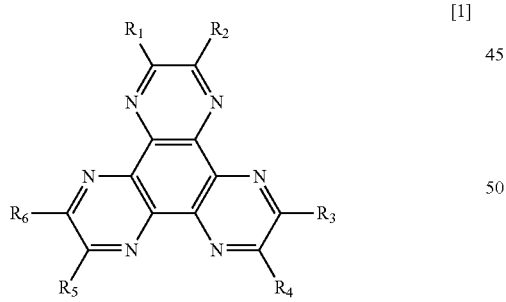

where in formula [1], $R_1$ to $R_6$ are each independently selected from the group consisting of a hydrogen atom, a hydrocarbon group, and substituents represented by formulae [2] to [18], at least one of $R_1$ and $R_2$ and at least one of $R_3$ and $R_4$ are a substituent represented by any of formulae [2] to [18], at least any one of $R_1$ and $R_2$ is a hydrogen atom or a hydrocarbon group, at least any one of $R_3$ and $R_4$ is a hydrogen atom or a hydrocarbon group, and at least any one of $R_5$ and $R_6$ is a hydrogen atom,

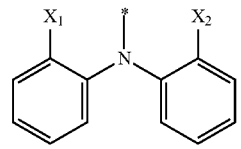

[2]

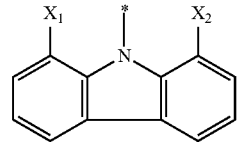

[3]

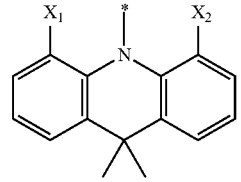

[4]

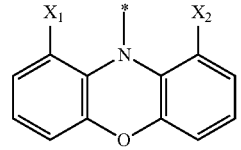

[5]

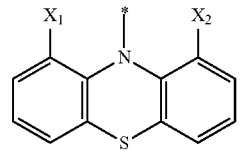

[6]

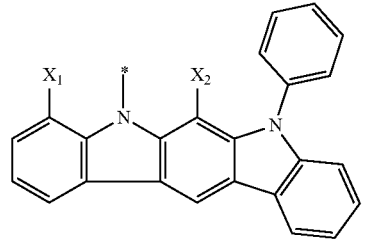

[7]

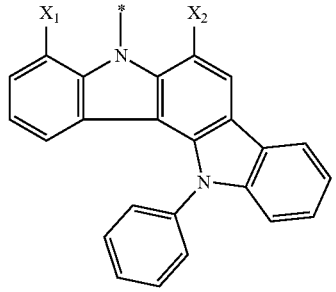

[8]

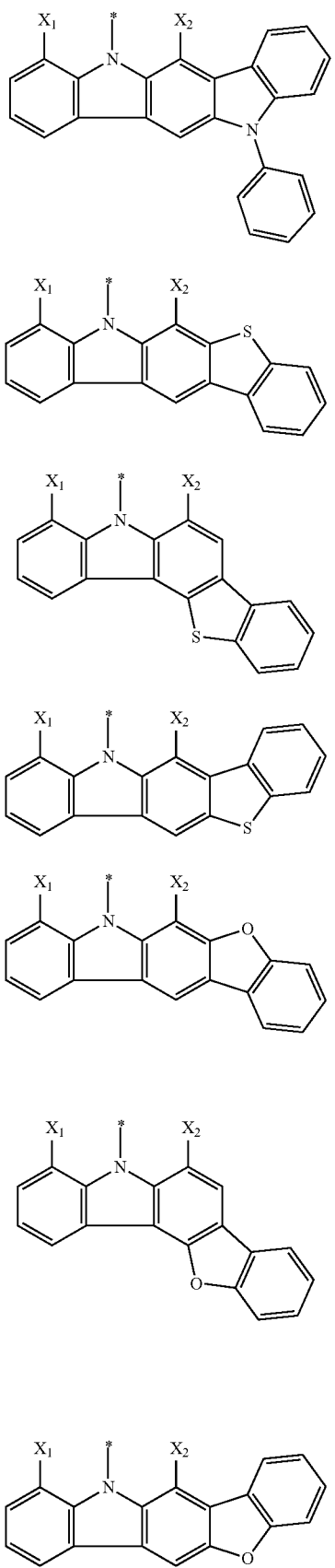

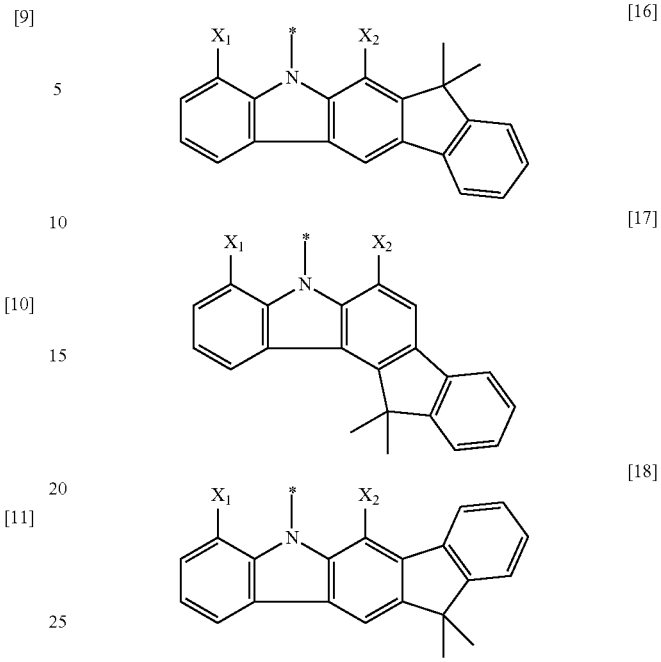

where in formulae [2] to [18], $X_1$ and $X_2$ are each independently selected from a substituted or unsubstituted alkyl group, a substituted or unsubstituted aryl group, and a substituted or unsubstituted heterocyclic group.

2. The organic compound according to claim 1, wherein in formula [1], $R_1$ and $R_3$ are each independently selected from the substituents represented by formulae [2] to [18], $R_2$ and $R_4$ to $R_6$ are each independently a hydrogen atom or a hydrocarbon group.

3. The organic compound according to claim 1, wherein in formula [1], $R_1$, $R_3$, and $R_5$ are each independently selected from the substituents represented by formulae [2] to [18], and $R_2$, $R_4$, and $R_6$ are each independently a hydrogen atom or a hydrocarbon group.

4. The organic compound according to claim 1, wherein in formula [2], $X_1$ and $X_2$ are each independently selected from a substituted or unsubstituted alkyl group having 1 to 6 carbon atoms, a substituted or unsubstituted aryl group having 6 to 10 carbon atoms, and a substituted or unsubstituted heterocyclic group having 3 to 9 carbon atoms.

5. The organic compound according to claim 1, wherein in formula [1], $R_1$ to $R_6$ are each independently selected from the group consisting of a hydrogen atom, a substituted or unsubstituted alkyl group 1 to 6 carbon atoms, a substituted or unsubstituted aryl group having 6 to 10 carbon atoms, and the substituents represented by formulae [2] to [18].

6. The organic compound according to claim 1, wherein in formula [1], $R_1$ to $R_6$ are each independently selected from the group consisting of a hydrogen atom and the substituents represented by formulae [2] to [18].

7. The organic compound according to claim 1, wherein in formula [2], $X_1$ and $X_2$ are each independently a substituted or unsubstituted alkyl group having 1 to 6 carbon atoms.

8. The organic compound according to claim 1, wherein in formula [2], $X_1$ and $X_2$ are each independently a substituted or unsubstituted aryl group having 6 to 10 carbon atoms.

9. The organic compound according to claim 1, wherein in formula [2], $X_1$ and $X_2$ are each independently a substituted or unsubstituted heterocyclic group having 3 to 9 carbon atoms.

10. An organic light-emitting element, comprising:
an anode;
a cathode; and
at least one organic compound layer disposed between the anode and the cathode,
wherein the at least one organic compound layer contains the organic compound according to claim 1.

11. The organic light-emitting element according to claim 10, wherein the at least one organic compound layer containing the organic compound is a light-emitting layer.

12. The organic light-emitting element according to claim 10, wherein the light-emitting layer further contains a host material.

13. The organic light-emitting element according to claim 12, wherein the host material is a hydrocarbon compound.

14. The organic light-emitting element according to claim 12, wherein the light-emitting layer further contains a light-emitting material.

15. The organic light-emitting element according to claim 14, wherein the light-emitting material is a hydrocarbon compound.

16. The organic light-emitting element according to claim 11, wherein the light-emitting layer emits green light or red light.

17. A display apparatus, comprising:
multiple pixels,
at least one of the multiple pixels including:
the organic light-emitting element according to claim 10; and
a transistor coupled to the organic light-emitting element.

18. A photoelectric conversion apparatus, comprising:
an optical unit including multiple lenses;
an image pickup device that receives light passing through the optical unit; and
a display unit that displays an image captured by the image pickup device,
wherein the display unit includes the organic light-emitting element according to claim 10.

19. An electronic apparatus, comprising:
a display unit including the organic light-emitting element according to claim 10;
a housing provided with the display unit; and
a communication unit being disposed in the housing and communicating with an outside.

20. A lighting device, comprising:
a light source including the organic light-emitting element according to claim 10; and
a light diffusion unit or an optical filter configured to transmit light emitted from the light source.

21. A moving object, comprising:
a lighting unit including the organic light-emitting element according to claim 10; and
a body provided with the lighting unit.

* * * * *